United States Patent
Li

(10) Patent No.: US 11,236,089 B2
(45) Date of Patent: Feb. 1, 2022

(54) SUBSTITUTED PYRROLOPYRIDINES AS ATR INHIBITORS

(71) Applicant: BlueValley Pharmaceutical LLC, Pleasanton, CA (US)

(72) Inventor: Xiang Li, San Jose, CA (US)

(73) Assignee: BlueValley Pharmaceutical LLC, Pleasanton, CA (US)

( * ) Notice: Subject to any disclaimer, the term of this patent is extended or adjusted under 35 U.S.C. 154(b) by 50 days.

(21) Appl. No.: 16/801,322

(22) Filed: Feb. 26, 2020

(65) Prior Publication Data

US 2020/0207763 A1    Jul. 2, 2020

Related U.S. Application Data

(63) Continuation of application No. PCT/US2018/049460, filed on Sep. 5, 2018.

(60) Provisional application No. 62/616,642, filed on Jan. 12, 2018, provisional application No. 62/555,645, filed on Sep. 8, 2017.

(51) Int. Cl.
   *C07D 471/04*    (2006.01)
   *A61P 35/04*    (2006.01)

(52) U.S. Cl.
   CPC ............ *C07D 471/04* (2013.01); *A61P 35/04* (2018.01)

(58) Field of Classification Search
   CPC .............................. C07D 471/04; A61P 35/04
   USPC ...................................................... 514/234.5
   See application file for complete search history.

(56) References Cited

U.S. PATENT DOCUMENTS

2011/0306613 A1   12/2011   Foote et al.

FOREIGN PATENT DOCUMENTS

| WO | 2007/080382 A1 | 7/2007 |
| WO | 2012/101654 A2 | 8/2012 |
| WO | 2019014618 | * 7/2017 |
| WO | 2019036641 | * 8/2017 |

OTHER PUBLICATIONS

Kiesel et al., LC-MS/MS assay for the simultaneous quantitation of the ATM inhibitor AZ31 and the ATR inhibitor AZD6738 in mouse plasma. J Pharm Biomed Anal. May 10, 2017;138:158-165.
International Search Report and Written Opinion for Application No. PCT/US2018/049460, dated Oct. 30, 2018, 12 pages.
International Preliminary Report on Patentability for Application No. PCT/US2018/049460, dated Mar. 28, 2019, 20 pages.

* cited by examiner

*Primary Examiner* — Niloofar Rahmani
(74) *Attorney, Agent, or Firm* — McCarter & English, LLP; Yu Lu; Wei Song

(57) ABSTRACT

The disclosure includes compounds of Formula (I) wherein A, W, m, $R_5$, $R_6$, $R_7$, and $R_8$, are defined herein. Also disclosed is a method for treating a neoplastic disease with these compounds.

5 Claims, No Drawings

SUBSTITUTED PYRROLOPYRIDINES AS ATR INHIBITORS

CROSS-REFERENCE TO RELATED APPLICATIONS

This application is a continuation of International Application No. PCT/US2018/049460, filed on Sep. 5, 2018, which claims the benefit of the filing date of U.S. Provisional Application No. 62/555,645, filed on Sep. 8, 2017, and 62/616,642, filed on Jan. 12, 2018. The entire contents of the aforementioned applications are incorporated herein by reference.

BACKGROUND OF THE INVENTION

ATR (also known as FRAP-Related Protein 1; FRP1; MEC1; SCKL; SECKL1) protein kinase is a member of the PI3-Kinase like kinase (PIKK) family of proteins that are involved in repair and maintenance of the genome and its stability (reviewed in Cimprich K. A. and Cortez D. 2008, Nature Rev. Mol. Cell Biol. 9:616-627). These proteins co-ordinate response to DNA damage, stress and cell-cycle perturbation. Indeed ATM and ATR, two members of the family of proteins, share a number of downstream substrates that are themselves recognised components of the cell cycle and DNA-repair machinery e.g. Chk1, BRCA1, p53 (Lakin N D et al, 1999, Oncogene; Tibbets R S et al, 2000, Genes & Dev.). Whilst the substrates of ATM and ATR are to an extent shared, the trigger to activate the signalling cascade is not shared and ATR primarily responds to stalled replication forks (Nyberg K. A. et al., 2002, Ann. Rev. Genet. 36:617-656; Shechter D. et al. 2004, DNA Repair 3:901-908) and bulky DNA damage lesions such as those formed by ultraviolet (UV) radiation (Wright J. A. et al, 1998, Proc. Natl. Acad. Sci. USA, 23:7445-7450) or the UV mimetic agent, 4-nitroquinoline-1-oxide, 4NQO (Ikenaga M. et al. 1975, Basic Life Sci. 5b, 763-771). However, double strand breaks (DSB) detected by ATM can be processed into single strand breaks (SSB) recruiting ATR; similarly SSB, detected by ATR can generate DSB, activating ATM. There is therefore a significant interplay between ATM and ATR.

Mutations of the ATR gene that result in complete loss of expression of the ATR protein are rare and in general are not viable. Viability may only result under heterozygous or hypomorphic conditions. The only clear link between ATR gene mutations and disease exists in a few patients with Seckel syndrome which is characterized by growth retardation and microcephaly (O'Driscoll M et al, 2003 Nature Genet. Vol 3, 497-501). Cells from patients with hypomorphic germline mutations of ATR (seckel syndrome) present a greater susceptibility to chromosome breakage at fragile sites in presence of replication stress compared to wild type cells (Casper 2004). Disruption of the ATR pathway leads to genomic instability. Patients with Seckel syndrome also present an increased incidence of cancer, suggestive of the role of ATR in this disease in the maintenance of genome stability.

Moreover, duplication of the ATR gene has been described as a risk factor in rhabdomyosarcomas (Smith L et al, 1998, Nature Genetics 19, 39-46). Oncogene-driven tumorigenesis may be associated with ATM loss-of-function and therefore increased reliance on ATR signalling (Gilad 2010). Evidence of replication stress has also been reported in several tumor types such as colon and ovarian cancer, and more recently in glioblastoma, bladder, prostate and breast (Gorgoulis et al, 2005; Bartkova et al. 2005a; Fan et al., 2006; Tort et al, 2006; Nuciforo et al, 2007; Bartkova et al., 2007a). Loss of G1 checkpoint is also frequently observed during tumorigenesis. Tumor cells that are deficient in G1 checkpoint controls, in particular p53 deficiency, are susceptible to inhibition of ATR activity and present with premature chromatin condensation (PCC) and cell death (Ngheim et al, PNAS, 98, 9092-9097).

ATR is essential to the viability of replicating cells and is activated during S-phase to regulate firing of replication origins and to repair damaged replication forks (Shechter D et al, 2004, Nature cell Biology Vol 6 (7) 648-655). Damage to replication forks may arise due to exposure of cells to clinically relevant cytotoxic agents such as hydroxyurea (HU) and platinums (O'Connell and Cimprich 2005; 118, 1-6). ATR is activated by most cancer chemotherapies (Wilsker D et al, 2007, Mol. Cancer Ther. 6(4) 1406-1413). Biological assessment of the ability of ATR inhibitors to sensitise to a wide range of chemotherapies have been evaluated. Sensitisation of tumor cells to chemotherapeutic agents in cell growth assays has been noted and used to assess how well weak ATR inhibitors (such as Caffeine) will sensitise tumor cell lines to cytotoxic agents (Wilsker D. et al, 2007, Mol Cancer Ther. 6 (4)1406-1413; Sarkaria J. N. et al, 1999, Cancer Res. 59, 4375-4382). Moreover, a reduction of ATR activity by siRNA or ATR knock-in using a dominant negative form of ATR in cancer cells has resulted in the sensitisation of tumor cells to the effects of a number of therapeutic or experimental agents such as antimetabolites (5-FU, Gemcitabine, Hydroxyurea, Metotrexate, Tomudex), alkylating agents (Cisplatin, Mitomycin C, Cyclophosphamide, MMS) or double-strand break inducers (Doxorubicin, Ionizing radiation) (Cortez D. et al. 2001, Science, 294:1713-1716; Collis S. J. et al, 2003, Cancer Res. 63:1550-1554; Cliby W. A. et al, 1998, EMBO J. 2:1 9-169) suggesting that the combination of ATR inhibitors with some cytotoxic agents might be therapeutically beneficial. An additional phenotypic assay has been described to define the activity of specific ATR inhibitory compounds is the cell cycle profile (PJ Hurley, D Wilsker and F Bunz, Oncogene, 2007, 26, 2535-2542). Cells deficient in ATR have been shown to have defective cell cycle regulation and distinct characteristic profiles, particularly following a cytotoxic cellular insult. Furthermore, there are proposed to be differential responses between tumor and normal tissues in response to modulation of the ATR axis and this provides further potential for therapeutic intervention by ATR inhibitor molecules (Rodnguez-Bravo V et al, Cancer Res., 2007, 67, 11648-11656).

Another compelling utility of ATR-specific phenotypes is aligned with the concept of synthetic lethality and the observation that tumor cells that are deficient in G1 checkpoint controls, in particular p53 deficiency, are susceptible to inhibition of ATR activity resulting in premature chromatin condensation (PCC) and cell death (Ngheim et al, PNAS, 98, 9092-9097). In this situation, S-phase replication of DNA occurs but is not completed prior to M-phase initiation due to failure in the intervening checkpoints resulting in cell death from a lack of ATR signalling. The G2/M checkpoint is a key regulatory control involving ATR (Brown E. J. and Baltimore D., 2003, Genes Dev. 17, 615-628) and it is the compromise of this checkpoint and the prevention of ATR signalling to its downstream partners which results in PCC.

Consequently, the genome of the daughter cells is compromised and viability of the cells is lost (Ngheim et al, PNAS, 98, 9092-9097). It has thus been proposed that inhibition of ATR may prove to be an efficacious approach to future cancer therapy (Collins I. and Garret M. D., 2005, Curr. Opin. Pharmacol., 5:366-373; Kaelin W. G. 2005, Nature Rev. Cancer, 5:689-698) in the appropriate genetic context such as tumors with defects in ATM function or other S-phase checkpoints.

In summary ATR inhibitors have the potential to sensitise tumor cells to ionising radiation or DNA-damage inducing chemotherapeutic agents, have the potential to induce selective tumor cell killing as well as to induce synthetic lethality in subsets of tumor cells with defects in DNA damage response. Although ATK inhibitors such as AZD-6738, VX-970 have made a significant contribution to the art, there is a strong need for continuing search in this field of art for the improved pharmaceutics.

SUMMARY OF THE INVENTION

The present invention relates to pyrimidinyl compounds, processes for their preparation, pharmaceutical compositions containing them and their use in therapy, for example in the treatment of proliferative disease such as cancer and particularly in disease mediated by Ataxia-telangiectasia mutated and RAD-3 related protein kinase inhibitors, commonly referred to as ATR.

In a first embodiment, this invention provides compounds of the Formula (I), or an N-oxide thereof, or a pharmaceutically acceptable salt, solvate, polymorph, tautomer, stereoisomer, an isotopic form, or a prodrug of said compound of Formula (I) or N-oxide thereof:

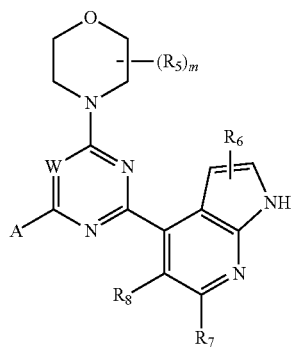

wherein
A is hydrogen,

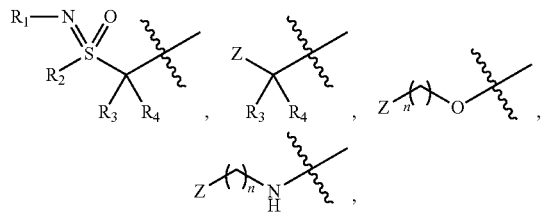

cyano, cycloalkyl, cycloalkenyl, heterocycloalkyl, heterocycloalkenyl, aryl, or heteroaryl;

$R_1$ is alkyl, or —$CD_3$;

$R_2$ is alkyl or halo-alkyl;

each of $R_3$, and $R_4$, independently, is H, D, halo, alkyl, or halo-alkyl; or $R_3$ and $R_4$ together with the atom to which they are attached forms a cycloalkyl or heterocycloalkenyl;

Z is H, D, OH, halo, amine, cyano, C(O)OH, C(O)NH$_2$, alkyl, alkenyl, alkynyl, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl of Z is optionally substituted with one or more $R_d$;

W is N or C($R_a$);

each of $R_5$, $R_6$, $R_7$, and $R_8$, independently, is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, NH(CH$_2$)$_p$$R_a$, C(O)$R_a$, S(O)$R_a$, SO$_2$$R_a$, C(O)O$R_a$, OC(O)$R_a$, N$R_b$$R_c$, P(O)$R_b$$R_c$, alkyl-P(O)$R_b$$R_c$, C(O)N($R_b$)$R_c$, N($R_b$)C(O)$R_c$, S(O)(=N($R_b$))$R_c$, —N=S(O)$R_b$$R_c$, SO$_2$N($R_b$)$R_c$, or N($R_b$)SO$_2$$R_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, alkenyl, alkynyl, halo, cyano, amine, nitro, hydroxy, =O, C(O)NHOH, C(O)OH, C(O)NH$_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$; and $R_e$ is H, D, alkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl; and m, and n, independently, is 0, 1, 2, or 3.

In a second embodiment, the invention provides a compound represented by Formula (II):

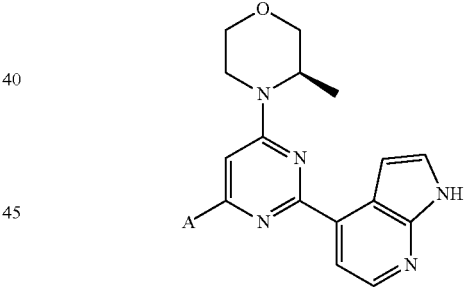

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, therapeutic uses thereof, and use of the compounds for the manufacture of a medicament for treating the disease/disorder.

This invention also relates to a method of treating a neoplastic disease, by administering to a subject in need thereof an effective amount of one or more of the compounds, modifications, and/or salts, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:
imino(methyl)(1-(2-(5-methyl-1H-pyrrolo[2,3-b]pyridin-4-yl)-6-((R)-3-methylmorpholino)pyrimidin-4-yl)cyclopropyl)-l6-sulfanone,
(1-(2-(5-(tert-butyl)-1H-pyrrolo[2,3-b]pyridin-4-yl)-6-((R)-3-methylmorpholino)pyrimidin-4-yl)cyclopropyl)(imino)(methyl)-l6-sulfanone,
imino(1-(2-(5-isopropoxy-1H-pyrrolo[2,3-b]pyridin-4-yl)-6-((R)-3-methylmorpholino)pyrimidin-4-yl)cyclopropyl)(methyl)-l6-sulfanone,
imino(1-(2-(5-methoxy-1H-pyrrolo[2,3-b]pyridin-4-yl)-6-((R)-3-methylmorpholino)pyrimidin-4-yl)cyclopropyl)(methyl)-l6-sulfanone,
imino(methyl)(1-(2-(5-(methylamino)-1H-pyrrolo[2,3-b]pyridin-4-yl)-6-((R)-3-methylmorpholino)pyrimidin-4-yl)cyclopropyl)-l6-sulfanone,
imino(1-(2-(5-(isopropylamino)-1H-pyrrolo[2,3-b]pyridin-4-yl)-6-((R)-3-methylmorpholino)pyrimidin-4-yl)cyclopropyl)(methyl)-l6-sulfanone,
(1-(2-(6-(tert-butyl)-1H-pyrrolo[2,3-b]pyridin-4-yl)-6-((R)-3-methylmorpholino)pyrimidin-4-yl)cyclopropyl)(imino)(methyl)-l6-sulfanone,
imino(1-(2-(6-methoxy-1H-pyrrolo[2,3-b]pyridin-4-yl)-6-((R)-3-methylmorpholino)pyrimidin-4-yl)cyclopropyl)(methyl)-l6-sulfanone,
imino(1-(2-(6-isopropoxy-1H-pyrrolo[2,3-b]pyridin-4-yl)-6-((R)-3-methylmorpholino)pyrimidin-4-yl)cyclopropyl)(methyl)-l6-sulfanone,
imino(methyl)(1-(2-(6-(methylamino)-1H-pyrrolo[2,3-b]pyridin-4-yl)-6-((R)-3-methylmorpholino)pyrimidin-4-yl)cyclopropyl)-l6-sulfanone,
imino(1-(2-(6-(isopropylamino)-1H-pyrrolo[2,3-b]pyridin-4-yl)-6-((R)-3-methylmorpholino)pyrimidin-4-yl)cyclopropyl)(methyl)-l6-sulfanone,
(1-(5-chloro-6-((R)-3-methylmorpholino)-2-(1H-pyrrolo[2,3-b]pyridin-4-yl)pyrimidin-4-yl)cyclopropyl)(imino)(methyl)-l6-sulfanone,
imino(methyl)(1-(4-((R)-3-methylmorpholino)-6-(1H-pyrrolo[2,3-b]pyridin-4-yl)-1,3,5-triazin-2-yl)cyclopropyl)-l6-sulfanone,
imino(methyl)(1-(5-methyl-6-((R)-3-methylmorpholino)-2-(1H-pyrrolo[2,3-b]pyridin-4-yl)pyrimidin-4-yl)cyclopropyl)-l6-sulfanone,
imino(methyl)(1-(6-((R)-3-methylmorpholino)-2-(1H-pyrrolo[2,3-b]pyridin-4-yl)-5-(trifluoromethyl)pyrimidin-4-yl)cyclopropyl)-l6-sulfanone,
(S)-methyl(methylimino)(1-(6-((R)-3-methylmorpholino)-2-(1H-pyrrolo[2,3-b]pyridin-4-yl)pyrimidin-4-yl)cyclopropyl)-l6-sulfanone,
(S)-(isopropylimino)(methyl)(1-(6-((R)-3-methylmorpholino)-2-(1H-pyrrolo[2,3-b]pyridin-4-yl)pyrimidin-4-yl)cyclopropyl)-l6-sulfanone,
(S)-methyl(methylimino)(1-(6-((R)-3-methylmorpholino)-2-(1H-pyrrolo[2,3-b]pyridin-4-yl)pyrimidin-4-yl)cyclobutyl)-l6-sulfanone,
(S)-(isopropylimino)(methyl)(1-(6-((R)-3-methylmorpholino)-2-(1H-pyrrolo[2,3-b]pyridin-4-yl)pyrimidin-4-yl)cyclobutyl)-l6-sulfanone,
(1-(6-(1,4-oxazepan-4-yl)-2-(1H-pyrrolo[2,3-b]pyridin-4-yl)pyrimidin-4-yl)cyclopropyl)(methyl)(methylimino)-l6-sulfanone,
(1-(6-((R)-4,4-difluoro-2-methylpiperidin-1-yl)-2-(1H-pyrrolo[2,3-b]pyridin-4-yl)pyrimidin-4-yl)cyclopropyl)(methyl)(methylimino)-l6-sulfanone,
(1-(6-((R)-4,4-difluoro-2-methylpiperidin-1-yl)-2-(1H-pyrrolo[2,3-b]pyridin-4-yl)pyrimidin-4-yl)cyclopropyl)(imino)(methyl)-l6-sulfanone,
(1-(2-(1H-pyrrolo[2,3-b]pyridin-4-yl)-6-(2-oxa-7-azaspiro[3.5]nonan-7-yl)pyrimidin-4-yl)cyclopropyl)(methyl)(methylimino)-l6-sulfanone,
(1-(2-(1H-pyrrolo[2,3-b]pyridin-4-yl)-6-(2-oxa-6-azaspiro[3.4]octan-6-yl)pyrimidin-4-yl)cyclopropyl)(methyl)(methylimino)-l6-sulfanone,
(1-(2-(1H-pyrrolo[2,3-b]pyridin-4-yl)-6-((S)-3-(trifluoromethyl)morpholino)pyrimidin-4-yl)cyclopropyl)(methyl)(methylimino)-l6-sulfanone,
4-(6-(1-(N,S-dimethylsulfonimidoyl)cyclopropyl)-2-(1H-pyrrolo[2,3-b]pyridin-4-yl)pyrimidin-4-yl)morpholine-3-carboxylic acid,
methyl(methylimino)(1-(6-(2-methylmorpholino)-2-(1H-pyrrolo[2,3-b]pyridin-4-yl)pyrimidin-4-yl)cyclopropyl)-l6-sulfanone,
4-(6-(1-(N,S-dimethylsulfonimidoyl)cyclopropyl)-2-(1H-pyrrolo[2,3-b]pyridin-4-yl)pyrimidin-4-yl)morpholine-2-carboxylic acid,
imino(1-(6-((R)-3-methylmorpholino)-2-(1H-pyrrolo[2,3-b]pyridin-4-yl)pyrimidin-4-yl)cyclopropyl)(trifluoromethyl)-l6-sulfanone,
(methylimino)(1-(6-((R)-3-methylmorpholino)-2-(1H-pyrrolo[2,3-b]pyridin-4-yl)pyrimidin-4-yl)cyclopropyl) (trifluoromethyl)-l6-sulfanone,
(1-(2-(2,3-dihydro-6H-[1,4]dioxino[2,3-b]pyrrolo[3,2-e]pyridin-9-yl)-6-((R)-3-methylmorpholino)pyrimidin-4-yl)cyclopropyl)(imino)(methyl)-l6-sulfanone,
(1-(2-(5H-[1,3]dioxolo[4,5-b]pyrrolo[3,2-e]pyridin-8-yl)-6-((R)-3-methylmorpholino)pyrimidin-4-yl)cyclopropyl)(imino)(methyl)-l6-sulfanone,
(1-(2-(3,4-dihydro-2H,7H-[1,4]dioxepino[2,3-b]pyrrolo[3,2-e]pyridin-10-yl)-6-((R)-3-methylmorpholino)pyrimidin-4-yl)cyclopropyl) (imino)(methyl)-l6-sulfanone,
(S)-methyl((methyl-d3)imino)(1-(6-((R)-3-methylmorpholino)-2-(1H-pyrrolo[2,3-b]pyridin-4-yl)pyrimidin-4-yl)cyclopropyl)-l6-sulfanone,
(R)-2-methyl-2-(6-(3-methylmorpholino)-2-(1H-pyrrolo[2,3-b]pyridin-4-yl)pyrimidin-4-yl)propanenitrile, (R)-4-(2-(1H-pyrrolo[2,3-b]pyridin-4-yl)-6-(1,1,1-trifluoro-2-methylpropan-2-yl)pyrimidin-4-yl)-3-methylmorpholine,
1,1,1-trifluoro-2-(6-((R)-3-methylmorpholino)-2-(1H-pyrrolo[2,3-b]pyridin-4-yl)pyrimidin-4-yl)propan-2-ol,
(R)-2-(6-(3-methylmorpholino)-2-(1H-pyrrolo[2,3-b]pyridin-4-yl)pyrimidin-4-yl)propan-2-ol,
(R)-2-(6-(3-methylmorpholino)-2-(1H-pyrrolo[2,3-b]pyridin-4-yl)pyrimidin-4-yl)propan-2-amine,
(R)—N-((3,3-difluorocyclobutyl)methyl)-6-(3-methylmorpholino)-2-(1H-pyrrolo[2,3-b]pyridin-4-yl)pyrimidin-4-amine;
6-((R)-3-methylmorpholino)-2-(1H-pyrrolo[2,3-b]pyridin-4-yl)-N—(((S)-tetrahydrofuran-3-yl)methyl)pyrimidin-4-amine,
6-((R)-3-methylmorpholino)-2-(1H-pyrrolo[2,3-b]pyridin-4-yl)-N—(((R)-tetrahydrofuran-3-yl)methyl)pyrimidin-4-amine,
(R)-6-(3-methylmorpholino)-N-(oxetan-3-ylmethyl)-2-(1H-pyrrolo[2,3-b]pyridin-4-yl)pyrimidin-4-amine,
(R)—N-((4,4-difluorocyclohexyl)methyl)-6-(3-methylmorpholino)-2-(1H-pyrrolo[2,3-b]pyridin-4-yl)pyrimidin-4-amine,
(R)-6-(3-methylmorpholino)-2-(1H-pyrrolo[2,3-b]pyridin-4-yl)-N-((tetrahydro-2H-pyran-4-yl)methyl)pyrimidin-4-amine,
(R)—N-ethyl-6-(3-methylmorpholino)-2-(1H-pyrrolo[2,3-b]pyridin-4-yl)pyrimidin-4-amine,
(R)—N-(2-fluoro-2-methylpropyl)-6-(3-methylmorpholino)-2-(1H-pyrrolo[2,3-b]pyridin-4-yl)pyrimidin-4-amine,
(R)—N-(3,3-difluorocyclobutyl)-6-(3-methylmorpholino)-2-(1H-pyrrolo[2,3-b]pyridin-4-yl)pyrimidin-4-amine,
(R)—N-(cyclopropylmethyl)-6-(3-methylmorpholino)-2-(1H-pyrrolo[2,3-b]pyridin-4-yl)pyrimidin-4-amine.
(R)-3-methyl-4-(6-morpholino-2-(1H-pyrrolo[2,3-b]pyridin-4-yl)pyrimidin-4-yl)morpholine,
(R)-4-(2-(1H-pyrrolo[2,3-b]pyridin-4-yl)pyrimidin-4-yl)-3-methylmorpholine,
(R)-3-methyl-4-(6-methyl-2-(1H-pyrrolo[2,3-b]pyridin-4-yl)pyrimidin-4-yl)morpholine,
(R)-4-(6-isopropyl-2-(1H-pyrrolo[2,3-b]pyridin-4-yl)pyrimidin-4-yl)-3-methylmorpholine,
(R)-4-(2-(1H-pyrrolo[2,3-b]pyridin-4-yl)-6-(trifluoromethyl)pyrimidin-4-yl)-3-methylmorpholine,
(R)-4-(6-methoxy-2-(1H-pyrrolo[2,3-b]pyridin-4-yl)pyrimidin-4-yl)-3-methylmorpholine,
(R)-6-(3-methylmorpholino)-2-(1H-pyrrolo[2,3-b]pyridin-4-yl)pyrimidin-4-amine,
(R)-6-(3-methylmorpholino)-2-(1H-pyrrolo[2,3-b]pyridin-4-yl)pyrimidine-4-carbonitrile,
(R)-3-methyl-4-(6-(pyridin-3-yl)-2-(1H-pyrrolo[2,3-b]pyridin-4-yl)pyrimidin-4-yl)morpholine,
(R)-4-(6-(4,4-difluoropiperidin-1-yl)-2-(1H-pyrrolo[2,3-b]pyridin-4-yl)pyrimidin-4-yl)-3-methylmorpholine,
(R)-6-(3-methylmorpholino)-2-(1H-pyrrolo[2,3-b]pyridin-4-yl)-N-(2,2,2-trifluoroethyl)pyrimidin-4-amine, (R)-4-(6-(tert-butyl)-2-(1H-pyrrolo[2,3-b]pyridin-4-yl)pyrimidin-4-yl)-3-methylmorpholine,
(R)-3-methyl-4-(6-phenyl-2-(1H-pyrrolo[2,3-b]pyridin-4-yl)pyrimidin-4-yl)morpholine,
(R)-4-(6-(2-fluoropropan-2-yl)-2-(1H-pyrrolo[2,3-b]pyridin-4-yl)pyrimidin-4-yl)-3-methylmorpholine,
(R)-4-(6-cyclopropyl-2-(1H-pyrrolo[2,3-b]pyridin-4-yl)pyrimidin-4-yl)-3-methylmorpholine,
(R)-4-(6-cyclobutyl-2-(1H-pyrrolo[2,3-b]pyridin-4-yl)pyrimidin-4-yl)-3-methylmorpholine,
(R)-4-(6-cyclopentyl-2-(1H-pyrrolo[2,3-b]pyridin-4-yl)pyrimidin-4-yl)-3-methylmorpholine,
(R)-4-(6-cyclohexyl-2-(1H-pyrrolo[2,3-b]pyridin-4-yl)pyrimidin-4-yl)-3-methylmorpholine,
(R)-2-methyl-2-(6-(3-methylmorpholino)-2-(1H-pyrrolo[2,3-b]pyridin-4-yl)pyrimidin-4-yl)propenamide,
(R)-2-methyl-2-(6-(3-methylmorpholino)-2-(1H-pyrrolo[2,3-b]pyridin-4-yl)pyrimidin-4-yl)propanoic acid,
(R)-4-(6-(1-methoxy-2-methylpropan-2-yl)-2-(1H-pyrrolo[2,3-b]pyridin-4-yl)pyrimidin-4-yl)-3-methylmorpholine,
(R)—N-cyclopropyl-6-(3-methylmorpholino)-2-(1H-pyrrolo[2,3-b]pyridin-4-yl)pyrimidin-4-amine,
(R)-3-methyl-4-(6-(4-methylpiperazin-1-yl)-2-(1H-pyrrolo[2,3-b]pyridin-4-yl)pyrimidin-4-yl)morpholine,
(R)-4-(6-(3,3-difluoropyrrolidin-1-yl)-2-(1H-pyrrolo[2,3-b]pyridin-4-yl)pyrimidin-4-yl)-3-methylmorpholine,
N-((3,3-difluorocyclopentyl)methyl)-6-((R)-3-methylmorpholino)-2-(1H-pyrrolo[2,3-b]pyridin-4-yl)pyrimidin-4-amine,
(R)-6-(3-methylmorpholino)-N-(2-morpholinoethyl)-2-(1H-pyrrolo[2,3-b]pyridin-4-yl)pyrimidin-4-amine,
(R)-4-(6-(1-(4,4-difluoropiperidin-1-yl)-2-methylpropan-2-yl)-2-(1H-pyrrolo[2,3-b]pyridin-4-yl)pyrimidin-4-yl)-3-methylmorpholine,
(R)-4-(6-(1-(2-methoxyethoxy)-2-methylpropan-2-yl)-2-(1H-pyrrolo[2,3-b]pyridin-4-yl)pyrimidin-4-yl)-3-methylmorpholine,
(R)-4-(2-(1H-pyrrolo[2,3-b]pyridin-4-yl)-6-(6-(trifluoromethyl)pyridin-3-yl)pyrimidin-4-yl)-3-methylmorpholine,
(R)-5-(6-(3-methylmorpholino)-2-(1H-pyrrolo[2,3-b]pyridin-4-yl)pyrimidin-4-yl)pyridin-2-amine,
(R)—N,N-dimethyl-2-(2-methyl-2-(6-(3-methylmorpholino)-2-(1H-pyrrolo[2,3-b]pyridin-4-yl)pyrimidin-4-yl)propoxy)ethan-1-amine,
(R)-1-(6-(3-methylmorpholino)-2-(1H-pyrrolo[2,3-b]pyridin-4-yl)pyrimidin-4-yl)cyclopropan-1-ol,
(R)-1-(6-(3-methylmorpholino)-2-(1H-pyrrolo[2,3-b]pyridin-4-yl)pyrimidin-4-yl)cyclopropane-1-carbonitrile,
(R)-1-(6-(3-methylmorpholino)-2-(1H-pyrrolo[2,3-b]pyridin-4-yl)pyrimidin-4-yl)cyclopropan-1-amine,
(3R)-4-(6-(2,2-difluorocyclopropyl)-2-(1H-pyrrolo[2,3-b]pyridin-4-yl)pyrimidin-4-yl)-3-methylmorpholine,
(R)-4-(6-(1-fluorocyclopropyl)-2-(1H-pyrrolo[2,3-b]pyridin-4-yl)pyrimidin-4-yl)-3-methylmorpholine,
(R)-4-(6-(3,3-difluorocyclobutyl)-2-(1H-pyrrolo[2,3-b]pyridin-4-yl)pyrimidin-4-yl)-3-methylmorpholine,
(R)-1-methyl-3-(6-(3-methylmorpholino)-2-(1H-pyrrolo[2,3-b]pyridin-4-yl)pyrimidin-4-yl)cyclobutan-1-ol,
(R)-1-methyl-3-(6-(3-methylmorpholino)-2-(1H-pyrrolo[2,3-b]pyridin-4-yl)pyrimidin-4-yl)cyclobutane-1-carbonitrile,
(R)-1-(6-(3-methylmorpholino)-2-(1H-pyrrolo[2,3-b]pyridin-4-yl)pyrimidin-4-yl)cyclobutan-1-amine.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkyl-carbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^X$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as (C$_{1-4}$) alkyl halides, e.g., methyl, ethyl, iso-propyl and tert-butyl chlorides, bromides and iodides; di-(C$_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl (C$_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide (H$_2$O$_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS 15 (20-50%), Vitamin E TPGS, and d-α-tocopheryl PEG 1000 succinate (20-50%), using complexation such as HPβCD and SBEP3CD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)$NR_aR_b$ where $R_a$ and $R_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —$NO_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(AA1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB 1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6 KB 1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES 1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors(HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), drug-antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, antimetabolites, topoisomerase inhibitors, anti-microtubule agents, kinase inhibitors, epigenetic agents, HSP90 inhibitors, PARP inhibitors, BCL-2 inhibitor, drug-antibody conjugate, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

In certain embodiments, the compounds of the invention are administered in combination with one or more anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate. Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates. The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

In certain embodiments, the compounds of the invention are administered in combination with one or more immunosuppressant agents.

In some embodiments, the immunosuppressant agent is glucocorticoid, methotrexate, cyclophosphamide, azathioprine, mercaptopurine, leflunomide, cyclosporine, tacrolimus, and mycophenolate mofetil, dactinomycin, anthracyclines, mitomycin C, bleomycin, or mithramycin, or fingolimod.

The invention further provides methods for the prevention or treatment of a neoplastic disease, autoimmune and/or inflammatory disease. In one embodiment, the invention relates to a method of treating a neoplastic disease, autoimmune and/or inflammatory disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease, autoimmune and/or inflammatory disease.

In one embodiment, the neoplastic disease is a B-cell malignancy includes but not limited to B-cell lymphoma, lymphoma (including Hodgkin's lymphoma and non-Hodgkin's lymphoma), hairy cell lymphoma, small lymphocytic lymphoma (SLL), mantle cell lymphoma (MCL), and diffuse large B-cell lymphoma (DLBCL), multiple myeloma, chronic and acute myelogenous leukemia and chronic and acute lymphocytic leukemia.

The autoimmune and/or inflammatory diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barré syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize the Formula (I) compounds in which A is

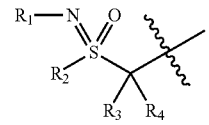

is described in Scheme A. $R_1$, $R_2$, $R_3$, $R_4$, $R_5$, $R_6$, $R_7$, $R_8$, and W in general Scheme A are the same as those described in the Summary section above.

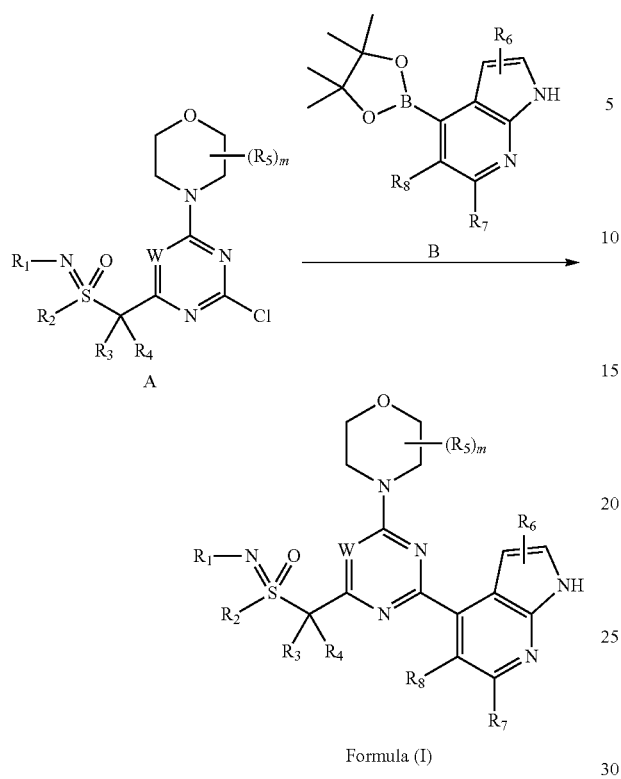

Formula (I)

Formula (I) can be prepared from intermediate A, by reaction with intermediate B, in the presence of a suitable Pd catalyst and phosphine ligand in a suitable solvent such as a mixture of N,N-dimethylformamide, dimethoxyethane, water and ethanol, under suitable conditions such as heating in a microwave reactor. Alternatively, Intermediate C may be prepared from intermediate A, by reaction with intermediate B, with a suitable base such as NaH, $Na_2CO_3$, $Cs_2CO_3$ or $K_2CO_3$ in a suitable solvent such as N,N-dimethylformamide or N,N-dimethylacetamide or in the presence of a suitable Pd catalyst and phosphine ligand in a suitable solvent such as dioxane.

Intermediate B can be prepared by the following Scheme B:

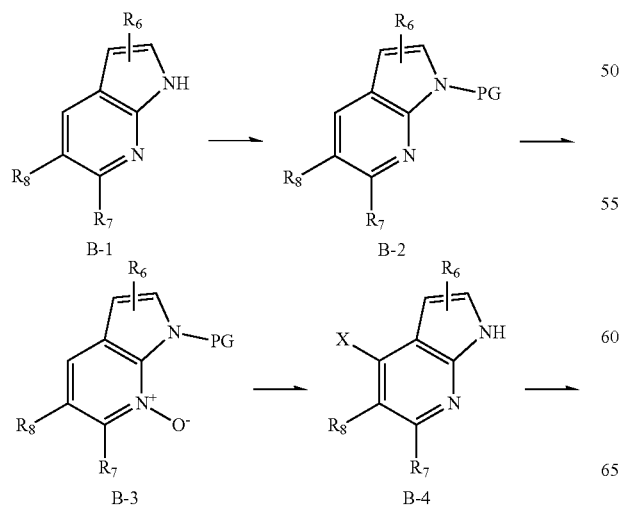

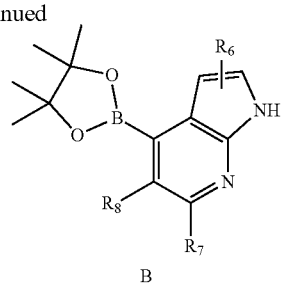

B

In Scheme B, the commercially starting material B-1 can undergo a protecting process to obtain the intermediate B-2, which can be oxidized to form the N-oxide. After that B-3 can undergo a halogenation reaction (e.g bromination or chlorination) followed by the reduction of N-oxide, followed by a de-protecting progress to form the halo intermediate B-4. Finally, B-4 can be converted to the boronic acid or ester intermediate B using conditions well known in the art.

Intermediate A in which $R_1$ is H; $R_3$ and $R_4$ together is a cycloalkyl can be prepared by the following Scheme C. $R_2$, $R_5$, m, Q and W in general Scheme A are the same as those described in the Summary section above; n is 0, 1, 2, or 3.

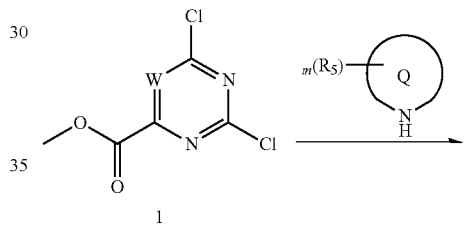

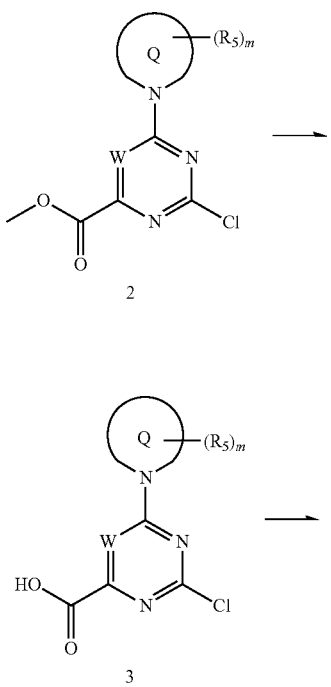

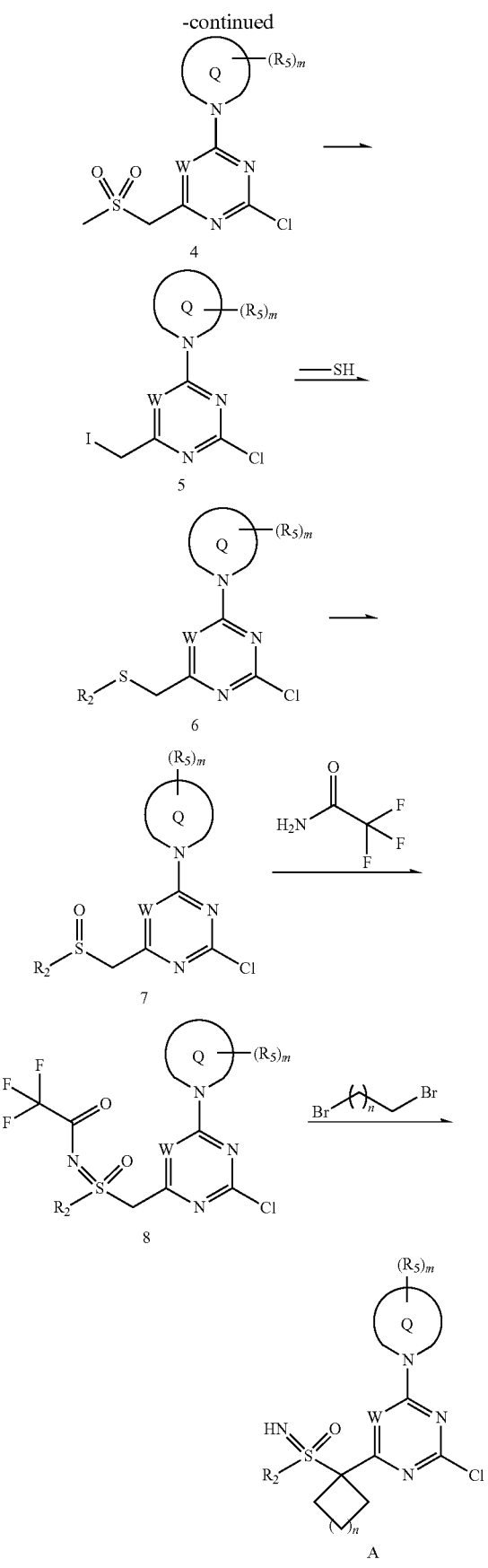

In Scheme C, the intermediate 2 can be prepared by the reaction of the appropriate starting material 1 with the appropriate cyclic amine in the presence of a suitable base such as triethylamine in a suitable solvent such as DCM. After that, the intermediate 2 can be converted to 3, then to 4, then to 5 using conditions well known in the art. The intermediate 6 may be prepared by the reaction of intermediate 5 with $CH_3SH$ in the presence of a suitable base such as triethylamine and a solvent such as N,N-dimethylformamide. After that intermediate 6 can be oxidized to from intermediate 7, which can react with 2,2,2-trifluoroacetamide to form the intermediate 8. Finally, 8 can react with 1,2-dibromoethane followed by a de-protecting process to form the intermediate A.

Intermediate A in which $R_1$ is alkyl; $R_3$ and $R_4$ together is a cycloalkyl can be prepared by the following Scheme D. $R_2$, $R_5$, m, Q and W in general Scheme A are the same as those described in the Summary section above; n is 0, 1, 2, or 3.

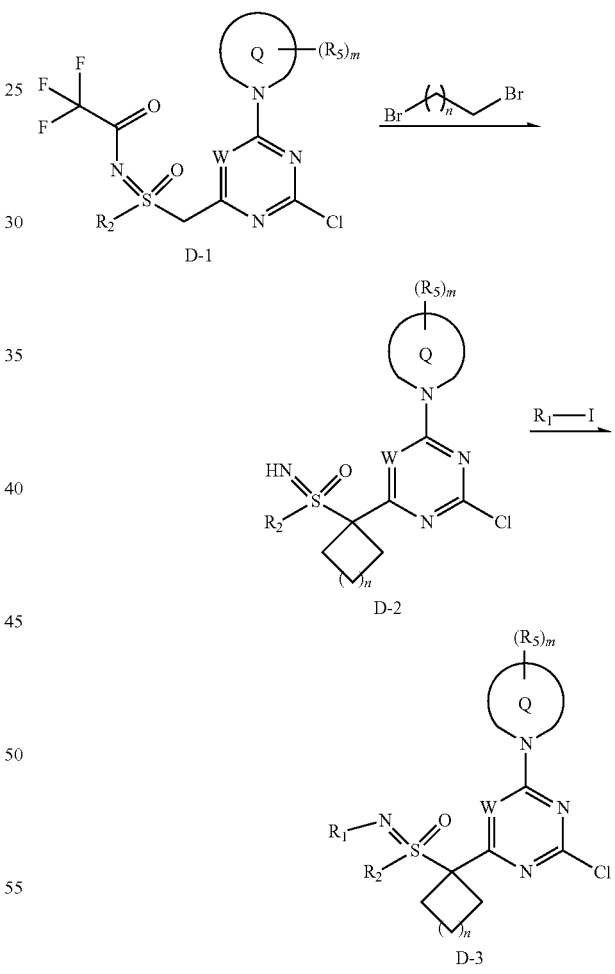

In Scheme D, the intermediate D-1 can react with dibromide to form the intermediate D-2, which can further react with appropriate alkyliodide to yield the target intermediates.

Other intermediate A with different substituted groups can be made by the method similar to Scheme C, by using different starting material and reagents.

A typical approach to synthesize the Formula (I) compounds in which A is H is

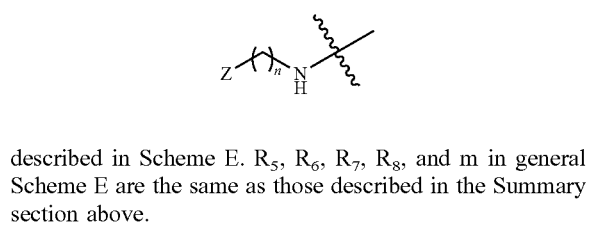

described in Scheme E. $R_5$, $R_6$, $R_7$, $R_8$, and m in general Scheme E are the same as those described in the Summary section above.

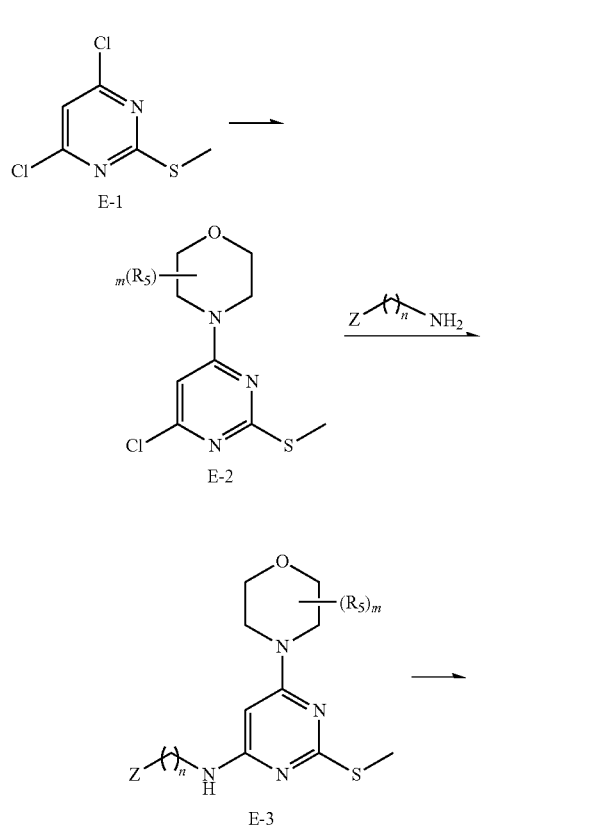

In Scheme E, the staring material 4,6-dichloro-2-(methylthio)pyrimidine can react with substituted morpholine to form the intermediate E-2, which can react with appropriate amine to obtain E-3. Finally, the coupling of E-3 with intermediate B can yield the target compounds.

A typical approach to synthesize the Formula (I) compounds in which A is is described in Scheme F. $R_5$, $R_6$, $R_7$, $R_8$, and m in general Scheme E are the same as those described in the Summary section above.

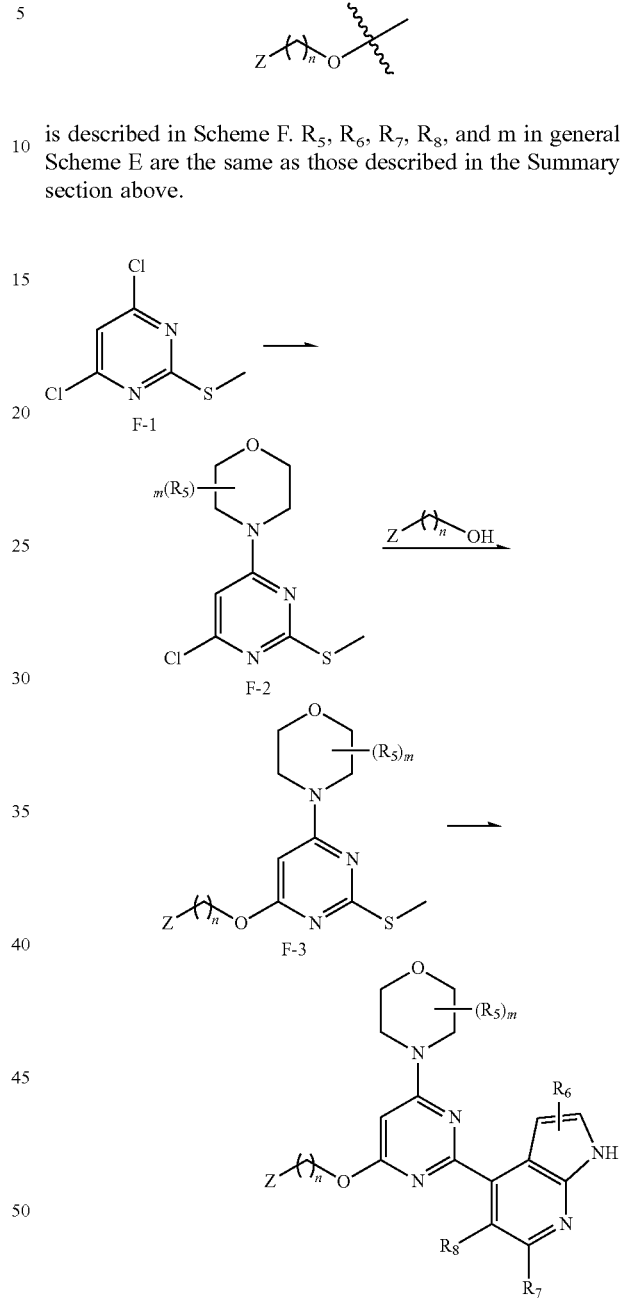

In Scheme F, the staring material 4,6-dichloro-2-(methylthio)pyrimidine can react with substituted morpholine to form the intermediate F-2, which can react with appropriate alcohol to obtain F-3. Finally, the coupling of F-3 with intermediate B can yield the target compounds.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example CY-202: Preparation of (1-(5-chloro-6-((R)-3-methylmorpholino)-2-(1H-pyrrolo[2,3-b]pyridin-4-yl)pyrimidin-4-yl)cyclopropyl)(imino)(methyl)-l6-sulfanone Synthesis of 5-chloro-6-(chloromethyl)-1,2,3,4-tetrahydropyrimidine-2,4-dione: Into a 1-L round-bottom flask, was placed 6-(chloromethyl)-1,2,3,4-tetrahydropyrimidine-2,4-dione (15 g, 93.42 mmol, 1 equiv), acetic acid (225 mL), acetyl acetate (15 mL). The resulting solution was stirred for 30 min at 80° C. in an oil bath. Then NCS (16.2 g, 121.32 mmol, 1.30 equiv) was added at 60° C. The resulting solution was stirred for 3 h at 60° C. in an oil bath. The reaction was then quenched by the addition of 500 mL of water/ice. The solids were collected by filtration. The solid was dried in an oven under reduced pressure. This resulted in 10.1 g of 5-chloro-6-(chloromethyl)-1,2,3,4-tetrahydropyrimidine-2,4-dione as an off-white solid. LC-MS-BLV-CY-202-1: (ES, m/z): 195[M+H]$^+$. H-NMR-BLV-CY-202-1: (300 MHz, DMSO, ppm): δ 11.71 (s, 1H), 11.56 (s, 1H), 4.47 (s, 2H).

Synthesis of 5-chloro-6-[(methylsulfanyl)methyl]-1,2,3,4-tetrahydropyrimidine-2,4-dione: Into a 250-mL round-bottom flask, was placed 5-chloro-6-(chloromethyl)-1,2,3,4-tetrahydropyrimidine-2,4-dione (7.75 g, 39.74 mmol, 1 equiv), DMF (40 mL, 0.55 mmol, 0.01 equiv), NaSCH$_3$ (7.34 g, 104.86 mmol, 2.64 equiv). The resulting solution was stirred for 18 hr at room temperature. The resulting mixture was diluted with 100 mL of EA and the solids were collected by filtration. This resulted in 8.65 g (crude) of 5-chloro-6-[(methylsulfanyl)methyl]-1,2,3,4-tetrahydropyrimidine-2,4-dione as a yellow solid. LC-MS-BLV-CY-202-2: (ES, m/z): 207[M+H]$^+$. H-NMR-BLV-CY-202-2: (300 MHz, DMSO, ppm): δ 11.55 (s, 1H), 11.27 (s, 1H), 3.55 (s, 2H), 2.15 (s, 3H).

Synthesis of 2,4,5-trichloro-6-[(methylsulfanyl)methyl]pyrimidine: Into a 500-mL round-bottom flask, was placed 5-chloro-6-[(methylsulfanyl)methyl]-1,2,3,4-tetrahydropyrimidine-2,4-dione (8.65 g, 41.86 mmol, 1 equiv), phosphoryl trichloride (100 mL, 1.07 mol, 25 equiv). The resulting solution was stirred for 3 hr at 100° C. in an oil bath. The resulting mixture was concentrated. The residue was diluted with 500 mL of EA and then quenched by the addition of 1 L of water/ice. The pH value of the solution was adjusted to 8-9 with aq. NaHCO$_3$. The resulting solution was extracted with 3×500 ml of ethyl acetate. The resulting EA layer was concentrated and the residue was applied onto a silica gel column with ethyl acetate/petroleum ether (PE). This resulted in 4.4 g (43.16%) of 2,4,5-trichloro-6-[(methylsulfanyl)methyl]pyrimidine as a yellow solid. LC-MS-BLV-CY-202-3: (ES, m/z): 243[M+H]$^+$. H-NMR-BLV-CY-202-3: (300 MHz, CDCl$_3$, ppm): δ 3.82 (s, 2H), 2.19 (s, 3H).

Synthesis of 2,4,5-trichloro-6-(methanesulfinylmethyl)pyrimidine: Into a 500-mL round-bottom flask, was placed 2,4,5-trichloro-6-[(methylsulfanyl)methyl]pyrimidine (4 g, 16.43 mmol, 1 equiv), EA (100 mL), H$_2$O (50 mL), MeOH (50 mL), sodium periodate (4.28 g, 20.01 mmol, 1.22 equiv). The resulting solution was stirred for 15 hr at room temperature. The solids were filtered out. The resulting mixture was concentrated. The residue was applied onto a silica gel column with ethyl acetate/petroleum ether (1/3-1/1). This resulted in 4.1 g (96.18%) of 2,4,5-trichloro-6-(methanesulfinylmethyl)pyrimidine as an off-white solid. LC-MS-BLV-CY-202-4: (ES, m/z): 259[M+H]$^+$ Synthesis of (3R)-4-[2,5-dichloro-6-(methanesulfinylmethyl)pyrimidin-4-yl]-3-methylmorpholine: Into a 250-mL round-bottom flask, was placed 2,4,5-trichloro-6-(methanesulfinylmethyl)pyrimidine (3.1 g, 11.94 mmol, 1 equiv), DCM (150 mL), TEA (1.58 g, 15.61 mmol, 1.31 equiv), (3R)-3-methylmorpholine (1.21 g, 11.96 mmol, 1.00 equiv). The resulting solution was stirred for 15 hr at room temperature. The resulting mixture was concentrated. The residue was applied onto a silica gel column with ethyl acetate/petroleum ether (1/3-1/1). This resulted in 2.1 g (54.23%) of (3R)-4-[2,5-dichloro-6-(methanesulfinylmethyl)pyrimidin-4-yl]-3-methylmorpholine as yellow oil. LC-MS-BLV-CY-202-41: (ES, m/z): 324[M+H]$^+$. H-NMR-BLV-CY-202-41: (300 MHz, CDCl$_3$, ppm): δ 4.57 (s, 1H), 4.33 (t, J=12.6 Hz, 1H), 4.17 (t, J=11.4 Hz, 2H), 3.94 (d, J=9.6 Hz, 1H), 3.72 (s, 2H), 3.47-3.67 (m, 2H), 2.76 (s, 3H), 1.44 (d, J=6.9 Hz, 3H).

Synthesis of N-[([2,5-dichloro-6-[(3R)-3-methylmorpholin-4-yl]pyrimidin-4-yl]methyl)(methyl)oxo-lambda6-sulfanylidene]-2,2,2-trifluoroacetamide Into a 50-mL round-bottom flask purged and maintained with an inert atmosphere of nitrogen, was placed (3R)-4-[2,5-dichloro-6-(methanesulfinylmethyl)pyrimidin-4-yl]-3-methylmorpholine (500 mg, 1.54 mmol, 1 equiv), DCM (20 mL), trifluoroacetamide (350 mg, 3.10 mmol, 2.01 equiv), oxomagnesium (249 mg, 6.18 mmol, 4.01 equiv), 1,1,1-tris(acetyloxy)dirhodium-1-yl acetate (17 mg, 0.04 mmol, 0.02 equiv), PhI(AcO)$_2$ (496 mg, 1.55 mmol, 1.00 equiv). The resulting solution was stirred for 15 hr at room temperature. Then trifluoroacetamide (87 mg), PhI(AcO)$_2$ (125 mg), oxomagnesium (62 mg), 1,1,1-tris(acetyloxy)dirhodium-1-yl acetate (4.1 mg) was added. The resulting solution was stirred for 15 hr at room temperature. The solids were filtered out. The resulting mixture was concentrated and applied onto a silica gel column with ethyl acetate/petroleum ether (1/10). This resulted in 490 mg (73.0%) of N-[([2,5-dichloro-6-[(3R)-3-methylmorpholin-4-yl]pyrimidin-4-yl]methyl)(methyl)oxo-lambda6-sulfanylidene]-2,2,2-trifluoroacetamide as yellow oil. LC-MS-BLV-CY-202-42: (ES, m/z): 435[M+H]$^+$. H-NMR-BLV-CY-202-42: (300 MHz, CDCl$_3$, ppm): δ 4.58 (s, 1H), 4.34 (t, J=12.0 Hz, 1H), 4.10-4.30 (m, 2H), 3.94 (d, J=9.6 Hz, 1H), 3.72 (s, 2H), 3.46-3.69 (m, 2H), 2.78 (s, 3H), 1.45 (d, J=6.0 Hz, 3H).

Synthesis of (1-[2,5-dichloro-6-[(3R)-3-methylmorpholin-4-yl]pyrimidin-4-yl]cyclopropyl)(imino)methyl-lambda6-sulfanone. Into a 50-mL round-bottom flask, was placed N-[([2,5-dichloro-6-[(3R)-3-methylmorpholin-4-yl]pyrimidin-4-yl]methyl)(methyl)oxo-lambda6-sulfanylidene]-2,2,2-trifluoroacetamide (300 mg, 0.69 mmol, 1 equiv), 2-MeTHF (25 mL), 1,2-dibromoethane (518.7 mg, 2.76 mmol, 4.01 equiv), sodium hydroxide (1.66 g, 41.50 mmol, 60.21 equiv), (C$_8$H$_{17}$)$_4$NBr (38 mg, 0.07 mmol, 0.10 equiv). The resulting solution was stirred for 3 hr at 60° C. in an oil bath. The resulting solution was extracted with 2×10 ml of ethyl acetate and the organic layers combined and concentrated. The crude product was purified by Flash-Prep-HPLC with the following conditions (IntelFlash-1): Column, C18 silica gel; mobile phase, 0.05%

NH$_3$.H$_2$O=25% increasing to 0.05% NH$_3$.H$_2$O=30%; Detector, 254 nm&220 nm. This resulted in 30 mg (11.92%) of (1-[2,5-dichloro-6-[(3R)-3-methylmorpholin-4-yl]pyrimidin-4-yl]cyclopropyl)(imino)methyl-lambda6-sulfanone as a yellow solid. LC-MS-BLV-CY-202-43: (ES, m/z): 365[M+H]$^+$. H-NMR-BLV-CY-202-43: (300 MHz, CDCl$_3$, ppm): δ 4.54 (s, 1H), 4.07-4.15 (m, 1H), 3.92-4.07 (m, 1H), 3.72 (s, 2H), 3.51-3.67 (m, 2H), 3.10 (s, 3H), 2.59 (s, 1H), 1.94-2.02 (m, 1H), 1.73-1.80 (m, 1H), 1.42 (m, 5H).

Synthesis of (1-[5-chloro-6-[(3R)-3-methylmorpholin-4-yl]-2-[1H-pyrrolo[2,3-b]pyridin-4-yl]pyrimidin-4-yl]cyclopropyl)(imino)methyl-lambda6-sulfanone Into a 50-mL round-bottom flask purged and maintained with an inert atmosphere of nitrogen, was placed (1-[2,5-dichloro-6-[(3R)-3-methylmorpholin-4-yl]pyrimidin-4-yl]cyclopropyl) (imino)methyl-lambda6-sulfanone (25 mg, 0.07 mmol, 1 equiv), DME (4 mL), water (1 mL), 4-(4,4,5,5-tetramethyl-1,3,2-dioxaborolan-2-yl)-1H-pyrrolo[2,3-b]pyridine (16.7 mg, 0.07 mmol, 1.00 equiv), dichloropalladium; bis(triphenylphosphane) (4.8 mg, 0.01 mmol, 0.10 equiv), Na$_2$CO$_3$ (14.5 mg, 0.14 mmol, 1.98 equiv). The resulting solution was stirred for 2 hr at 90° C. in an oil bath. The crude product (was purified by Flash-Prep-HPLC with the following conditions (IntelFlash-1): Column, C18 silica gel; mobile phase, 0.05% NH$_3$.H$_2$O/CH$_3$CN=35% increasing to 40%; Detector, 254 nm&220 nm. This resulted in 5.0 mg (16.35%) of (1-[5-chloro-6-[(3R)-3-methylmorpholin-4-yl]-2-[1H-pyrrolo[2,3-b]pyridin-4-yl]pyrimidin-4-yl]cyclopropyl)(imino)methyl-lambda6-sulfanone as a light yellow solid. LC-MS-BLV-CY-202-0: (ES, m/z): 447[M+H]$^+$. H-NMR-BLV-CY-202-0: (300 MHz, CD$_3$OD, ppm): δ 8.34 (d, J=4.8 Hz, 1H), 8.15 (d, J=5.4 Hz, 1H), 7.58 (s, 1H), 7.45 (s, 1H), 4.61 (s, 1H), 3.99-4.11 (m, 2H), 3.64-3.86 (m, 4H), 3.32 (s, 3H), 1.81-2.08 (m, 2H), 1.63 (m, 2H), 1.48 (m, 3H).

Example CY-200-1: Preparation of Methyl[methyl (1-[6-[(3R)-3-methylmorpholin-4-yl]-2-[1H-pyrrolo [2,3-b]pyridin-4-yl]pyrimidin-4-yl]cyclopropyl)oxo-lambda-sulfanylidene]amine Synthesis of methyl (R)-2-chloro-6-(3-methylmorpholino)pyrimidine-4-carboxylate: Into a 500-mL round-bottom flask, was placed methyl 2,6-dichloropyrimidine-4-carboxylate (10 g, 0.05 mmol, 1 equiv), DCM (200 mL, 2.35 mmol, 48.75 equiv), (3R)-3-methylmorpholine (4.9 g, 0.05 mmol, 1.00 equiv), TEA (6.37 g, 0.06 mmol, 1.30 equiv). The resulting solution was stirred for 18 hr at room temperature. The resulting solution was diluted with 800 mL of H$_2$O and extracted with 4×400 ml of dichloromethane and the resulting mixture was washed with 2×300 ml of brine. The organic layer was concentrated and applied onto a silica gel column with ethyl acetate/petroleum ether (10%). This resulted in 10 g (76.19%) of methyl 2-chloro-6-[(3R)-3-methylmorpholin-4-yl]pyrimidine-4-carboxylate as a yellow solid. LC-MS-BLV-CY-200-1-1: (ES, m/z): 272 [M+H]$^+$. H-NMR-BLV-CY-200-1-1: (300 MHz, d$_6$-DMSO, ppm): δ 7.15 (s, 1H), 4.38 (br s, 1H), 4.11-4.13 (m, 1H), 4.01-4.09 (m, 1H), 3.98 (s, 3H), 3.81 (d, J=11.7 Hz, 1H), 3.70 (d, J=11.7 Hz, 1H), 3.55 (t, J=12.3 Hz, 1H), 3.34 (t, J=12.9 Hz, 1H), 1.35 (d, J=6.9 Hz, 3H).

Synthesis of [2-chloro-6-[(3R)-3-methylmorpholin-4-yl]pyrimidin-4-yl]methanol. Into a 500-mL 3-necked round-bottom flask purged and maintained with an inert atmosphere of nitrogen, was placed methyl 2-chloro-6-[(3R)-3-methylmorpholin-4-yl]pyrimidine-4-carboxylate (10 g, 0.04 mmol, 1 equiv), oxolane (200 mL). This was followed by the addition of LiBH$_4$ in THF (11 mL, 0.6 equiv) dropwise with stirring. The resulting solution was stirred for 18 hr at room temperature. The reaction was then quenched by the addition of 150 mL of water. The resulting solution was extracted with 2×100 ml of ethyl acetate and the EA layer dried over anhydrous sodium sulfate and concentrated. This resulted in 8.97 g (crude) of [2-chloro-6-[(3R)-3-methylmorpholin-4-yl]pyrimidin-4-yl]methanol as a yellow solid. LC-MS-BLV-CY-200-1-2: (ES, m/z): 244 [M+H]$^+$. H-NMR-BLV-CY-200-1-2: (300 MHz, d$_6$-DMSO, ppm): δ 6.44 (s, 1H), 4.60 (s, 2H), 4.32 (br s, 1H), 4.01 (d, J=11.4 Hz, 1H), 3.79 (d, J=11.4 Hz, 1H), 3.69 (d, J=11.7 Hz, 1H), 3.54 (t, J=12.3 Hz, 1H), 3.30 (t, J=13.2 Hz, 1H), 2.38 (br s, 2H), 1.33 (d, J=6.9 Hz, 3H).

Synthesis of [2-chloro-6-[(3R)-3-methylmorpholin-4-yl]pyrimidin-4-yl]methyl methanesulfonate. Into a 500-mL 3-necked round-bottom flask purged and maintained with an inert atmosphere of nitrogen, was placed [2-chloro-6-[(3R)-3-methylmorpholin-4-yl]pyrimidin-4-yl]methanol (8.97 g, 0.04 mmol, 1 equiv), DCM (200 mL), TEA (4.85 g, 0.05 mmol, 1.30 equiv). This was followed by the addition of methanesulfonyl chloride (9.13 g, 0.08 mmol, 2.17 equiv) dropwise with stirring. The resulting solution was stirred for 1 hr at 0° C. in an ice/salt bath. The reaction was then quenched by the addition of 300 mL of water. The resulting solution was extracted with 3×300 ml of dichloromethane. The DCM layer was washed with 2×400 ml of brine, dried by Na$_2$SO$_4$ and concentrated. This resulted in 11 g (92.87%) of [2-chloro-6-[(3R)-3-methylmorpholin-4-yl]pyrimidin-4-yl]methyl methanesulfonate as a yellow solid. LC-MS-BLV-CY-200-1-3: (ES, m/z): 322 [M+H]$^+$. H-NMR-BLV-CY-200-1-3: (300 MHz, d$_6$-DMSO, ppm): δ 6.85 (s, 1H), 5.10 (s, 2H), 4.38 (br, 1H), 3.94 (d, J=11.4 Hz, 1H), 3.72 (d, J=11.7 Hz, 1H), 3.58 (d, J=11.7 Hz, 1H), 3.45 (t, J=12.0 Hz, 1H), 3.18-3.26 (m, 1H), 2.78-2.86 (m, 1H), 2.43 (s, 3H), 1.21 (d, J=6.9 Hz, 3H).

Synthesis of (3R)-4-[2-chloro-6-(iodomethyl)pyrimidin-4-yl]-3-methylmorpholine. Into a 500-mL round-bottom flask, was placed [2-chloro-6-[(3R)-3-methylmorpholin-4-yl]pyrimidin-4-yl]methyl methanesulfonate (14.8 g, 0.05 mmol, 1 equiv), 1,4-dioxane (300 mL), LiI (11.97 g, 0.09 mmol, 1.94 equiv). The resulting solution was stirred for 1 hr at 100° C. in an oil bath. The resulting mixture was cooled and added 400 ml of 20% Na$_2$S$_2$O$_3$ solution. The resulting mixture was extracted with 3×400 ml of ethyl acetate. The organic mixture was dried over anhydrous sodium sulfate. The filtrate was concentrated. The residue was applied onto a silica gel column with ethyl acetate/petroleum ether (9%). This resulted in 7.45 g (45.81%) of (3R)-4-[2-chloro-6-(iodomethyl)pyrimidin-4-yl]-3-methylmorpholine as a yellow solid. H-NMR-BLV-CY-200-1-4: (300 MHz, d$_6$-DMSO, ppm): δ 6.95 (s, 1H), 4.58 (s, 2H), 4.35 (br, 1H), 3.91-4.10 (m, 2H), 3.72 (d, J=11.4 Hz, 1H), 3.59 (d, J=11.4 Hz, 1H), 3.44 (t, J=12.0 Hz, 1H), 3.22 (t, J=13.2 Hz, 1H), 1.21 (d, J=6.9 Hz, 3H).

Synthesis of (3R)-4-[2-chloro-6-[(methylsulfanyl)methyl]pyrimidin-4-yl]-3-methylmorpholine: Into a 250-mL round-bottom flask, was placed (3R)-4-[2-chloro-6-(iodomethyl)pyrimidin-4-yl]-3-methylmorpholine (7.45 g, 21.07 mmol, 1 equiv), N,N-dimethylformamide (50 mL, 0.68 mmol), (methylsulfanyl)sodium (2.83 g, 20.2 mmol, 1 equiv). The resulting solution was stirred for 1 hr at 25° C. The reaction was then quenched by the addition of 150 mL of water/ice. The resulting solution was extracted with 3×50 ml of ethyl acetate. The organic mixture was dried over anhydrous sodium sulfate. The filtrate was concentrated. The residue was applied onto a silica gel column with ethyl acetate/petroleum ether (10%). This resulted in 4.48 g (77.66%) of (3R)-4-[2-chloro-6-[(methylsulfanyl)methyl]pyrimidin-4-yl]-3-methylmorpholine as yellow oil. LC-MS-BLV-CY-200-1-5: (ES, m/z): 274 [M+H]$^+$. H-NMR-BLV-CY-200-1-5: (300 MHz, d$_6$-DMSO, ppm): δ 6.77 (s, 1H), 4.32 (br, 1H), 3.95-4.01 (m, 2H), 3.72 (d, J=11.7 Hz, 1H), 3.61 (s, 1H), 3.54 (s, 2H), 3.39-3.49 (m, 1H), 3.13-3.22 (m, 1H), 2.07 (s, 3H), 1.20 (d, J=6.6 Hz, 3H).

Synthesis of (3R)-4-[2-chloro-6-(methanesulfinylmethyl)pyrimidin-4-yl]-3-methylmorpholine: Into a 250-mL round-bottom flask, was placed (3R)-4-[2-chloro-6-[(methylsulfanyl)methyl]pyrimidin-4-yl]-3-methylmorpholine (4.4 g, 16.07 mmol, 1 equiv), water (15 mL), EA (30 mL), methanol (15 mL), sodium periodate (3.45 g, 16.13 mmol, 1.00 equiv). The resulting solution was stirred for 18 hr at 25° C. The resulting solution was diluted with 80 mL of DCM. The solids were filtered out. The resulting solution was extracted with 3×50 ml of dichloromethane. The organic mixture was dried over anhydrous sodium sulfate. The filtrate was concentrated. The residue was applied onto a silica gel column with methanol/dichloromethane (0-7%). This resulted in 3.0 g (64.42%) of (3R)-4-[2-chloro-6-(methanesulfinylmethyl)pyrimidin-4-yl]-3-methylmorpholine as a off-white solid. LC-MS-BLV-CY-200-1-6: (ES, m/z): 290 [M+H]$^+$. H-NMR-BLV-CY-200-1-6: (300 MHz, d$_6$-DMSO, ppm): δ 6.81 (s, 1H), 4.32 (br, 1H), 4.08 (d, J=12.3 Hz, 1H), 3.89-4.00 (m, 3H), 3.72 (d, J=14.4 Hz, 1H), 3.59 (d, J=11.7 Hz, 1H), 3.44 (t, J=12.0 Hz, 1H). 3.20 (t, J=11.1 Hz, 1H), 2.64 (s, 3H), 1.21 (d, J=6.6 Hz, 3H).

Synthesis of N-[([2-chloro-6-[(3R)-3-methylmorpholin-4-yl]pyrimidin-4-yl]methyl)(methyl)oxo-lambda6-sulfanylidene]-2,2,2-trifluoroacetamide: Into a 250-mL round-bottom flask, was placed (3R)-4-[2-chloro-6-(methanesulfinylmethyl)pyrimidin-4-yl]-3-methylmorpholine (2.9 g, 10.01 mmol, 1 equiv), DCM (95 mL), trifluoroacetamide (2.27 g, 20.08 mmol, 2.01 equiv), PhI(AcO)$_2$ (3.23 g, 10.03 mmol, 1.00 equiv), oxomagnesium (1.6 g, 39.70 mmol, 3.97 equiv), 1,1,1-tris(acetyloxy)dirhodium-1-yl acetate (0.11 g, 0.25 mmol, 0.02 equiv). The resulting solution was stirred for 18 hr at room temperature. Then more trifluoroacetamide (0.57 g), PhI(AcO)$_2$ (0.81g), oxomagnesium (0.4 g), 1,1,1-tris(acetyloxy)dirhodium-1-yl acetate (27 mg) was added. The resulting solution was stirred for another 18 hr at room temperature. The solids were filtered out. The resulting mixture was concentrated. The residue was applied onto a silica gel column with ethyl acetate/petroleum ether (20%). This resulted in 2.6 g (64.82%) of N-[([2-chloro-6-[(3R)-3-methylmorpholin-4-yl]pyrimidin-4-yl]methyl)(methyl)oxo-lambda6-sulfanylidene]-2,2,2-trifluoroacetamide as a light yellow solid. LC-MS-BLV-CY-200-1-7: (ES, m/z): 401 [M+H]$^+$. H-NMR-BLV-CY-200-1-7: (300 MHz, CD$_3$Cl, ppm): δ 6.48 (s, 1H), 4.84 (dd, J=5.4 Hz, 13.5 Hz, 1H), 4.65 (d, J=13.8 Hz, 1H), 4.20-4.40 (br, 1H), 4.01 (d, J=11.4 Hz, 2H), 3.75 (d, J=11.4 Hz, 1H), 3.62-3.70 (m, 1H), 3.47-3.57 (m, 1H), 3.42 (s, 3H), 3.25-3.37 (m, 1H), 1.34 (d, J=6.9 Hz, 3H).

Synthesis of (1-[2-chloro-6-[(3R)-3-methylmorpholin-4-yl]pyrimidin-4-yl]cyclopropyl)(imino)methyl-lambda6-sulfanone: Into a 50-mL round-bottom flask purged and maintained with an inert atmosphere of nitrogen, was placed N-[([2-chloro-6-[(3R)-3-methylmorpholin-4-yl]pyrimidin-4-yl]methyl)(methyl)oxo-lambda6-sulfanylidene]-2,2,2-trifluoroacetamide (400 mg, 1.00 mmol, 1 equiv), 2-MeTHF (15 mL), 1,2-dibromoethane (939 mg, 5.00 mmol, 5.01 equiv), (C$_8$H$_{17}$)$_4$NBr (54.7 mg, 0.1 equiv), 10% NaOH (10.0 mmol, 10.0 equiv). The resulting solution was stirred for 2 hr at 60° C. in an oil bath. The crude product was purified by Flash-Prep-HPLC with the following conditions (Intel-Flash-1): Column, C18 silica gel; mobile phase, 0.5% NH$_3$.H$_2$O=52% increasing to 0.5% NH$_3$.H$_2$O=56%; Detector, 254 nm&220 nm. This resulted in 130 mg (39.37%) of (1-[2-chloro-6-[(3R)-3-methylmorpholin-4-yl]pyrimidin-4-yl]cyclopropyl)(imino)methyl-lambda6-sulfanone as a yellow solid. LC-MS-BLV-CY-200-1-8: (ES, m/z): 331 [M+H]$^+$. H-NMR-BLV-CY-200-1-8: (300 MHz, d$_6$-DMSO, ppm): δ 6.95 (s, 1H), 4.37 (br, 1H), 4.04-4.31 (m, 1H), 3.90-3.99 (m, 1H), 3.54-3.83 (m, 4H), 3.01 (s, 3H), 1.63-1.66 (m, 1H), 1.24-1.43 (m, 4H), 1.19 (d, J=6.6 Hz, 3H).

Synthesis of [(1-[2-chloro-6-[(3R)-3-methylmorpholin-4-yl]pyrimidin-4-yl]cyclopropyl)(methyl)oxo-lambda-sulfanylidene](methyl)amine: Into a 50-mL 3-necked round-bottom flask was placed a solution of (1-[2-chloro-6-[(3R)-3-methylmorpholin-4-yl]pyrimidin-4-yl]cyclopropyl)(imino)methyl-lambda-sulfanone (150 mg, 0.45 mmol, 1 equiv) in DMF (6 mL) with string at 0° C. To this solution was added NaH (16.3 mg, 0.68 mmol, 1.50 equiv) and stirred for 5 min at 0° C. To the mixture was added iodomethane (160.9 mg, 1.13 mmol, 2.5 equiv) and stirred for 20 min at room temperature. The crude product was purified by Prep-HPLC. This resulted in 100 mg [(1-[2-chloro-6-[(3R)-3-methylmorpholin-4-yl]pyrimidin-4-yl]cyclopropyl)(methyl)oxo-lambda-sulfanylidene](methyl)amine as yellow oil (64%). LC-MS-BLV-CY-200-1-9: (ES, m/z): 345 [M+H]$^+$. $^1$H-NMR-PH-BLV-CY-200-1-9: (300 MHz, d$_6$-DMSO, ppm): 67.06 (s, 0.5H), 7.03 (s, 0.5H), 4.37 (br, 1H), 4.02-4.07 (m, 1H), 3.94 (d, J=11.7 Hz, 1H), 3.71-3.74 (m, 1H), 3.59 (d, J=11.7 Hz, 1H), 3.46 (td, J=12.0, 0.9 Hz, 1H), 3.19 (t, J=12 Hz, 1H), 3.09 (s, 3H), 2.61 (s, 3H), 1.68-1.75 (m, 1H), 1.52-1.62 (m, 1H), 1.37-1.45 (m, 1H), 1.25-1.34 (m, 1H), 1.21 (d, J=6.9 Hz, 3H), Synthesis of methyl[methyl(1-[6-[(3R)-3-methylmorpholin-4-yl]-2-[1H-pyrrolo[2,3-b]pyridin-4-yl]pyrimidin-4-yl]cyclopropyl)oxo-lambda-sulfanylidene]amine: Into a 25-mL round-bottom flask purged and maintained with an inert atmosphere of nitrogen, was placed [(1-[2-chloro-6-[(3R)-3-methylmorpholin-4-yl]pyrimidin-4-yl]cyclopropyl)(methyl)oxo-lambda-sulfanylidene](methyl)amine (100 mg, 0.29 mmol, 1 equiv), 4-(4,4,5,5-tetramethyl-1,3,2-dioxaborolan-2-yl)-1H-pyrrolo[2,3-b]pyridine (106.2 mg, 0.44 mmol, 1.50 equiv), Pd(PPh$_3$)$_2$Cl$_2$ (20.4 mg, 0.03 mmol, 0.1 equiv), Na$_2$CO$_3$ (76.8 mg, 0.72 mmol, 2.50 equiv), DME (8 mL), H$_2$O (2 mL). The resulting solution was stirred for 30 min at 90° C. The resulting mixture was concentrated and the crude product was purified by Prep-HPLC. This resulted in 41 mg (33%) of methyl[methyl(1-[6-[(3R)-3-methylmorpholin-4-yl]-2-[1H-pyrrolo[2,3-b]pyridin-4-yl]pyrimidin-4-yl]cyclopropyl)oxo-lambda-sulfanylidene]amine as a white solid. LC-MS-BLV-CY-200-1-0: (ES, m/z): 427 [M+H]$^+$. H-NMR-PH-BLV-CY-200-1-0: (300 MHz, d$_6$-DMSO, ppm): 611.80 (s, 1H), 8.34 (d, J=5.1 Hz, 1H), 7.96 (d, J=5.1 Hz, 1H), 7.60 (m, 1H), 7.22 (s, 1H), 7.10 (s, 0.5H), 7.06 (s, 0.5H), 4.57 (br, 1H), 4.17-4.30 (m, 1H), 4.02 (d, J=10.8 Hz, 1H), 3.79-3.83 (m, 1H), 3.68 (d, J=10.8 Hz, 1H), 3.53 (t, J=11.7 Hz, 1H), 3.24-3.29 (m, 1H), 3.18 (s, 3H), 2.66 (s, 3H), 1.78-1.88 (m, 1H), 1.65-1.75 (m, 1H), 1.39-1.54 (m, 2H), 1.25-1.30 (m, 3H).

Example CY-205: Preparation of Methyl[methyl(1-[6-[(3R)-3-methylmorpholin-4-yl]-2-[1H-pyrrolo[2,3-b]pyridin-4-yl]pyrimidin-4-yl]cyclobutyl)oxo-lambda6-sulfanylidene]amine Synthesis of 6-[(methylsulfanyl)methyl]-1,2,3,4-tetrahydropyrimidine-2,4-dione: Into a 500-mL round-bottom flask, was placed 6-(chloromethyl)-1,2,3,4-tetrahydropyrimidine-2,4-dione (20 g, 124.56 mmol, 1 equiv), DMF (200 mL), NaSCH₃ (23.0 g, 328.57 mmol, 2.64 equiv). The resulting solution was stirred for overnight at room temperature. The resulting solution was diluted with ethyl acetate and collected by filtration. The solid was washed with H₂O and collected by filtration and dried. This resulted in 11 g (51.28%) of 6-[(methylsulfanyl)methyl]-1,2,3,4-tetrahydropyrimidine-2,4-dione as a white solid. LC-MS-BLV-CY-205-1: (ES, m/z): 173 [M+H]⁺. 1H-NMR-BLV-CY-205-1: (300 MHz, D₂O, ppm): δ 5.69 (s, 1H), 3.42 (s, 2H), 2.02 (s, 3H).

Synthesis of 2,4-dichloro-6-[(methylsulfanyl)methyl]pyrimidine: Into a 500-mL round-bottom flask, was placed 6-[(methylsulfanyl)methyl]-1,2,3,4-tetrahydropyrimidine-2,4-dione (9.5 g), phosphoroyl trichloride (60 mL). The resulting solution was stirred overnight at 90° C. The resulting mixture was concentrated. The combined organic layer was then quenched by the addition of NaHCO₃. The resulting solution was extracted with ethyl acetate (100 mL) and washed with brine (100 mL). The residue was applied onto a silica gel column with PE (100%). This resulted in 7.2 g of 2,4-dichloro-6-[(methylsulfanyl)methyl]pyrimidine as colorless oil. LC-MS-BLV-CY-205-2: (ES, m/z): 209 [M+H]⁺. 1H-NMR-BLV-CY-205-2: (300 MHz, d₆-DMSO, ppm): δ 7.80 (s, 1H), 3.78 (s, 2H), 2.07 (s, 3H).

Synthesis of 2,4-dichloro-6-(methanesulfinylmethyl)pyrimidine: Into a 50-mL round-bottom flask, was placed 2,4-dichloro-6-[(methylsulfanyl)methyl]pyrimidine (2 g, 9.57 mmol, 1 equiv), H₂O (4 mL), EA (8 mL), MeOH (4 mL) string at room temperature. To this was added sodium periodate (2.0 g, 9.57 mmol, 1.0 equiv), in portions at room temperature. The resulting solution was stirred overnight at room temperature. The reaction was then diluted by the addition of EA. The solids were filtered out and the combined organic layer was concentrated. The residue was applied onto a silica gel column with ethyl acetate/petroleum ether (3:1). This resulted in 1.5 g (69.67%) of 2,4-dichloro-6-(methanesulfinylmethyl)pyrimidine as colorless oil. LC-MS-BLV-CY-205-4: (ES, m/z): 225 [M+H]⁺. 1H-NMR-BLV-CY-205-4: (300 MHz, d₆-DMSO, ppm): δ 7.76 (s, 1H), 4.39 (d, J=12.3 Hz, 1H), 4.19 (d, J=12.3 Hz, 1H), 2.65 (s, 3H).

Synthesis of (3R)-4-[2-chloro-6-(methanesulfinylmethyl)pyrimidin-4-yl]-3-methylmorpholine: Into a 100-mL round-bottom flask, was placed 2,4-dichloro-6-(methanesulfinylmethyl)pyrimidine (1.5 g, 6.66 mmol, 1 equiv), DCM (10 mL). This was followed by the addition of (3R)-3-methylmorpholine (0.7 g, 6.66 mmol, 1.0 equiv), TEA (0.9 g, 8.66 mmol, 1.3 equiv). The resulting solution was stirred for 4 hr at room temperature. The resulting mixture was concentrated. The crude product was purified by Flash-Prep-HPLC 0.1% NH₃.H₂O:MeCN from 15% to 41% within 11 min. This resulted in 1.2 g (62.14%) of (3R)-4-[2-chloro-6-(methanesulfinylmethyl)pyrimidin-4-yl]-3-methylmorpholine as a white solid. LC-MS-BLV-CY-205-4: (ES, m/z): 290 [M+H]⁺. 1H-NMR-BLV-CY-205-4: (300 MHz, d₆-DMSO, ppm): δ 6.81 (s, 1H), 4.33 (br s, 1H), 4.10 (d, J=12.6 Hz, 1H), 4.00-3.89 (m, 3H), 3.72 (d, J=11.7 Hz, 1H), 3.59 (dd, J=11.4, 3.0 Hz, 1H), 3.44 (td, J=12.0, 3.0 Hz, 1H). 3.20 (td, J=13.2, 3.6 Hz, 1H), 2.64 (s, 3H), 1.21 (d, J=6.6 Hz, 3H).

Synthesis of N-[([2-chloro-6-[(3R)-3-methylmorpholin-4-yl]pyrimidin-4-yl]methyl)(methyl)oxo-lambda6-sulfanylidene]-2,2,2-trifluoroacetamide: Into a 100-mL round-bottom flask, was placed (3R)-4-[2-chloro-6-(methanesulfinylmethyl)pyrimidin-4-yl]-3-methylmorpholine (1.2 g, 4.14 mmol, 1 equiv), trifluoroacetamide (0.9 g, 8.28 mmol, 2.0 equiv), PhI(AcO)₂ (1.3 g, 4.14 mmol, 1.0 equiv), MgO (0.7 g, 16.56 mmol, 4.0 equiv), Ph₂(AcO)₄ (0.05 g, 0.11 mmol, 0.03 equiv), DCM (15 mL). The resulting solution was stirred for overnight at room temperature. The resulting mixture was concentrated and applied onto a silica gel column with ethyl acetate/petroleum ether (40:60). This resulted in 1.2 g (72.30%) of N-[([2-chloro-6-[(3R)-3-methylmorpholin-4-yl]pyrimidin-4-yl]methyl)(methyl)oxo-lambda6-sulfanylidene]-2,2,2-trifluoroacetamide as a white solid. LC-MS-BLV-CY-205-5: (ES, m/z): 401 [M+H]⁺. 1H-NMR-BLV-CY-205-5: (300 MHz, CDCl₃, ppm): δ 6.48 (s, 1H), 4.84 (dd, J=13.5, 5.4 Hz, 1H), 4.65 (d, J=13.8 Hz, 1H), 4.20-4.40 (br s, 1H), 4.01 (dd, J=11.7, 3.6 Hz, 2H), 3.79 (d, J=11.7 Hz, 1H), 3.71-3.62 (m, 1H), 3.57-3.47 (m, 1H), 3.42 (s, 3H), 3.37-3.25 (m, 1H), 1.33 (d, J=6.9 Hz, 3H).

Synthesis of ([2-chloro-6-[(3R)-3-methylmorpholin-4-yl]pyrimidin-4-yl]methyl)(imino)methyl-lambda6-sulfanone: Into a 50-mL round-bottom flask, was placed N-[(([2-chloro-6-[(3R)-3-methylmorpholin-4-yl]pyrimidin-4-yl]methyl)(methyl)oxo-lambda6-sulfanylidene]-2,2,2-trifluoroacetamide (300 mg, 0.75 mmol, 1 equiv), MeOH (20 mL), K₂CO₃ (258.6 mg, 1.87 mmol, 2.5 equiv). The resulting solution was stirred for 30 min at room temperature. The resulting mixture was concentrated. The resulting solution was diluted with H₂O, extracted with ethyl acetate and the organic layer was combined. The combined mixture was concentrated. This resulted in 181 mg (79.34%) of ([2-chloro-6-[(3R)-3-methylmorpholin-4-yl]pyrimidin-4-yl]methyl)(imino)methyl-lambda6-sulfanone as a light yellow solid. LC-MS-BLV-CY-205-6: (ES, m/z): 305 [M+H]⁺. 1H-NMR-BLV-CY-205-6: (300 MHz, CD₃OD, ppm): δ 6.79 (s, 1H), 4.48-4.34 (m, 2H), 4.12-4.08 (m, 1H), 4.00 (dd, J=11.4, 3.6 Hz, 1H), 3.81 (d, J=11.7 Hz, 1H), 3.70 (dd, J=11.7, 3.0 Hz, 1H), 3.56 (td, J=12.0, 3.0 Hz, 1H), 3.37-3.27 (m, 2H), 3.09 (s, 3H), 1.33 (d, J=6 Hz, 3H).

Synthesis of ([2-chloro-6-[(3R)-3-methylmorpholin-4-yl]pyrimidin-4-yl]methyl) (methyl) (methylimino)-lambda6-sulfanone: Into a 50-mL round-bottom flask, was placed ([2-chloro-6-[(3R)-3-methylmorpholin-4-yl]pyrimidin-4-yl]methyl)(imino)methyl-lambda6-sulfanone (260 mg, 0.85 mmol, 1 equiv), Me₃OBF₄ (138.9 mg, 0.94 mmol, 1.1 equiv), DCM (10 mL). The resulting solution was stirred for 20 min at room temperature. The reaction was then quenched by the addition of MeOH. The resulting mixture was concentrated. The crude product was purified by Flash-Prep-HPLC 0.1% NH₄HCO₃:MeCN=22% increasing to 0.1% NH₄HCO₃:MeCN=40% within 9 min. This resulted in 100 mg (36.77%) of ([2-chloro-6-[(3R)-3-methylmorpholin-4-yl]pyrimidin-4-yl]methyl)(methyl)(methylimino)-lambda6-sulfanone as a white solid. LC-MS-BLV-CY-205-7: (ES, m/z): 319 [M+H]⁺.

Synthesis of [(1-[2-chloro-6-[(3R)-3-methylmorpholin-4-yl]pyrimidin-4-yl]cyclobutyl)(methyl)oxo-lambda6-sulfanylidene](methyl)amine: Into a 50-mL round-bottom flask, was placed ([2-chloro-6-[(3R)-3-methylmorpholin-4-yl]pyrimidin-4-yl]methyl)(methyl)(methylimino)-lambda6-sulfanone (100 mg, 0.31 mmol, 1 equiv), 1,3-dibromopropane (253.3 mg, 1.25 mmol, 4.0 equiv), (C₈H₁₇)₄NBr (17.2 mg, 0.03 mmol, 0.1 equiv), 2-MeTHF (8 mL), NaOH (50%) (752.7 mg, 18.82 mmol, 60 equiv). The resulting solution was stirred overnight at 60° C. Then water (20 mL) was added and extracted with EtOAc (2×20 mL). The combined organic layer was washed with brine (150 mL), dried (Na₂SO₄), filtered and concentrated. The residue was applied onto a silica gel column with ethyl acetate. This resulted in 38 mg (33.75%) of [(1-[2-chloro-6-[(3R)-3-methylmorpholin-4-yl]pyrimidin-4-yl]cyclobutyl)(methyl)

oxo-lambda6-sulfanylidene](methyl)amine as a light yellow solid. LC-MS-BLV-CY-205-8: (ES, m/z): 359 [M+H]+. 1H-NMR-BLV-CY-205-8: (300 MHz, d$_6$-DMSO, ppm): δ 6.95 (s, 1H), 5.68-5.59 (m, 1H), 5.10-4.98 (m, 2H), 4.48 (d, J=11.7 Hz, 1H), 4.34-4.23 (m, 1H), 4.03-3.92 (m, 2H), 3.73 (d, J=11.4 Hz, 1H), 3.61 (d, J=11.4 Hz, 1H), 3.46 (t, J=11.1 Hz, 1H), 3.20 (t, J=9.3 Hz, 1H), 2.98-2.82 (m, 4H), 2.76-2.74 (m, 1H), 2.64 (d, J=5.7 Hz, 3H), 1.21 (d, J=6.9 Hz, 3H).

Synthesis of methyl[methyl(1-[6-[(3R)-3-methylmorpholin-4-yl]-2-[1H-pyrrolo[2,3-b]pyridin-4-yl]pyrimidin-4-yl]cyclobutyl)oxo-lambda6-sulfanylidene]amine: Into a 8-mL microwave and maintained with an inert atmosphere of nitrogen, was placed 4-(4,4,5,5-tetramethyl-1,3,2-dioxaborolan-2-yl)-1H-pyrrolo[2,3-b]pyridine (32.6 mg, 0.13 mmol, 1.2 equiv), [(1-[2-chloro-6-[(3R)-3-methylmorpholin-4-yl]pyrimidin-4-yl]cyclobutyl)(methyl)oxo-lambda6-sulfanylidene](methyl)amine (40 mg, 0.11 mmol, 1 equiv), PdCl$_2$(PPh$_3$)$_2$ (15.6 mg, 0.02 mmol, 0.2 equiv), Na$_2$CO$_3$ (23.5 mg, 0.22 mmol, 1.99 equiv), DME (2.5 mL), H$_2$O (0.8 mL). The resulting solution was stirred for 40 min at 90° C. The crude product was purified by Prep-HPLC. This resulted in 23.8 mg (48.47%) of methyl[methyl(1-[6-[(3R)-3-methylmorpholin-4-yl]-2-[1H-pyrrolo[2,3-b]pyridin-4-yl]pyrimidin-4-yl]cyclobutyl)oxo-lambda6-sulfanylidene]amine as a white solid. LC-MS-BLV-CY-205-0: (ES, m/z): 441 [M+H]+. 1H-NMR-BLV-CY-205-0: (300 MHz, d$_6$-DMSO, ppm): δ 11.81 (s, 1H), 8.34 (dd, J=5.1, 1.5 Hz, 1H), 8.00 (d, J=5.1 Hz, 1H), 7.60 (d, J=5.7 Hz, 1H), 7.26-7.25 (m, 1H), 6.97-6.95 (m, 1H), 5.72-5.68 (m, 1H), 5.11 (d, J=16.2 Hz, 1H), 4.97 (d, J=10.2 Hz, 1H), 4.62-4.56 (m, 2H), 4.26-4.18 (m, 1H), 4.03 (d, J=8.7 Hz, 1H), 3.82 (d, J=11.4 Hz, 1H), 3.69 (d, J=11.4 Hz, 1H), 3.55 (t, J=11.7 Hz, 1H), 3.33-3.24 (m, 2H), 3.02-2.99 (t, J=5.4 Hz, 3H), 2.80-2.73 (m, 1H), 2.69 (s, 2H), 2.65 (d, J=3.0 Hz, 1H), 1.30-1.26 (m, 3H).

Example CY-206: Preparation of Imino(methyl)[1-[6-(1,4-oxazepan-4-yl)-2-[1H-pyrrolo[2,3-b]pyridin-4-yl]pyrimidin-4-yl]cyclopropyl]-lambda6-sulfanone Synthesis of 4-[2-chloro-6-(methanesulfinylmethyl)pyrimidin-4-yl]-1,4-oxazepane: Into a 100-mL round-bottom flask, was placed 2,4-dichloro-6-(methanesulfinylmethyl)pyrimidine (2.0 g, 8.89 mmol, 1 equiv), 1,4-oxazepane hydrochloride (1.2 g, 8.89 mmol, 1.0 equiv), TEA (2.2 g, 22.21 mmol, 2.5 equiv), DCM (20 mL). The resulting solution was stirred for 4 hr at room temperature. The resulting mixture was concentrated. The crude product was purified with 0.1% NH$_3$.H$_2$O:MeCN=12% increasing to 0.1% NH$_3$.H$_2$O:MeCN=28% within 9 min. This resulted in 1.6 g (62.14%) of 4-[2-chloro-6-(methanesulfinyl methyl)pyrimidin-4-yl]-1,4-oxazepane as a white solid. LC-MS-BLV-CY-206-1: (ES, m/z): 290 [M+H]+.

Synthesis of tert-butyl N-([[2-chloro-6-(1,4-oxazepan-4-yl)pyrimidin-4-yl]methyl](methyl)oxo-lambda6-sulfanylidene)carbamate: Into a 250-mL round-bottom flask, was placed 4-[2-chloro-6-(methanesulfinylmethyl)pyrimidin-4-yl]-1,4-oxazepane (1.6 g, 5.52 mmol, 1 equiv), tert-butyl carbamate (1.3 g, 11.10 mmol, 2.01 equiv), MgO (0.89 g, 22.08 mmol, 4.00 equiv), PhI(AcO)$_2$ (1.77 g, 5.52 mmol, 1.00 equiv), Rh$_2$(AcO)$_4$ (61.0 mg, 0.14 mmol, 0.02 equiv), DCM (50 mL). The resulting solution was stirred overnight at 60° C. The resulting solution was extracted with dichloromethane. The solids were filtered out. The combined organic layer was concentrated. The residue was applied onto a silica gel column with ethyl acetate/petroleum ether (60:40). This resulted in 2.1 g (93.93%) of tert-butyl N-([[2-chloro-6-(1,4-oxazepan-4-yl)pyrimidin-4-yl]methyl](methyl)oxo-lambda6-sulfanylidene)carbamate as a white solid. LC-MS-BLV-CY-206-2: (ES, m/z): 405 [M+H]+.

Synthesis of tert-butyl N-([1-[2-chloro-6-(1,4-oxazepan-4-yl)pyrimidin-4-yl]cyclopropyl] (methyl) oxo-lambda6-sulfanylidene)carbamate: Into a 50-mL round-bottom flask, was placed 1,2-dibromoethane (980.81g, 5.221 mmol, 5.01 equiv), tert-butyl N-([[2-chloro-6-(1,4-oxazepan-4-yl)pyrimidin-4-yl]methyl] (methyl)oxo-lambda6-sulfanylidene) carbamate (700 mg, 1.23 mmol, 1 equiv), (C$_8$H$_{17}$)$_4$NBr (94.53 mg, 0.173 mmol, 0.10 equiv), K$_2$CO$_3$ (2867.12 mg, 20.745 mmol, 12.00 equiv), DMSO (25 mL). The resulting solution was stirred for 3 hr at 60° C. Then water (50 mL) was added and extracted with EtOAc (2×50 mL). The combined organic layer was washed with brine (50 mL), dried (Na$_2$SO$_4$), filtered and concentrated. The residue was applied onto a silica gel column with ethyl acetate/petroleum ether (1:1). This resulted in 130 mg (17.45%) of tert-butyl N-([1-[2-chloro-6-(1,4-oxazepan-4-yl)pyrimidin-4-yl]cyclopropyl](methyl)oxo-lambda6-sulfanylidene)carbamate as a light yellow solid. LC-MS-BLV-CY-206-3: (ES, m/z): 431 [M+H]+. $^1$H-NMR-BLV-CY-206-3: (300 MHz, d$_6$-DMSO, ppm): δ 6.83 (s, 1H), 3.86-3.62 (m, 8H), 3.40 (s, 3H), 1.88-1.83 (m, 4H), 1.68-1.64 (m, 1H), 1.45-1.40 (m, 1H), 1.33 (s, 9H).

Synthesis of tert-butyl N-[methyl([1-[6-(1,4-oxazepan-4-yl)-2-[1H-pyrrolo[2,3-b]pyridin-4-yl]pyrimidin-4-yl]cyclopropyl])oxo-lambda6-sulfanylidene]carbamate: Into a 8-mL microwave and maintained with an inert atmosphere of nitrogen, was placed tert-butyl N-([1-[2-chloro-6-(1,4-oxazepan-4-yl)pyrimidin-4-yl]cyclopropyl](methyl)oxo-lambda6-sulfanylidene) carbamate (130 mg, 0.302 mmol, 1 equiv), 4-(4,4,5,5-tetramethyl-1,3,2-dioxaborolan-2-yl)-1H-pyrrolo[2,3-b]pyridine (110.45 mg, 0.452 mmol, 1.50 equiv), PdCl$_2$(PPh$_3$)$_2$ (42.35 mg, 0.06 mmol, 0.2 equiv), Na$_2$CO$_3$ (63.94 mg, 0.603 mmol, 2.0 equiv), DME (3 mL), H$_2$O (0.5 mL). The resulting solution was stirred for 40 min at 90° C. The solids were filtered out and the combined organic layer was purified by Prep-HPLC. This resulted in 58 mg (37.51%) of tert-butyl N-[methyl([1-[6-(1,4-oxazepan-4-yl)-2-[1H-pyrrolo[2,3-b]pyridin-4-yl]pyrimidin-4-yl]cyclopropyl])oxo-lambda6-sulfanylidene]carbamate as a yellow solid. LC-MS-LC-MS-BLV-CY-206-4: (ES, m/z): 513 [M+H]+. 1H-NMR-BLV-CY-206-4: (300 MHz, d$_6$-DMSO, ppm): δ 11.82 (s, 1H), 8.34 (d, J=5.1 Hz, 1H), 7.94 (d, J=5.1 Hz, 1H), 7.60 (t, J=3.0 Hz, 1H), 7.21 (s, 1H), 6.85 (s, 1H), 3.98-3.71 (m, 6H), 3.67 (t, J=5.4 Hz, 2H), 3.52 (s, 3H), 1.99-1.92 (m, 4H), 1.80-1.75 (m, 1H), 1.55-1.50 (m, 1H), 1.33 (s, 9H).

Synthesis of imino(methyl)[1-[6-(1,4-oxazepan-4-yl)-2-[1H-pyrrolo[2,3-b]pyridin-4-yl]pyrimidin-4-yl]cyclopropyl]-lambda6-sulfanone: Into a 25-mL round-bottom flask, was placed tert-butyl N-[methyl([1-[6-(1,4-oxazepan-4-yl)-2-[1H-pyrrolo[2,3-b]pyridin-4-yl]pyrimidin-4-yl]cyclopropyl])oxo-lambda6-sulfanylidene]carbamate (50 mg), HCl (Et$_2$O) (2 mL). The resulting solution was stirred for 1 hr at room temperature. The resulting mixture was concentrated and purified by Prep-HPLC. This resulted in 29.7 mg of imino(methyl)[1-[6-(1,4-oxazepan-4-yl)-2-[1H-pyrrolo[2,3-b]pyridin-4-yl]pyrimidin-4-yl]cyclopropyl]-lambda6-sulfanone as a white solid. LC-MS-BLV-CY-206-0: (ES, m/z): 413 [M+H]+. $^1$H-NMR-BLV-CY-206-0: (300 MHz, CD$_3$OD, ppm): δ 8.31 (d, J=5.1 Hz, 1H), 8.07 (d, J=5.4 Hz, 1H), 7.51 (d, J=3.3 Hz, 1H), 7.37 (d, J=3.3 Hz, 1H), 7.00 (s, 1H), 4.22-3.87 (m, 6H), 3.79 (t, J=5.4 Hz, 2H), 3.22 (s, 3H), 2.12-2.05 (m, 2H), 1.88-1.77 (m, 2H), 1.62 (s, 2H).

Example CY-207: Preparation of [methyl(1-[6-[(3R)-3-methylmorpholin-4-yl]-2-[1H-pyrrolo[2,3-b]pyridin-4-yl]pyrimidin-4-yl]cyclopropyl)oxo-lambda6-sulfanylidene](propan-2-yl)amine Synthesis of methyl 2-chloro-6-[(3R)-3-methylmorpholin-4-yl]pyrimidine-4-carboxylate: Into a 500-mL round-bottom flask, was placed methyl 2,6-dichloropyrimidine-4-carboxylate (10 g, 0.05 mmol, 1 equiv), DCM (200 mL, 2.35 mmol, 48.75 equiv), (3R)-3-methylmorpholine (4.9 g, 0.05 mmol, 1.00 equiv), TEA (6.37 g, 0.06 mmol, 1.30 equiv). The resulting solution was stirred for 18 hr at room temperature. The resulting solution was diluted with 800 mL of $H_2O$ and extracted with 4×400 ml of dichloromethane and the resulting mixture was washed with 2×300 mL of brine. The organic layer was concentrated and applied onto a silica gel column with ethyl acetate/petroleum ether (10%). This resulted in 10 g (76.19%) of methyl 2-chloro-6-[(3R)-3-methylmorpholin-4-yl]pyrimidine-4-carboxylate as a yellow solid. LC-MS-BLV-CY-200-1: (ES, m/z): 272 $[M+H]^+$. H-NMR-BLV-CY-200-1: (300 MHz, $d_6$-DMSO, ppm): δ 7.15 (s, 1H), 4.38 (br s, 1H), 4.11-4.13 (m, 1H), 4.01-4.09 (m, 1H), 3.98 (s, 3H), 3.81 (d, J=11.7 Hz, 1H), 3.70 (d, J=11.7 Hz, 1H), 3.55 (t, J=12.3 Hz, 1H), 3.34 (t, J=12.9 Hz, 1H), 1.35 (d, J=6.9 Hz, 3H).

Synthesis of [2-chloro-6-[(3R)-3-methylmorpholin-4-yl]pyrimidin-4-yl]methanol: Into a 500-mL 3-necked round-bottom flask purged and maintained with an inert atmosphere of nitrogen, was placed methyl 2-chloro-6-[(3R)-3-methylmorpholin-4-yl]pyrimidine-4-carboxylate (10 g, 0.04 mmol, 1 equiv), THF (200 mL). This was followed by the addition of $LiBH_4$ in THF (11 mL, 0.6 equiv) dropwise with stirring. The resulting solution was stirred for 18 hr at room temperature. The reaction was then quenched by the addition of 150 mL of water. The resulting solution was extracted with 2×100 ml of ethyl acetate and the EA layer dried over anhydrous sodium sulfate and concentrated. This resulted in 8.97 g (crude) of [2-chloro-6-[(3R)-3-methylmorpholin-4-yl]pyrimidin-4-yl]methanol as a yellow solid. LC-MS-BLV-CY-200-2: (ES, m/z): 244 $[M+H]^+$. H-NMR-BLV-CY-200-2: (300 MHz, $d_6$-DMSO, ppm): δ 6.44 (s, 1H), 4.60 (s, 2H), 4.32 (br s, 1H), 4.03 (d, J=11.4 Hz, 1H), 3.79 (d, J=11.4 Hz, 1H), 3.69 (d, J=11.7 Hz, 1H), 3.54 (t, J=12.3 Hz, 1H), 3.30 (t, J=13.2 Hz, 1H), 2.38 (br s, 2H), 1.33 (d, J=6.9 Hz, 3H).

Synthesis of [2-chloro-6-[(3R)-3-methylmorpholin-4-yl]pyrimidin-4-yl]methyl methanesulfonate: Into a 500-mL 3-necked round-bottom flask purged and maintained with an inert atmosphere of nitrogen, was placed [2-chloro-6-[(3R)-3-methylmorpholin-4-yl]pyrimidin-4-yl]methanol (8.97 g, 0.04 mmol, 1 equiv), DCM (200 mL), TEA (4.85 g, 0.05 mmol, 1.30 equiv). This was followed by the addition of methanesulfonyl chloride (9.13 g, 0.08 mmol, 2.17 equiv) dropwise with stirring. The resulting solution was stirred for 1 hr at 0° C. in an ice/salt bath. The reaction was then quenched by the addition of 300 mL of water. The resulting solution was extracted with 3×300 ml of dichloromethane. The DCM layer was washed with 2×400 mL of brine, dried by $Na_2SO_4$ and concentrated. This resulted in 11 g (92.87%) of [2-chloro-6-[(3R)-3-methylmorpholin-4-yl]pyrimidin-4-yl]methyl methanesulfonate as a yellow solid. LC-MS-BLV-CY-200-3: (ES, m/z): 322 $[M+H]^+$. H-NMR-BLV-CY-200-4: (300 MHz, $d_6$-DMSO, ppm): δ 6.85 (s, 1H), 5.10 (s, 2H), 4.38 (br, 1H), 3.94 (d, J=11.4 Hz, 1H), 3.72 (d, J=11.7 Hz, 1H), 3.58 (d, J=11.7 Hz, 1H), 3.45 (t, J=12.0 Hz, 1H), 3.18-3.26 (m, 1H), 2.78-2.86 (m, 1H), 2.43 (s, 3H), 1.21 (d, J=6.9 Hz, 3H).

Synthesis of (3R)-4-[2-chloro-6-(iodomethyl)pyrimidin-4-yl]-3-methylmorpholine: Into a 500-mL round-bottom flask, was placed [2-chloro-6-[(3R)-3-methylmorpholin-4-yl]pyrimidin-4-yl]methyl methanesulfonate (14.8 g, 0.05 mmol, 1 equiv), 1,4-dioxane (300 mL), LiI (11.97 g, 0.09 mmol, 1.94 equiv). The resulting solution was stirred for 1 hr at 100° C. in an oil bath. The resulting mixture was cooled and added 400 ml of 20% $Na_2S_2O_3$ solution. The resulting mixture was extracted with 3×400 mL of ethyl acetate. The organic mixture was dried over anhydrous sodium sulfate. The filtrate was concentrated. The residue was applied onto a silica gel column with ethyl acetate/petroleum ether (9%). This resulted in 7.45 g (45.81%) of (3R)-4-[2-chloro-6-(iodomethyl)pyrimidin-4-yl]-3-methylmorpholine as a yellow solid. H-NMR-BLV-CY-200-4: (300 MHz, $d_6$-DMSO, ppm): δ 6.95 (s, 1H), 4.58 (s, 2H), 4.35 (br, 1H), 4.10-3.91 (m, 2H), 3.72 (d, J=11.4 Hz, 1H), 3.59 (d, J=11.4 Hz, 1H), 3.44 (t, J=12.0 Hz, 1H), 3.22 (t, J=13.2 Hz, 1H), 1.21 (d, J=6.9 Hz, 3H).

Synthesis of (3R)-4-[2-chloro-6-[(methylsulfanyl)methyl]pyrimidin-4-yl]-3-methylmorpholine: Into a 250-mL round-bottom flask, was placed (3R)-4-[2-chloro-6-(iodomethyl)pyrimidin-4-yl]-3-methylmorpholine (7.45 g, 21.07 mmol, 1 equiv), N,N-dimethylformamide (50 mL), (methylsulfanyl)sodium (2.83 g, 20.2 mmol, 1 equiv). The resulting solution was stirred for 1 hr at 25° C. The reaction was then quenched by the addition of 150 mL of water/ice. The resulting solution was extracted with 3×50 ml of ethyl acetate. The organic mixture was dried over anhydrous sodium sulfate. The filtrate was concentrated. The residue was applied onto a silica gel column with ethyl acetate/petroleum ether (10%). This resulted in 4.48 g (77.66%) of (3R)-4-[2-chloro-6-[(methylsulfanyl)methyl]pyrimidin-4-yl]-3-methylmorpholine as yellow oil. LC-MS-BLV-CY-200-5: (ES, m/z): 274 $[M+H]^+$. H-NMR-BLV-CY-200-5: (300 MHz, $d_6$-DMSO, ppm): δ 6.77 (s, 1H), 4.32 (br, 1H), 3.95-4.01 (m, 2H), 3.72 (d, J=11.7 Hz, 1H), 3.61 (s, 1H), 3.54 (s, 2H), 3.39-3.49 (m, 1H), 3.13-3.22 (m, 1H), 2.07 (s, 3H), 1.20 (d, J=6.6 Hz, 3H).

Synthesis of (3R)-4-[2-chloro-6-(methanesulfinylmethyl)pyrimidin-4-yl]-3-methylmorpholine: Into a 250-mL round-bottom flask, was placed (3R)-4-[2-chloro-6-[(methylsulfanyl)methyl]pyrimidin-4-yl]-3-methylmorpholine (4.4 g, 16.07 mmol, 1 equiv), water (15 mL), EA (30 mL), methanol (15 mL), sodium periodate (3.45 g, 16.13 mmol, 1.00 equiv). The resulting solution was stirred for 18 hr at 25° C. The resulting solution was diluted with 80 mL of DCM. The solids were filtered out. The resulting solution was extracted with 3×50 mL of dichloromethane. The organic mixture was dried over anhydrous sodium sulfate. The solids were filtered out. The filtrate was concentrated. The residue was applied onto a silica gel column with methanol/dichloromethane (0-7%). This resulted in 3.0 g (64.42%) of (3R)-4-[2-chloro-6-(methanesulfinylmethyl)pyrimidin-4-yl]-3-methylmorpholine as a off-white solid. LC-MS-BLV-CY-200-6: (ES, m/z): 290 $[M+H]^+$. H-NMR-BLV-CY-200-6: (300 MHz, $d_6$-DMSO, ppm): δ 6.81 (s, 1H), 4.32 (br, 1H), 4.08 (d, J=12.3 Hz, 1H), 3.89-4.00 (m, 3H), 3.72 (d, J=14.4 Hz, 1H), 3.59 (d, J=11.7 Hz, 1H), 3.44 (t, J=12.0 Hz, 1H), 3.20 (t, J=11.1 Hz, 1H), 2.64 (s, 3H), 1.21 (d, J=6.6 Hz, 3H).

Synthesis of N-[([2-chloro-6-[(3R)-3-methylmorpholin-4-yl]pyrimidin-4-yl]methyl)(methyl)oxo-lambda6-sulfanylidene]-2,2,2-trifluoroacetamide: Into a 250-mL round-bottom flask, was placed (3R)-4-[2-chloro-6-(methanesulfinylmethyl)pyrimidin-4-yl]-3-methylmorpholine (2.9 g, 10.01 mmol, 1 equiv), DCM (95 mL), trifluoroacetamide (2.27 g, 20.08 mmol, 2.01 equiv), PhI(AcO)₂ (3.23 g, 10.03 mmol, 1.00 equiv), oxomagnesium (1.6 g, 39.70 mmol, 3.97 equiv), 1,1,1-tris(acetyloxy)dirhodium-1-yl acetate (0.11 g, 0.25 mmol, 0.02 equiv). The resulting solution was stirred for 18 hr at room temperature. Then more trifluoroacetamide (0.57 g), PhI(AcO)₂ (0.81g), oxomagnesium (0.4 g), 1,1,1-tris(acetyloxy)dirhodium-1-yl acetate (27 mg) was added. The resulting solution was stirred for another 18 hr at room temperature. The solids were filtered out. The filtrate was concentrated. The residue was applied onto a silica gel column with ethyl acetate/petroleum ether (20%). This resulted in 2.6 g (64.82%) of N-[([2-chloro-6-[(3R)-3-methylmorpholin-4-yl]pyrimidin-4-yl]methyl)(methyl)oxo-lambda6-sulfanylidene]-2,2,2-trifluoroacetamide as a light yellow solid. LC-MS-BLV-CY-200-7: (ES, m/z): 401 [M+H]⁺. H-NMR-BLV-CY-200-7: (300 MHz, CDCl₃, ppm): δ 6.48 (s, 1H), 4.84 (dd, J=5.4 Hz, 13.5 Hz, 1H), 4.65 (d, J=13.8 Hz, 1H), 3.84-4.40 (m, 3H), 3.75 (d, J=11.4 Hz, 1H), 3.62-3.70 (m, 1H), 3.47-3.57 (m, 1H), 3.42 (s, 3H), 3.25-3.37 (m, 1H), 1.34 (d, J=6.9 Hz, 3H).

Synthesis of (1-[2-chloro-6-[(3R)-3-methylmorpholin-4-yl]pyrimidin-4-yl]cyclopropyl)(imino)methyl-lambda6-sulfanone: Into a 50-mL round-bottom flask purged and maintained with an inert atmosphere of nitrogen, was placed N-[([2-chloro-6-[(3R)-3-methylmorpholin-4-yl]pyrimidin-4-yl]methyl)(methyl)oxo-lambda6-sulfanylidene]-2,2,2-trifluoroacetamide (400 mg, 1.00 mmol, 1 equiv), 2-MeTHF (15 mL), 1,2-dibromoethane (939 mg, 5.00 mmol, 5.01 equiv), (C₈H₁₇)₄NBr (54.7 mg, 0.1 equiv), 10% NaOH (10.0 mmol, 10.0 equiv). The resulting solution was stirred for 2 hr at 60° C. in an oil bath. The crude product was purified by Flash-Prep-HPLC with the following conditions (IntelFlash-1): Column, C18 silica gel; mobile phase, 0.5% NH₃.H₂O=52% increasing to 0.5% NH₃.H₂O=56%; Detector, 254 nm & 220 nm. This resulted in 130 mg (39.37%) of (1-[2-chloro-6-[(3R)-3-methylmorpholin-4-yl]pyrimidin-4-yl]cyclopropyl) (imino) methyl-lambda6-sulfanone as a yellow solid. LC-MS-BLV-CY-200-8: (ES, m/z): 331 [M+H]⁺.

Synthesis of [(1-[2-chloro-6-[(3R)-3-methylmorpholin-4-yl]pyrimidin-4-yl]cyclopropyl)(methyl)oxo-lambda6-sulfanylidene](propan-2-yl)amine: Into a 50-mL 3-necked round-bottom flask, was placed (1-[2-chloro-6-[(3R)-3-methylmorpholin-4-yl]pyrimidin-4-yl]cyclopropyl)(imino)methyl-lambda-sulfanone (180 mg, 0.54 mmol, 1 equiv), N,N-dimethylformamide (3 mL). This was followed by the addition of NaH (55 mg, 1.38 mmol, 2.50 equiv) at 0° C. The resulting solution was stirred for 0.5 hr at 0° C. To this was added 2-iodopropane (464 mg, 2.73 mmol, 5.02 equiv) dropwise with stirring at 0° C. The resulting solution was stirred for 16 hr at room temperature. The reaction was then quenched by the addition of 1 mL of water. The crude product was purified by Flash-Prep-HPLC with the following conditions (IntelFlash-1): Column, C18 silica gel; mobile phase, 0.05% NH₃.H₂O/CH₃CN=30% increasing to 0.05% NH₃.H₂O/CH₃CN=40% within 6 min; Detector, 254 nm & 220 nm. This resulted in 22 mg (10.84%) of [(1-[2-chloro-6-[(3R)-3-methylmorpholin-4-yl]pyrimidin-4-yl]cyclopropyl)(methyl)oxo-lambda6-sulfanylidene](propan-2-yl)amine as a yellow solid. LC-MS-BLV-CY-207-1: (ES, m/z): 373 [M+H]⁺. H-NMR-BLV-CY-207-1: (300 MHz, CDCl₃, ppm): δ 7.11 (br s, 1H), 4.37 (br s, 1H), 4.00 (dd, J=11.4, 3.6 Hz, 2H), 3.81 (d, J=11.7 Hz, 1H), 3.65 (dd, J=11.7, 3.6 Hz, 2H), 3.55 (td, J=12.3, 3.0 Hz, 1H), 3.31 (td, J=13.5, 4.8 Hz, 1H), 3.14-3.05 (m, 2H), 2.07-1.92 (m, 1H), 1.71-1.55 (m, 4H), 1.35 (d, J=6.9 Hz, 3H), 1.21-1.18 (m, 6H).

Synthesis of Into a 20-mL microwave tube purged and maintained with an inert atmosphere of nitrogen, was placed [(1-[2-chloro-6-[(3R)-3-methylmorpholin-4-yl]pyrimidin-4-yl]cyclopropyl)(methyl)oxo-lambda6-sulfanylidene](propan-2-yl)amine (20 mg, 0.05 mmol, 1 equiv), DME (2 mL), 4-(4,4,5,5-tetramethyl-1,3,2-dioxaborolan-2-yl)-1H-pyrrolo[2,3-b]pyridine (20 mg, 0.08 mmol, 1.53 equiv), dichloropalladium; bis(triphenylphosphane) (8 mg, 0.01 mmol, 0.21 equiv), sodium methaneperoxoate sodium (11 mg, 0.10 mmol, 1.92 equiv), water (0.5 mL). The final reaction mixture was irradiated with microwave radiation for 30 min at 90° C. The mixture was cooled to room temperature. The crude product was purified by Flash-Prep-HPLC with the following conditions (IntelFlash-1): Column, C18 silica gel; mobile phase, 0.05% HCOOH/CH₃CN=35% increasing to 0.05% HCOOH/CH₃CN=40% within 5 min; Detector, 254 nm & 220 nm. This resulted in 15.2 mg (62.34%) of [methyl(1-[6-[(3R)-3-methylmorpholin-4-yl]-2-[1H-pyrrolo[2,3-b]pyridin-4-yl]pyrimidin-4-yl]cyclopropyl)oxo-lambda6-sulfanylidene](propan-2-yl)amine as a light yellow solid. LC-MS-BLV-CY-207-0: (ES, m/z): 455 [M+H]⁺. H-NMR-BLV-CY-207-0: (300 MHz, CDCl₃, ppm): δ 9.38 (s, 1H), 8.43 (d, J=4.8 Hz, 1H), 8.10 (d, J=5.1 Hz, 1H), 7.47 (d, J=3.0 Hz, 1H), 7.37 (s, 1H), 7.25 (d, J=2.7 Hz, 1H), 4.56 (br s, 1H), 4.21 (d, J=12.0 Hz, 1H), 4.11 (dd, J=11.4 Hz, 3.0 Hz, 1H), 3.89 (d, J=11.7 Hz, 1H), 3.81-3.72 (m, 2H), 3.65 (t, J=12.6 Hz, 1H), 3.43 (td, J=12.4 Hz, 3.0 Hz, 1H), 3.16 (d, J=3.0 Hz, 3H), 2.13-2.10 (m, 1H), 1.81-1.65 (m, 3H), 1.42 (d, J=6.6 Hz, 3H), 1.24 (dd, J=6.3, 1.5 Hz, 3H), 1.17 (d, J=6.3 Hz, 3H).

Example CY-209: Preparation of (2H3)methyl [methyl(1-[6-[(3R)-3-methylmorpholin-4-yl]-2-[1H-pyrrolo[2,3-b]pyridin-4-yl]pyrimidin-4-yl]cyclopropyl)oxo-lambda6-sulfanylidene]amine Synthesis of [(1-[2-chloro-6-[(3R)-3-methylmorpholin-4-yl]pyrimidin-4-yl]cyclopropyl)(methyl)oxo-lambda6-sulfanylidene]((2H3)methyl)amine: Into a 8-mL vial, was placed (1-[2-chloro-6-[(3R)-3-methylmorpholin-4-yl]pyrimidin-4-yl]cyclopropyl)(imino)methyl-lambda6-sulfanone (100 mg, 0.302 mmol, 1 equiv). This was followed by the addition of DMF (2 mL) stirred for 5 min at 0° C. To this was added NaH (14.51 mg, 0.605 mmol, 2.0 equiv) stirred for 5 min at 0° C. To the mixture was added iodomethane-d₃ (87.63 mg, 0.605 mmol, 2.0 equiv) at 0° C. The resulting solution was stirred for 30 min at room temperature. The reaction was then quenched by the addition of water. The crude product was purified by Prep-HPLC. This resulted in 43 mg (40.89%) of [(1-[2-chloro-6-[(3R)-3-methylmorpholin-4-yl]pyrimidin-4-yl]cyclopropyl) (methyl)oxo-lambda6-sulfanylidene]((2H3)methyl)amine as light yellow oil. LC-MS-BLV-CY-209-1: (ES, m/z): 348 [M+H]⁺. H-NMR-BLV-CY-209-1: (300 MHz, d₆-DMSO, ppm): δ 7.04 (d, J=9.9 Hz, 1H), 4.38 (brs, 1H), 4.04 (d, J=12.0 Hz, 1H), 3.93 (d, J=9.0 Hz, 1H), 3.72 (d, J=12.0 Hz, 1H), 3.58 (d, J=9.6 Hz, 1H), 3.44 (t, J=9.9 Hz, 1H), 3.19 (t, J=11.7 Hz, 1H), 3.08 (s, 3H), 1.75-1.67 (m, 1H), 1.59-1.52 (m, 1H), 1.44-1.28 (m, 1H), 1.33-1.28 (m, 1H), 1.21 (d, J=6.0 Hz, 3H).

Synthesis of (2H3)methyl[methyl(1-[6-[(3R)-3-methylmorpholin-4-yl]-2-[1H-pyrrolo[2,3-b]pyridin-4-yl]pyrimidin-4-yl]cyclopropyl)oxo-lambda6-sulfanylidene]amine:
Into a 8-mL microwave and maintained with an inert atmosphere of nitrogen was placed [(1-[2-chloro-6-[(3R)-3-methylmorpholin-4-yl]pyrimidin-4-yl]cyclopropyl)(methyl)oxo-lambda6-sulfanylidene]((2H3)methyl)amine (40 mg, 0.115 mmol, 1 equiv), 4-(4,4,5,5-tetramethyl-1,3,2-dioxaborolan-2-yl)-1H-pyrrolo[2,3-b]pyridine (40.21 mg, 0.172 mmol, 1.5 equiv), Na₂CO₃ (24.37 mg, 0.23 mmol, 2.0 equiv), PdCl$_2$(PPh$_3$)$_2$ (16.14 mg, 0.023 equiv), DME (3 mL), H$_2$O (0.5 mL). The resulting solution was stirred for 30 min at 90° C. The crude product was purified by Prep-HPLC. This resulted in 13 mg (24.31%) of (2H3)methyl[methyl(1-[6-[(3R)-3-methylmorpholin-4-yl]-2-[1H-pyrrolo[2,3-b]pyridin-4-yl]pyrimidin-4-yl]cyclopropyl)oxo-lambda6-sulfanylidene]amine as a white solid.

LC-MS-BLV-CY-209-0: (ES, m/z): 430 [M+H]$^+$. H-NMR-BLV-CY-209-0: (300 MHz, CD$_3$OD, ppm): δ 8.31 (d, J=5.4 Hz, 1H), 8.07 (d, J=5.1 Hz, 1H), 7.52 (d, J=3.6 Hz, 1H), 7.36 (d, J=3.3 Hz, 1H), 7.05 (d, J=5.4 Hz, 1H), 4.66 (brs, 1H), 4.28 (dd, J=12.3 Hz, 2.4 Hz, 1H), 4.08 (dd, J=12.0 Hz, 3.6 Hz, 1H), 3.89 (d, J=11.4 Hz, 1H), 3.79 (dd, J=11.7 Hz, 3.0 Hz, 1H), 3.65 (td, J=11.4 Hz, 2.7 Hz, 1H), 3.42 (dd, J=13.8 Hz, 4.2 Hz, 1H), 3.28 (s, 3H), 2.07-2.00 (m, 1H), 1.81-1.74 (m, 1H), 1.70-1.63 (m, 1H), 1.59-1.49 (m, 1H), 1.40 (d, J=6.9 Hz, 3H).

Example CY-212: Preparation of 2-[6-[(3R)-3-methylmorpholin-4-yl]-2-[1H-pyrrolo[2,3-b]pyridin-4-yl]pyrimidin-4-yl]propan-2-ol Synthesis of methyl 2-chloro-6-[(3R)-3-methylmorpholin-4-yl]pyrimidine-4-carboxylate: Into a 25-mL round-bottom flask, was placed methyl 2,6-dichloropyrimidine-4-carboxylate (1 g, 4.831 mmol, 1 equiv), (3R)-3-methylmorpholine (0.54 g, 5.314 mmol, 1.1 equiv), TEA (0.64 g, 6.280 mmol, 1.3 equiv), DCM (10 mL). The resulting solution was stirred overnight at room temperature. The resulting mixture was concentrated and applied onto a silica gel column with EA/PE (5:95). This resulted in 1.1 g (83.62%) of methyl 2-chloro-6-[(3R)-3-methylmorpholin-4-yl]pyrimidine-4-carboxylate as a off-white solid. LC-MS-BLV-CY-212-1: (ES, m/z): 272 [M+H]$^+$. H-NMR-BLV-CY-212-1: (300 MHz, d$_6$-DMSO, ppm): δ 7.30 (s, 1H), 4.45 (br, 1H), 4.09 (br, 1H), 3.94 (dd, J=11.4, 3.3 Hz, 1H), 3.87 (s, 3H), 3.72 (d, J=11.7 Hz, 1H), 3.60 (dd, J=11.7, 3.3 Hz, 1H), 3.48 (td, J=12.0, 3.0 Hz, 1H), 3.24 (t, J=12.6 Hz, 1H), 1.23 (d, J=6.6 Hz, 3H).

Synthesis of 2-[2-chloro-6-[(3R)-3-methylmorpholin-4-yl]pyrimidin-4-yl]propan-2-ol: Into a 25-mL 3-necked round-bottom flask purged and maintained with an inert atmosphere of nitrogen, was placed methyl 2-chloro-6-[(3R)-3-methylmorpholin-4-yl]pyrimidine-4-carboxylate (100 mg, 0.368 mmol, 1 equiv). This was followed by the addition of THF (3 mL) stirred for 5 min at −60° C. To this was added chloro(methyl)magnesium (68.81 mg, 0.92 mmol, 2.5 equiv) dropwise with stirring at −60° C. The resulting solution was stirred for 30 min at −60° C. The reaction was then quenched by the addition of 20 mL of NH$_4$Cl solution. The resulting solution was extracted with 2×20 mL of ethyl acetate and the combined organic layer was washed with brine (25 mL), dried (Na$_2$SO$_4$), filtered and concentrated. The residue was applied onto a silica gel column with EA:PE (20:80). This resulted in 60 mg (60%) of 2-[2-chloro-6-[(3R)-3-methylmorpholin-4-yl]pyrimidin-4-yl]propan-2-ol as a white solid. LC-MS-BLV-CY-212-2: (ES, m/z): 272 [M+H]$^+$. H-NMR-BLV-CY-212-2: (300 MHz, d$_6$-DMSO, ppm): δ 6.87 (s, 1H), 5.32 (s, 1H), 4.33 (br.s, 1H), 3.94 (td, J=11.1, 3.6 Hz, 2H), 3.71 (d, J=11.7 Hz, 1H), 3.58 (dd, J=11.4, 3.0 Hz, 1H), 3.43 (td, J=12.0, 2.7 Hz, 1H), 3.18 (td, J=12.9, 4.2 Hz, 1H), 1.35 (s, 6H), 1.20 (d, J=6.0 Hz, 3H).

Synthesis of 2-[6-[(3R)-3-methylmorpholin-4-yl]-2-[1H-pyrrolo[2,3-b]pyridin-4-yl]pyrimidin-4-yl]propan-2-ol: Into a 8-mL microwave and maintained with an inert atmosphere of nitrogen, was placed 2-[2-chloro-6-[(3R)-3-methylmorpholin-4-yl]pyrimidin-4-yl]propan-2-ol (60 mg, 0.221 mmol, 1 equiv), 4-(4,4,5,5-tetramethyl-1,3,2-dioxaborolan-2-yl)-1H-pyrrolo[2,3-b]pyridine (91.62 mg, 0.375 mmol, 1.7 equiv), PdCl$_2$(PPh$_3$)$_2$ (30.99 mg, 0.044 mmol, 0.2 equiv), Na$_2$CO$_3$ (46.80 mg, 0.442 mmol, 2.0 equiv), DME (2.0 mL), H$_2$O (1.0 mL). The resulting solution was stirred for 40 min at 90° C. The solids were filtered out. The combined organic layer was purified by Prep-HPLC. This resulted in 33 mg (42.22%) of 2-[6-[(3R)-3-methylmorpholin-4-yl]-2-[1H-pyrrolo[2,3-b]pyridin-4-yl]pyrimidin-4-yl]propan-2-ol as a white solid. LC-MS-BLV-CY-212-0: (ES, m/z): 354 [M+H]$^+$. H-NMR-BLV-CY-212-0: (300 MHz, d$_6$-DMSO, ppm): δ 11.75 (s, 1H), 8.33 (d, J=5.1 Hz, 1H), 8.00 (d, J=5.1 Hz, 1H), 7.58 (d, J=3.6 Hz, 1H), 7.25 (d, J=3.6 Hz, 1H), 6.96 (s, 1H), 5.31 (s, 1H), 4.56 (br.s, 1H), 4.16 (d, J=12.6 Hz, 1H), 4.02 (dd, J=11.4, 3.3 Hz, 1H), 3.81 (d, J=11.4 Hz, 1H), 3.68 (dd, J=11.1, 2.7 Hz, 1H), 3.52 (td, J=12.0, 2.7 Hz, 1H), 3.27 (td, J=12.9, 4.2 Hz, 1H), 1.52 (s, 6H), 1.27 (d, J=8.1 Hz, 3H).

Example CY-223: Preparation of (3R)-3-methyl-4-(2-[1H-pyrrolo[2,3-b]pyridin-4-yl]pyrimidin-4-yl)morpholine Synthesis of (3R)-4-(2-chloropyrimidin-4-yl)-3-methylmorpholine: Into a 50-mL round-bottom flask, was placed 2,4-dichloropyrimidine (500 mg, 3.356 mmol, 1 equiv), DCM (10 mL), DMF (15 mL), (3R)-3-methylmorpholine (340 mg, 3.361 mmol, 1.00 equiv), TEA (440 mg, 4.348 mmol, 1.30 equiv). The resulting solution was stirred for 15 hr at room temperature. The resulting solution was diluted with 100 mL of H$_2$O. The resulting solution was extracted with 3×100 mL of ethyl acetate. The organic layer was concentrated and applied onto a silica gel column with ethyl acetate/petroleum ether (1/2-1/1). This resulted in 350 mg (48.80%) of (3R)-4-(2-chloropyrimidin-4-yl)-3-methylmorpholine as colorless oil. LC-MS-BLV-CY-223-1: (ES, m/z): 214 [M+H]$^+$. H-NMR-BLV-CY-223-1: (300 MHz, CDCl$_3$, ppm): δ 8.09 (d, J=6.3 Hz, 1H), 6.37 (d, J=6.3 Hz, 1H), 4.30 (br s, 1H), 4.03 (dd, J=11.4, 3.9 Hz, 2H), 3.81 (d, J=11.4 Hz, 1H), 3.71 (dd, J=11.7, 3.0 Hz, 1H), 3.56 (td, J=12.3, 3.3 Hz, 1H), 3.29 (td, J=12.9, 3.6 Hz, 1H), 1.34 (d, J=6.9 Hz, 3H).

Synthesis of (3R)-3-methyl-4-(2-[1H-pyrrolo[2,3-b]pyridin-4-yl]pyrimidin-4-yl)morpholine Into a 30-mL microwave tube purged and maintained with an inert atmosphere of nitrogen, was placed (3R)-4-(2-chloropyrimidin-4-yl)-3-methylmorpholine (150 mg, 0.702 mmol, 1 equiv), DME (10 mL), 4-(4,4,5,5-tetramethyl-1,3,2-dioxaborolan-2-yl)-1H-pyrrolo[2,3-b]pyridine (257 mg, 1.053 mmol, 1.50 equiv), Pd(dppf)Cl$_2$.CH$_2$Cl$_2$ (57 mg, 0.070 mmol, 0.10 equiv), Na$_2$CO$_3$ (150 mg, 1.415 mmol, 2.02 equiv), H$_2$O (2.5 mL). The final reaction mixture was irradiated with microwave radiation for 30 min at 90° C. The resulting mixture was concentrated. The crude product was purified by Flash-Prep-HPLC with the following conditions (IntelFlash-1): Column, C18 silica gel; mobile phase, 0.05% HCOOH/CH$_3$CN=55% increasing to 0.05% HCOOH/CH$_3$CN=65%; Detector, 220 nm. This resulted in 40 mg (19.32%) of (3R)-3-methyl-4-(2-[1H-pyrrolo[2,3-b]pyridin-4-yl]pyrimidin-4-yl)morpholine as a light yellow solid. LC-MS-BLV-CY-223-0: (ES, m/z): 296 [M+H]$^+$. H-NMR-BLV-CY-223-0: (300 MHz, CDCl$_3$, ppm): δ 9.91 (s, 1H), 8.46 (d, J=6.0 Hz, 1H), 8.41 (d, J=5.1 Hz, 1H), 8.07 (d, J=5.1 Hz, 1H), 7.45 (d, J=3.3 Hz, 1H), 7.36 (d, J=3.3 Hz, 1H), 6.48 (d, J=6.3 Hz, 1H), 4.49 (br s, 1H), 4.18 (d, J=12.9 Hz, 1H), 4.09 (dd, J=11.4, 3.6 Hz, 1H), 3.87 (d, J=11.4 Hz, 1H), 3.78

(dd, J=11.4, 3.0 Hz, 1H), 3.64 (td, J=12.0, 3.0 Hz, 1H), 3.38 (td, J=12.9, 3.9 Hz, 1H), 1.39 (d, J=6.9 Hz, 3H).

Example CY-224: Preparation of (3R)-3-methyl-4-(6-methyl-2-[1H-pyrrolo[2,3-b]pyridin-4-yl]pyrimidin-4-yl)-morpholine Synthesis of (3R)-4-(2-chloro-6-methylpyrim-idin-4-yl)-3-methylmorpholine: Into a 50-mL round-bottom flask, was placed 2,4-dichloro-6-methylpyrimidine (500 mg, 3.067 mmol, 1 equiv), DMF (15 mL), DCM (25 mL), (3R)-3-methylmorpholine (310 mg, 3.067 mmol, 1.00 equiv), TEA (405 mg, 4.002 mmol, 1.30 equiv). The resulting solution was stirred for 5 hr at 80° C. in an oil bath. The resulting solution was diluted with 150 mL of $H_2O$. The resulting solution was extracted with 3×100 mL of ethyl acetate. The organic layer was concentrated and applied onto a silica gel column with ethyl acetate/petroleum ether (1/2-1/1). This resulted in 240 mg (34.36%) of (3R)-4-(2-chloro-6-methylpyrim-idin-4-yl)-3-methylmorpholine as a light yellow solid. LC-MS-BLV-CY-224-1: (ES, m/z): 228 [M+H]$^+$. H-NMR-BLV-CY-224-1: (300 MHz, CDCl$_3$, ppm): δ 6.22 (s, 1H), 4.30 (s, 1H), 4.01 (dd, J=11.4, 3.6 Hz, 2H), 3.79 (d, J=11.4 Hz, 1H), 3.69 (dd, J=11.7, 3.0 Hz, 1H), 3.55 (td, J=12.3, 3.0 Hz, 1H), 3.27 (td, J=12.9, 3.6 Hz, 1H), 2.37 (s, 3H), 1.32 (d, J=6.9 Hz, 3H).

Synthesis of (3R)-3-methyl-4-(6-methyl-2-[1H-pyrrolo[2,3-b]pyridin-4-yl]pyrimidin-4-yl)-morpholine: Into a 30-mL microwave tube purged and maintained with an inert atmosphere of nitrogen, was placed (3R)-4-(2-chloro-6-methylpyrimidin-4-yl)-3-methylmorpholine (150 mg, 0.659 mmol, 1 equiv), DME (10 mL), 4-(4,4,5,5-tetramethyl-1,3,2-dioxaborolan-2-yl)-1H-pyrrolo[2,3-b]pyridine (241 mg, 0.987 mmol, 1.50 equiv), Pd(dppf)Cl$_2$ (43 mg, 0.05 mmol, 0.08 equiv), Na$_2$CO$_3$ (141 mg, 1.330 mmol, 2.02 equiv), H$_2$O (2.5 mL). The final reaction mixture was irradiated with microwave radiation for 30 min at 90° C. The resulting mixture was concentrated. The crude product was purified by Flash-Prep-HPLC with the following conditions (Intel-Flash-1): Column, C18 silica gel; mobile phase, 0.05% HCOOH/CH$_3$CN=45% increasing to 0.05% HCOOH/CH$_3$CN=55%; Detector, 220 nm. This resulted in 42 mg (20.69%) of (3R)-3-methyl-4-(6-methyl-2-[1H-pyrrolo[2,3-b]pyridin-4-yl]pyrimidin-4-yl)-morpholine as a light yellow solid. LC-MS-BLV-CY-224-0: (ES, m/z): 310 [M+H]$^+$. H-NMR-BLV-CY-224-0: (300 MHz, CDCl$_3$, ppm): δ 9.89 (s, 1H), 8.38 (d, J=5.1 Hz, 1H), 8.08 (d, J=5.4 Hz, 1H), 7.44 (d, J=3.3 Hz, 1H), 7.38 (d, J=3.3 Hz, 1H), 6.35 (s, 1H), 4.49 (s, 1H), 4.16 (d, J=11.4 Hz, 1H), 4.08 (dd, J=11.4, 3.6 Hz, 1H), 3.86 (d, J=11.4 Hz, 1H), 3.77 (dd, J=11.4, 3.0 Hz, 1H), 3.63 (td, J=12.0, 3.0 Hz, 1H), 3.36 (td, J=12.6, 3.9 Hz, 1H), 2.52 (s, 3H), 1.38 (d, J=6.9 Hz, 3H).

Example CY-225: Preparation of (3R)-3-methyl-4-[6-(propan-2-yl)-2-[1H-pyrrolo[2,3-b]pyridin-4-yl]pyrimidin-4-yl]morpholine Synthesis of 2,4-dichloro-6-(propan-2-yl)pyrimidine: Into a 500-mL 3-necked round-bottom flask, was placed 2,4,6-trichloropyrimidine (1 g, 5.452 mmol, 1 equiv). This was followed by the addition of THF (20 mL) stirred for −20° C. To this was added chloro(propan-2-yl)magnesium (5.46 mL, 2.0 equiv), CuI (52.92 mg, 0.273 mmol, 0.05 equiv) at −20° C. The reaction solution was stirred for 1 hr at 0° C. The reaction was then quenched by the addition of 75 mL of NH$_4$Cl. The resulting solution was extracted with 100 mL of ethyl acetate. The combined organic layer dried over anhydrous sodium sulfate, filtered and concentrated. The residue was applied onto a silica gel column with ethyl EA:PE (2:98). This resulted in 0.4 g (38.31%) of 2,4-dichloro-6-(propan-2-yl)pyrimidine as light yellow oil. LC-MS-BLV-CY-225-1: (ES, m/z): 191 [M+H]$^+$.

Synthesis of (3R)-4-[2-chloro-6-(propan-2-yl)pyrimidin-4-yl]-3-methylmorpholine: Into a 50-mL round-bottom flask, was placed 2,4-dichloro-6-(propan-2-yl)pyrimidine (300 mg, 1.579 mmol, 1 equiv), (3R)-3-methylmorpholine (0.174 g, 1.723 mmol, 1.09 equiv), TEA (0.24 g, 2.369 mmol, 1.50 equiv), EtOH (6 mL). The resulting solution was stirred for overnight at 70° C. The reaction mixture was cooled. The resulting mixture was concentrated and applied onto a silica gel column with EA:PE=(1:10). This resulted in 161 mg (40%) of (3R)-4-[2-chloro-6-(propan-2-yl)pyrimidin-4-yl]-3-methylmorpholine as colorless oil. LC-MS-BLV-CY-225-2: (ES, m/z): 256 [M+H]$^+$. H-NMR-BLV-CY-225-2: (300 MHz, d$_6$-DMSO, ppm): δ 6.63 (s, 1H), 4.38 (br, 1H), 4.05-3.97 (m, 1H), 3.94 (dd, J=11.4, 3.6 Hz, 1H), 3.70 (d, J=11.7 Hz, 1H), 3.57 (dd, J=11.7, 3.0 Hz, 1H), 3.40 (td, J=12.3, 3.0 Hz, 1H), 3.18 (td, J=13.2, 3.9 Hz, 1H), 2.83-2.74 (m, 1H), 1.19-1.16 (m, 9H).

Synthesis of (3R)-3-methyl-4-[6-(propan-2-yl)-2-[1H-pyrrolo[2,3-b]pyridin-4-yl]pyrimidin-4-yl]morpholine: Into a 8-mL microwave and maintained with an inert atmosphere of nitrogen, was placed (3R)-4-[2-chloro-6-(propan-2-yl)pyrimidin-4-yl]-3-methylmorpholine (140 mg, 0.574 mmol, 1 equiv), 4-(4,4,5,5-tetramethyl-1,3,2-dioxaborolan-2-yl)-1H-pyrrolo[2,3-b]pyridine (213.8 mg, 0.876 mmol, 1.6 equiv), Pd(dppf)Cl$_2$ (44.5 mg, 0.055 mmol, 0.1 equiv), Na$_2$CO$_3$ (116.04 mg, 1.095 mmol, 2.0 equiv), DME (6 mL), H$_2$O (1.5 mL). The resulting solution was stirred for 1 hr at 90° C. The reaction mixture was cooled. The solids were filtered out and the filtrate was purified by Prep-HPLC. This resulted in 100 mg (24.36%) of (3R)-3-methyl-4-[6-(propan-2-yl)-2-[1H-pyrrolo[2,3-b]pyridin-4-yl]pyrimidin-4-yl]morpholine as a light yellow solid. LC-MS-BLV-CY-225-0: (ES, m/z): 338 [M+H]$^+$. H-NMR-BLV-CY-225-0: (300 MHz, d$_6$-DMSO, ppm): δ 11.72 (s, 1H), 8.32 (d, J=5.1 Hz, 1H), 7.99 (d, J=4.8 Hz, 1H), 7.57 (t, J=5.4 Hz, 1H), 7.29 (t, J=5.4 Hz, 1H), 6.66 (s, 1H), 4.59 (br.s, 1H), 4.18 (d, J=13.5 Hz, 1H), 4.00 (dd, J=11.7, 3.6 Hz, 1H), 3.79 (d, J=11.4 Hz, 1H), 3.66 (dd, J=11.4, 3.0 Hz, 1H), 3.52 (td, J=12.3, 2.7 Hz, 1H), 3.24 (td, J=13.2, 4.2 Hz, 1H), 3.00-2.91 (m, 1H), 1.31 (d, J=6.9 Hz, 6H), 1.26 (d, J=6.6 Hz, 3H).

Example CY-226: Preparation of (3R)-3-methyl-4-(2-[1H-pyrrolo[2,3-b]pyridin-4-yl]-6-(trifluoromethyl) pyrimidin-4-yl)morpholine Synthesis of (3R)-4-[2-chloro-6-(trifluoromethyl)pyrimidin-4-yl]-3-methylmorpholine: Into a 50-mL round-bottom flask, was placed 2,4-dichloro-6-(trifluoromethyl)pyrimidine (500 mg, 2.304 mmol, 1 equiv), DCM (15 mL), DMF (15 mL), (3R)-3-methylmorpholine (235 mg, 2.323 mmol, 1.01 equiv), TEA (305 mg, 3.014 mmol, 1.31 equiv). The resulting solution was stirred for 15 hr at room temperature. The resulting solution was diluted with 150 mL of H$_2$O. The resulting solution was extracted with 3×100 mL of ethyl acetate. The organic layer was concentrated and applied onto a silica gel column with ethyl acetate/petroleum ether (1/2-1/1). This resulted in 400 mg (61.63%) of (3R)-4-[2-chloro-6-(trifluoromethyl)pyrimidin-4-yl]-3-methylmorpholine as a light yellow solid. LC-MS-BLV-CY-226-1: (ES, m/z): 282 [M+H]$^+$. H-NMR-BLV-CY-226-1: (300 MHz, CDCl$_3$, ppm): δ 6.67 (s, 1H), 4.35 (br s, 1H), 4.04 (dd, J=11.4, 3.6

Hz, 2H), 3.82 (d, J=11.7 Hz, 1H), 3.70 (dd, J=11.7, 3.0 Hz, 1H), 3.56 (td, J=12.0, 3.0 Hz, 1H), 3.36 (td, J=12.6, 3.3 Hz, 1H), 1.37 (d, J=6.9 Hz, 3H).

Synthesis of (3R)-3-methyl-4-(2-[1H-pyrrolo[2,3-b]pyridin-4-yl]-6-(trifluoromethyl) pyrimidin-4-yl)morpholine: Into a 20-mL microwave tube purged and maintained with an inert atmosphere of nitrogen, was placed (3R)-4-[2-chloro-6-(trifluoromethyl)pyrimidin-4-yl]-3-methylmorpholine (150 mg, 0.533 mmol, 1 equiv), DME (2 mL), 4-(4,4,5,5-tetramethyl-1,3,2-dioxaborolan-2-yl)-1H-pyrrolo[2,3-b]pyridine (195 mg, 0.799 mmol, 1.50 equiv), Pd(dppf)Cl$_2$.CH$_2$Cl$_2$ (37 mg, 0.045 mmol, 0.09 equiv), Na$_2$CO$_3$ (114 mg, 1.076 mmol, 2.02 equiv), H$_2$O (0.5 mL). The final reaction mixture was irradiated with microwave radiation for 0.5 hr at 90° C. The resulting mixture was concentrated. The crude product was purified by Flash-Prep-HPLC with the following conditions (IntelFlash-1): Column, C18 silica gel; mobile phase, 0.05% HCOOH/CH$_3$CN=40% increasing to 0.05% HCOOH/CH$_3$CN=50%; Detector, 254 nm & 220 nm. This resulted in 35 mg (18.13%) of (3R)-3-methyl-4-(2-[1H-pyrrolo[2,3-b]pyridin-4-yl]-6-(trifluoromethyl) pyrimidin-4-yl) morpholine as a light yellow solid. LC-MS-BLV-CY-226-0: (ES, m/z): 364 [M+H]$^+$. H-NMR-BLV-CY-226-0: (300 MHz, CDCl$_3$, ppm): δ 9.95 (s, 1H), 8.45 (d, J=5.1 Hz, 1H), 8.11 (d, J=4.8 Hz, 1H), 7.49 (d, J=3.6 Hz, 1H), 7.42 (d, J=3.3 Hz, 1H), 6.77 (s, 1H), 4.52 (br s, 1H), 4.23 (d, J=12.3 Hz, 1H), 4.11 (dd, J=11.4, 3.9 Hz, 1H), 3.89 (d, J=11.7 Hz, 1H), 3.79 (dd, J=11.7, 3.0 Hz, 1H), 3.65 (td, J=12.0, 3.0 Hz, 1H), 3.45 (td, J=12.9, 3.6 Hz, 1H), 1.43 (d, J=6.9 Hz, 3H).

Example CY-227: Preparation of 4-[4-methoxy-6-[(3R)-3-methylmorpholin-4-yl]pyrimidin-2-yl]-1H-indole Synthesis of (3R)-4-(2-chloro-6-methoxypyrimidin-4-yl)-3-methylmorpholine: Into a 50-mL round-bottom flask, was placed 2,4-dichloro-6-methoxypyrimidine (500 mg, 2.809 mmol, 1 equiv), (3R)-3-methylmorpholine (312.54 mg, 3.090 mmol, 1.10 equiv), TEA (567.42 mg, 5.618 mmol, 2.00 equiv), EtOH (10 mL). The resulting solution was stirred for overnight at 70° C. The resulting mixture was concentrated and applied onto a silica gel column with EA:PE (5:95). This resulted in 240 mg (35.06%) of (3R)-4-(2-chloro-6-methoxypyrimidin-4-yl)-3-methylmorpholine as a white solid. LC-MS-BLV-CY-227-1: (ES, m/z): 244 [M+H]$^+$. H-NMR-BLV-CY-227-1: (300 MHz, d$_6$_DMSO, ppm): δ 6.17 (s, 1H), 4.54 (br.s, 1H), 4.18 (d, J=12.0 Hz, 1H), 3.92-3.85 (m, 4H), 3.69 (d, J=11.7 Hz, 1H), 3.54 (dd, J=11.4, 2.7 Hz, 1H), 3.40 (td, J=12.0, 3.0 Hz, 1H), 3.16 (td, J=13.2, 3.6 Hz, 1H), 1.20 (d, J=6.3 Hz, 3H).

Synthesis of 4-[4-methoxy-6-[(3R)-3-methylmorpholin-4-yl]pyrimidin-2-yl]-1H-indole: Into a 8-mL microwave purged and maintained with an inert atmosphere of nitrogen, was placed (3R)-4-(2-chloro-6-methoxypyrimidin-4-yl)-3-methylmorpholine (100 mg, 0.410 mmol, 1 equiv), Pd(dppf)Cl$_2$ (33.36 mg, 0.041 mmol, 0.1 equiv), 4-(4,4,5,5-tetramethyl-1,3,2-dioxaborolan-2-yl)-1H-pyrrolo[2,3-b]pyridine (160.27 mg, 0.657 mmol, 1.6 equiv), Na$_2$CO$_3$ (86.99 mg, 0.821 mmol, 2.0 equiv), DME (3 mL), H$_2$O (0.5 mL). The resulting solution was stirred for 40 min at 90° C. The crude product was purified by Prep-HPLC. This resulted in 30 mg (22.53%) of 4-[4-methoxy-6-[(3R)-3-methylmorpholin-4-yl]pyrimidin-2-yl]-1H-indole as a light yellow solid. LC-MS-BLV-CY-227-0: (ES, m/z): 326 [M+H]$^+$. H-NMR-BLV-CY-227-0: (300 MHz, d$_6$_DMSO, ppm): δ 11.97 (s, 1H), 8.34 (d, J=5.1 Hz, 1H), 7.63 (d, J=5.1 Hz, 2H), 6.99 (dd, J=5.1 Hz, 1.8 Hz, 1H), 6.73 (s, 1H), 4.74 (dd, J=6.9 Hz, 2.4 Hz, 1H), 4.38 (d, J=13.2 Hz, 1H), 4.00-3.93 (m, 4H), 3.77 (d, J=11.1 Hz, 1H), 3.64 (dd, J=11.4, 3.3 Hz, 1H), 3.49 (td, J=12.0, 2.7 Hz, 1H), 3.27 (td, J=13.2, 3.6 Hz, 1H), 1.28 (d, J=6.9 Hz, 3H).

Example CY-228: Preparation of 6-[(3R)-3-methylmorpholin-4-yl]-2-[1H-pyrrolo[2,3-b]pyridin-4-yl]pyrimidine-4-carbonitrile Synthesis of 2-chloro-6-[(3R)-3-methylmorpholin-4-yl]pyrimidin-4-amine: Into a 25-mL round-bottom flask, was placed 2,6-dichloropyrimidin-4-amine (0.3 g, 1.840 mmol, 1 equiv), (3R)-3-methylmorpholine (0.20 g, 1.977 mmol, 1.1 equiv), Cs$_2$CO$_3$ (1.20 g, 3.681 mmol, 2.0 equiv), DMF (4 mL). The resulting solution was stirred for overnight at 80° C. The reaction mixture was cooled. The reaction was then quenched by the addition of 10 mL of water. The resulting solution was extracted with 2×10 mL of ethyl acetate. The combined organic layer was washed with brine (15 ml×2), dried (Na$_2$SO$_4$), filtered and concentrated. The residue was applied onto a silica gel column with ethyl EA:PE (1:10). This resulted in 40 mg (9.53%) of 2-chloro-6-[(3R)-3-methylmorpholin-4-yl]pyrimidin-4-amine as a white solid. LC-MS-BLV-CY-228-1: (ES, m/z): 229 [M+H]$^+$. H-NMR-BLV-CY-225-2: (300 MHz, d$_6$_DMSO, ppm): δ 6.66 (s, 2H), 5.46 (s, 1H), 4.11 (brs, 1H), 3.89 (dd, J=11.7, 3.9 Hz, 1H), 3.72-3.66 (m, 2H), 3.55 (d, J=11.4, 3.0 Hz, 1H), 3.41 (td, J=11.7, 3.0 Hz, 1H), 3.04 (td, J=12.0, 3.6 Hz, 1H), 1.13 (d, J=6.9 Hz, 3H).

Synthesis of 6-[(3R)-3-methylmorpholin-4-yl]-2-[1H-pyrrolo[2,3-b]pyridin-4-yl]pyrimidine-4-carbonitrile: Into a 8-mL microwave and maintained with an inert atmosphere of nitrogen, was placed 2-chloro-6-[(3R)-3-methylmorpholin-4-yl]pyrimidine-4-carbonitrile (40 mg, 0.175 mmol, 1 equiv), 4-(4,4,5,5-tetramethyl-1,3,2-dioxaborolan-2-yl)-1H-pyrrolo[2,3-b]pyridine (65.64 mg, 0.263 mmol, 1.6 equiv), Pd(dppf)Cl$_2$ (13.62 mg, 0.018 mmol, 0.1 equiv), Na$_2$CO$_3$ (37.2 mg, 0.351 mmol, 2.0 equiv), DME (3 mL), H$_2$O (0.5 mL). The resulting solution was stirred for 1 hr at 90° C. The solids were filtered out and the filtrate was purified by Prep-HPLC. This resulted in 30 mg (55.1%) of 6-[(3R)-3-methylmorpholin-4-yl]-2-[1H-pyrrolo[2,3-b]pyridin-4-yl]pyrimidine-4-carbonitrile as a white solid. LC-MS-BLV-CY-228-0: (ES, m/z): 311 [M+H]$^+$. H-NMR-BLV-CY-228-0: (300 MHz, d$_6$_DMSO, ppm): δ 11.99 (s, 1H), 8.41 (d, J=5.1 Hz, 1H), 7.74 (d, J=6.0 Hz, 1H), 7.68-7.67 (m, 1H), 7.08 (s, 1H), 5.77 (s, 1H), 4.43 (brs, 1H), 4.02 (dd, J=11.4, 3.3 Hz, 2H), 3.79 (d, J=11.4 Hz, 1H), 3.66 (dd, J=11.1, 2.7 Hz, 1H), 3.52 (td, J=12.0, 3.0 Hz, 1H), 3.32-3.25 (m, 1H), 1.27 (d, J=6.9 Hz, 3H).

Example CY-229: Preparation of 6-[(3R)-3-methylmorpholin-4-yl]-2-[1H-pyrrolo[2,3-b]pyridin-4-yl]pyrimidine-4-carbonitrile Synthesis of 2-chloro-6-[(3R)-3-methylmorpholin-4-yl]pyrimidine-4-carbonitrile: Into a 100-mL round-bottom flask, was placed 2,6-dichloropyrimidine-4-carbonitrile (500 mg, 2.874 mmol, 1 equiv), (3R)-3-methylmorpholine (319.76 mg, 3.161 mmol, 1.1 equiv), TEA (581.62 mg, 5.748 mmol, 2.0 equiv), DCM (10 mL). The resulting solution was stirred for 1.5 hr at room temperature. The resulting mixture was concentrated and applied onto a silica gel column with EA:PE (1:9). This resulted in 600 mg (87.47%) of 2-chloro-6-[(3R)-3-methylmorpholin-4-yl]pyrimidine-4-carbonitrile as a light yellow solid. LC-MS-BLV- CY-229-1: (ES, m/z): 239 [M+H]$^+$. H-NMR-BLV-CY-229-1: (300 MHz, d$_6$_DMSO, ppm): δ 7.61 (s, 1H), 4.30 (br, 2H), 3.94 (dd, J=11.4, 3.6 Hz, 1H), 3.72 (d, J=11.7 Hz, 1H), 3.58 (dd, J=11.7, 3.0 Hz, 1H), 3.44 (td, J=12.3, 3.0 Hz, 1H), 3.31-3.26 (m, 1H), 1.25 (d, J=6.6 Hz, 3H).

Synthesis of 6-[(3R)-3-methylmorpholin-4-yl]-2-[1H-pyrrolo[2,3-b]pyridin-4-yl]pyrimidine-4-carbonitrile: Into a 8-mL microwave and maintained with an inert atmosphere of nitrogen, was placed 2-chloro-6-[(3R)-3-methylmorpholin-4-yl]pyrimidine-4-carbonitrile (150 mg, 0.630 mmol, 1 equiv), 4-(4,4,5,5-tetramethyl-1,3,2-dioxaborolan-2-yl)-1H-pyrrolo[2,3-b]pyridine (246.1 mg, 1.008 mmol, 1.6 equiv), Pd(dppf)Cl$_2$ (51.09 mg, 0.063 mmol, 0.1 equiv), Na$_2$CO$_3$ (133.6 mg, 1.262 mmol, 2.0 equiv), DME (6 mL), H$_2$O (1.5 mL). The resulting solution was stirred for 1 hr at 90° C. The solids were filtered out and the filtrate was purified by Prep-HPLC. This resulted in 50 mg (24.9%) of 6-[(3R)-3-methylmorpholin-4-yl]-2-[1H-pyrrolo[2,3-b]pyridin-4-yl]pyrimidine-4-carbonitrile as a white solid. LC-MS-BLV-CY-229-0: (ES, m/z): 321 [M+H]$^+$. H-NMR-BLV-CY-229-0: (300 MHz, d$_6$_DMSO, ppm): δ 11.86 (s, 1H), 8.36 (d, J=6.0 Hz, 1H), 7.95 (d, J=5.1 Hz, 1H), 7.63 (t, J=3.0 Hz, 1H), 7.55 (s, 1H), 7.18-7.16 (m, 1H), 4.62 (br, 1H), 4.27 (br, 1H), 4.01 (dd, J=11.1, 3.0 Hz, 1H), 3.81 (d, J=11.7 Hz, 1H), 3.68 (dd, J=11.7, 3.0 Hz, 1H), 3.53 (td, J=12.0, 2.7 Hz, 1H), 3.36 (dd, J=12.9, 3.6 Hz, 1H), 1.31 (d, J=6.6 Hz, 3H).

Example CY-230-0: Preparation of (R)-4-(2-(1H-pyrrolo[2,3-b]pyridin-4-yl)-6-(1,1,1-trifluoro-2-methylpropan-2-yl)pyrimidin-4-yl)-3-methylmorpholine Synthesis of 1H-pyrrolo[2,3-b]pyridine-4-carbonitrile. Into a 100-mL round-bottom flask purged and maintained with an inert atmosphere of nitrogen, was placed 4-chloro-1H-pyrrolo[2,3-b]pyridine (3 g, 19.662 mmol, 1 equiv), Pd$_2$(dba)$_3$ (0.90 g, 0.983 mmol, 0.05 equiv), dppf (1086.05 mg, 1.966 mmol, 0.1 equiv), Zn (128.61 mg, 1.966 mmol, 0.1 equiv), Cs$_2$CO$_3$ (12.81 g, 39.324 mmol, 2 equiv), Zn(CN)$_2$ (1270.04 mg, 10.814 mmol, 0.55 equiv), DMF (20 mL). The resulting solution was stirred for 10 hr at 120° C. in an oil bath. The resulting solution was diluted with 200 mL of water. The solids were collected by filtration. The crude product was purified by re-crystallization from EA (20 ml). This resulted in 1.5 g (52.5%) of 1H-pyrrolo[2,3-b]pyridine-4-carbonitrile as a grey solid. LC-MS-BLV-CY-230-1: (ES, m/z): 144 [M+H]$^+$. H-NMR-BLV-CY-200-1-2: (300 MHz, d$_6$-DMSO, ppm): δ 12.37 (s, 1H), 8.41 (d, J=4.9 Hz, 1H), 7.84 (d, J=3.5 Hz, 1H), 7.56 (d, J=4.9 Hz, 1H), 6.66 (d, J=3.4 Hz, 1H).

Synthesis of N-hydroxy-1H-pyrrolo[2,3-b]pyridine-4-carboximidamide. Into a 50-mL round-bottom flask purged and maintained with an inert atmosphere of nitrogen, was placed 1H-pyrrolo[2,3-b]pyridine-4-carbonitrile (700 mg, 4.890 mmol, 1 equiv), EtOH (20 mL), hydroxylamine aqueous (5 mL). The resulting solution was stirred for 5 hr at 60° C. in an oil bath. The resulting mixture was concentrated under vacuum. This resulted in 800 mg (92.86%) of N-hydroxy-1H-pyrrolo[2,3-b]pyridine-4-carboximidamide as a white solid. LC-MS-BLV-CY-230-2: (ES, m/z): 177 [M+H]$^+$. H-NMR-BLV-CY-230-2: (300 MHz, d$_6$-DMSO, ppm): δ 12.96 (s, 1H), 11.95 (s, 1H), 8.38 (d, J=5.0 Hz, 1H), 7.77 (s, 1H), 7.67 (t, J=2.9 Hz, 1H), 7.11 (s, 1H), 6.67 (s, 1H), 1.60 (s, 6H).

Synthesis of 1H-pyrrolo[2,3-b]pyridine-4-carboximidamide (AcOH salt). Into a 250-mL round-bottom flask purged and maintained with an inert atmosphere of nitrogen, was placed N-hydroxy-1H-pyrrolo[2,3-b]pyridine-4-carboximidamide (500 mg, 2.838 mmol, 1 equiv), Ac$_2$O (318.70 mg, 3.122 mmol, 1.1 equiv), Pd/C (70 mg), MeOH (100 mL). The flask was evacuated and flushed three times with nitrogen, followed by flushing with hydrogen. The mixture was stirred 4h at room temperature under an atmosphere of hydrogen (balloon). The solids were filtered out. The resulting mixture was concentrated under vacuum. This resulted in 600 mg (95.14%) of 1H-pyrrolo[2,3-b]pyridine-4-carboximidamide; carbonic acid as a grey solid. LC-MS-BLV-CY-230-3: (ES, m/z): 161 [M+H]$^+$. H-NMR-BLV-CY-230-3: (300 MHz, d$_6$-DMSO, ppm): δ 11.99 (s, 1H), 8.42 (d, J=5.0 Hz, 1H), 8.03 (d, J=5.0 Hz, 1H), 7.99 (s, 1H), 7.71 (t, J=3.0 Hz, 1H), 7.28 (dd, J=3.4, 1.9 Hz, 1H), 1.73 (s, 3H).

Synthesis of ethyl 5,5,5-trifluoro-4,4-dimethyl-3-oxopentanoate: Into a solution of 3,3,3-trifluoro-2,2-dimethylpropanoic acid (5 g. 32 mmol) in 20 mL THF was added CDI (5.7 g, 35 mmol) and a catalytic amount of DMAP, stirred for 4 h. A (TMS)ethyl malonate solution was prepped by treating potassium ethyl malonate (5.5 g, 32 mmol) in 20 ml ACN with TMS-Cl (3.8 g, 35 mmol) at rt and stirring for 8 h. The solution was cooled to 0° C. and DBU (9.7 g. 64 mmol) was added and stirred at 0° C. for 0.5 h. The 3,3,3-trifluoro-1-(1H-imidazol-1-yl)-2,2-dimethylpropan-1-one solution was added dropwise to the (TMS)ethyl malonate solution at 0° C., The reaction mixture was stirred for 10 h at rt and was quenched by adding 10% aqueous HCl and extracted with ethyl acetate. The ethyl acetate extract was washed with water. The crude was concentrated and purified by normal column This resulted in 1.5 g (21%) of ethyl 5,5,5-trifluoro-4,4-dimethyl-3-oxopentanoate as a yellow oil. H-NMR-BLV-CY-230-4: (300 MHz, CCl$_3$D, ppm): δ 12.53 (s, 0.5H), 5.26 (s, 0.5H), 4.27-4.18 (m, 3H), 3.66 (s, 2H), 1.45-1.35 (m, 9H), 1.35-1.25 (m, 4.5H).

Synthesis of 2-[1H-pyrrolo[2,3-b]pyridin-4-yl]-6-(1,1,1-trifluoro-2-methylpropan-2-yl)pyrimidin-4-ol. Into a 10-mL sealed tube, was placed ethyl 5,5,5-trifluoro-4,4-dimethyl-3-oxopentanoate (300 mg, 1.326 mmol, 1 equiv), 1H-pyrrolo[2,3-b]pyridine-4-carboximidamide (AcOH salt); (292.09 mg, 1.326 mmol, 1 equiv), Cs$_2$CO$_3$ (1080.33 mg, 3.316 mmol, 2.5 equiv), NMP (8 mL). The final reaction mixture was irradiated with microwave radiation for 2 hr at 145° C. The resulting solution was diluted with 100 mL of water. The pH value of the solution was adjusted to 3 with HCl (6 M). The solids were collected by filtration. The solid was dried in an oven under reduced pressure. This resulted in 200 mg (46.79%) of 2-[1H-pyrrolo[2,3-b]pyridin-4-yl]-6-(1,1,1-trifluoro-2-methylpropan-2-yl)pyrimidin-4-ol as a grey solid. LC-MS-BLV-CY-230-5: (ES, m/z): 323 [M+H]$^+$. H-NMR-BLV-CY-230-5: (300 MHz, d$_6$-DMSO, ppm): δ 13.0 (brs, 1H), 11.94 (s, 1H), 8.38 (d, J=5.0 Hz, 1H), 7.77 (s, 1H), 7.67 (t, J=3.0 Hz, 1H), 7.11 (s, 1H), 6.67 (s, 1H), 1.60 (s, 6H).

Synthesis of 4-(4-chloro-6-(1,1,1-trifluoro-2-methylpropan-2-yl)pyrimidin-2-yl)-1H-pyrrolo[2,3-b]pyridine. Into a 100-mL round-bottom flask, was placed 2-[1H-pyrrolo[2,3-b]pyridin-4-yl]-6-(1,1,1-trifluoro-2-methylpropan-2-yl)pyrimidin-4-ol (180 mg, 0.559 mmol, 1 equiv), DCE (30 mL), DIEA (108.27 mg, 0.838 mmol, 1.5 equiv). This was followed by the addition of POCl$_3$ (1712.72 mg, 11.170 mmol, 20.00 equiv) dropwise with stirring at RT. The resulting solution was stirred for 15 hr at 75° C. in an oil bath. The pH value of the solution was adjusted to 9 with NaHCO$_3$ aqueous. The resulting solution was extracted with 3×30 mL of dichloromethane and the organic layers combined and dried over anhydrous sodium sulfate and concentrated under vacuum. This resulted in 160 mg (84.08%) of 4-chloro-2-

[1H-pyrrolo[2,3-b]pyridin-4-yl]-6-(1,1,1-trifluoro-2-methylpropan-2-yl)pyrimidine as a grey solid. LC-MS-BLV-CY-230-6: (ES, m/z): 341 [M+H]⁺. H-NMR-BLV-CY-230-6: (300 MHz, d₆-DMSO, ppm): δ 11.98 (s, 1H), 8.42 (d, J=5.0 Hz, 1H), 8.03 (d, J=5.0 Hz, 1H), 7.99 (s, 1H), 7.71 (t, J=3.0 Hz, 1H), 7.28 (dd, J=3.4, 1.9 Hz, 1H), 1.72 (s, 6H).

Synthesis of (R)-4-(2-(1H-pyrrolo[2,3-b]pyridin-4-yl)-6-(1,1,1-trifluoro-2-methylpropan-2-yl)pyrimidin-4-yl)-3-methylmorpholine. Into a 25-mL round-bottom flask, was placed 4-chloro-2-[1H-pyrrolo[2,3-b]pyridin-4-yl]-6-(1,1,1-trifluoro-2-methylpropan-2-yl)pyrimidine (100 mg, 0.293 mmol, 1 equiv), (2R)-2-methyl-1-aza-4-nobelacyclohexane (202.01 mg, 0.587 mmol, 2 equiv), DIEA (113.79 mg, 0.880 mmol, 3 equiv), NMP (4 mL). The resulting solution was stirred for 3 hr at 100° C. in an oil bath. The crude product was purified by Flash-Prep-HPLC with the following conditions (IntelFlash-1): Column, C18 silica gel; mobile phase, MeOH/water=20% increasing to MeOH/water=75% within 10 min; Detector, 254 nm. This resulted in 22.7 mg (19.08%) of (3R)-3-methyl-4-(2-[1H-pyrrolo[2,3-b]pyridin-4-yl]-6-(1,1,1-trifluoro-2-methylpropan-2-yl)pyrimidin-4-yl)morpholine as a light brown solid. LC-MS-BLV-CY-230-0: (ES, m/z): 406 [M+H]⁺. H-NMR-BLV-CY-230-0: (300 MHz, d₆-DMSO, ppm): δ 11.78 (s, 1H), 8.34 (d, J=5.0 Hz, 1H), 8.00 (d, J=5.0 Hz, 1H), 7.66-7.55 (m, 1H), 7.33-7.20 (m, 1H), 6.89 (s, 1H), 4.66 (s, 1H), 4.25 (d, J=13.4 Hz, 1H), 4.11-3.95 (m, 1H), 3.81 (d, J=11.4 Hz, 1H), 3.68 (dd, J=11.5, 3.1 Hz, 1H), 3.63-3.47 (m, 1H), 3.30-3.21 (m, 1H), 1.66 (s, 6H), 1.27 (d, J=6.7 Hz, 3H).

Example CY-231: Preparation of (3R)-3-methyl-4-[6-(pyridin-3-yl)-2-[1H-pyrrolo[2,3-b]pyridin-4-yl]pyrimidin-4-yl]morpholine Synthesis of (3R)-3-methyl-4-[2-(methylsulfanyl)-6-(pyridin-3-yl)pyrimidin-4-yl]morpholine: Into a 40-mL microwave tube, was placed (3R)-4-[6-chloro-2-(methylsulfanyl)pyrimidin-4-yl]-3-methylmorpholine (500 mg, 1.925 mmol, 1 equiv), dioxane (5 mL), 3-(4,4,5,5-tetramethyl-1,3,2-dioxaborolan-2-yl)pyridine (592 mg, 2.887 mmol, 1.50 equiv), Pd(dppf)Cl₂ (141 mg, 0.193 mmol, 0.10 equiv), K₂CO₃ (532 mg, 3.849 mmol, 2.00 equiv), H₂O (0.5 mL). The final reaction mixture was irradiated with microwave radiation for 40 min at 100° C. The resulting solution was diluted with 50 mL of H₂O. The resulting solution was extracted with 4×30 mL of ethyl acetate and the organic layers combined and concentrated. The residue was applied onto a silica gel column with ethyl acetate/petroleum ether (1/3-1/1). This resulted in 500 mg (85.90%) of (3R)-3-methyl-4-[2-(methylsulfanyl)-6-(pyridin-3-yl)pyrimidin-4-yl]morpholine as a yellow solid. H-NMR-BLV-CY-231-1: (300 MHz, CDCl₃, ppm): δ 9.19 (s, 1H), 8.71 (s, 1H), 8.36 (d, J=7.8 Hz, 1H), 7.43 (s, 1H), 6.58 (s, 1H), 4.45 (brs, 1H), 4.18-4.06 (m, 2H), 3.85 (d, J=11.4 Hz, 1H), 3.76 (dd, J=11.4, 2.4 Hz, 1H), 3.62 (td, J=12.0, 2.4 Hz, 1H), 3.34 (td, J=12.6, 3.6 Hz, 1H), 2.60 (s, 3H), 1.36 (d, J=6.6 Hz, 3H).

Synthesis of (3R)-4-[2-methanesulfonyl-6-(pyridin-3-yl)pyrimidin-4-yl]-3-methylmorpholine: Into a 50-mL round-bottom flask, was placed (3R)-3-methyl-4-[2-(methylsulfanyl)-6-(pyridin-3-yl)pyrimidin-4-yl]morpholine (400 mg, 1.323 mmol, 1 equiv), DCM (5 mL), mCPBA (571 mg, 3.309 mmol, 2.50 equiv). The resulting solution was stirred for 15 hr at room temperature. The reaction was then quenched by the addition of 50 mL of saturated aqueous NaHCO₃. The resulting solution was extracted with 4×50 mL of dichloromethane and the organic layers combined and concentrated. This resulted in 300 mg (67.82%) of (3R)-4-[2-methanesulfonyl-6-(pyridin-3-yl)pyrimidin-4-yl]-3-methylmorpholine as yellow oil.

Synthesis of 4-[(3R)-3-methylmorpholin-4-yl]-6-(pyridin-3-yl)pyrimidin-2-ol: Into a 50-mL round-bottom flask, was placed (3R)-4-[2-methanesulfonyl-6-(pyridin-3-yl)pyrimidin-4-yl]-3-methylmorpholine (270 mg, 0.807 mmol, 1 equiv), NaOH (3.7 M) (4.8 mL, 17.764 mmol, 22.00 equiv). The resulting solution was stirred for 2 hr at 100° C. in an oil bath. The pH value of the solution was adjusted to 4 with HCl. The crude product was purified by Flash-Prep-HPLC with the following conditions (IntelFlash-1): Column, C18 silica gel; mobile phase, CH₃CN/0.1% HCOOH=32%; Detector, 254 nm & 220 nm. This resulted in 100 mg (45.48%) of 4-[(3R)-3-methylmorpholin-4-yl]-6-(pyridin-3-yl)pyrimidin-2-ol as a light yellow solid. LC-MS-BLV-CY-236-6: (ES, m/z): 273[M+H]⁺. H-NMR-BLV-CY-236-6: (300 MHz, CD₃OD, ppm): δ 9.13-8.60 (m, 2H), 8.21 (d, J=8.1 Hz, 1H), 7.64 (s, 1H), 6.45 (s, 1H), 4.80-4.55 (m, 1H), 4.40-4.10 (m, 1H), 4.00 (dd, J=11.4, 3.0 Hz, 1H), 3.81 (d, J=11.7 Hz, 1H), 3.70 (dd, J=11.7, 2.4 Hz, 1H), 3.56 (td, J=12.0, 2.4 Hz, 1H), 3.40-3.33 (m, 1H), 1.37 (d, J=6.6 Hz, 3H).

Synthesis of Into a 50-mL round-bottom flask, was placed 4-[(3R)-3-methylmorpholin-4-yl]-6-(pyridin-3-yl)pyrimidin-2-ol (85 mg, 0.312 mmol, 1 equiv), POCl₃ (3 mL, 32.185 mmol). The resulting solution was stirred for 3 hr at 100° C. in an oil bath. The reaction was cooled to room temperature and poured into 100 mL of saturated aqueous NaHCO₃. The resulting solution was extracted with 3×60 mL of ethyl acetate and the organic layer was combined and concentrated. The crude product was purified by Flash-Prep-HPLC with the following conditions (IntelFlash-1): Column, C18 silica gel; mobile phase, CH₃CN/0.05% HCOOH=45% increasing to CH₃CN/0.05% HCOOH=55%; Detector, 254 nm & 220 nm. This resulted in 20 mg (22.04%) of (3R)-4-[2-chloro-6-(pyridin-3-yl)pyrimidin-4-yl]-3-methylmorpholine as a yellow solid. LC-MS-BLV-CY-231-5: (ES, m/z): 291 [M+H]⁺. H-NMR-BLV-CY-231-5: (300 MHz, CDCl₃, ppm): δ 9.35-8.62 (m, 2H), 8.36 (d, J=7.5 Hz, 1H), 7.47 (s, 1H), 6.75 (s, 1H), 4.41 (s, 1H), 4.13-4.02 (m, 2H), 3.83 (d, J=11.4 Hz, 1H), 3.73 (dd, J=12.9, 2.7 Hz, 1H), 3.59 (td, J=12.0, 2.7 Hz, 1H), 3.36 (td, J=12.9, 3.3 Hz, 1H), 1.37 (d, J=6.9 Hz, 3H).

Synthesis of (3R)-3-methyl-4-[6-(pyridin-3-yl)-2-[1H-pyrrolo[2,3-b]pyridin-4-yl]pyrimidin-4-yl]morpholine: Into a 20-mL microwave tube purged and maintained with an inert atmosphere of nitrogen, was placed (3R)-4-[2-chloro-6-(pyridin-3-yl)pyrimidin-4-yl]-3-methylmorpholine (20 mg, 0.069 mmol, 1 equiv), DME (4 mL), 4-(4,4,5,5-tetramethyl-1,3,2-dioxaborolan-2-yl)-1H-pyrrolo[2,3-b]pyridine (25 mg, 0.102 mmol, 1.49 equiv), Pd(dppf)Cl₂ (5 mg, 0.007 mmol, 0.10 equiv), K₂CO₃ (19 mg, 0.137 mmol, 2.00 equiv), H₂O (1 mL). The final reaction mixture was irradiated with microwave radiation for 1 hr at 100° C. The crude product was purified by Flash-Prep-HPLC with the following conditions (IntelFlash-1): Column, C18 silica gel; mobile phase, CH₃CN/0.05% NH₃H₂O=55% increasing to CH₃CN/0.05% NH₃H₂O=65% within 15 min; Detector, 254 nm & 220 nm. This resulted in 3.5 mg (39.03%) of (3R)-3-methyl-4-[6-(pyridin-3-yl)-2-[1H-pyrrolo[2,3-b]pyridin-4-yl]pyrimidin-4-yl]morpholine as a yellow solid. LC-MS-BLV-CY-231-0: (ES, m/z): 373 [M+H]⁺. H-NMR-BLV-CY-231-0: (300 MHz, CD₃OD, ppm): δ 9.40 (s, 1H), 8.67 (d, J=5.4 Hz, 2H), 8.50 (brs, 1H), 8.32 (d, J=5.4 Hz, 1H), 8.16 (d, J=5.1 Hz, 1H), 7.64-7.60 (m, 1H), 7.52 (d, J=3.3 Hz, 1H), 7.41 (d, J=3.3 Hz, 1H), 7.25 (s, 1H), 4.79-7.77 (m, 1H), 4.35 (d, J=12.3 Hz, 1H), 4.09 (dd, J=11.4, 3.3 Hz, 1H), 3.89 (d, J=11.7 Hz, 1H), 3.81 (dd, J=11.7, 2.4 Hz, 1H), 3.65 (td, J=11.7, 3.0, 1H), 3.44 (td, J=13.2, 3.9 Hz, 1H), 1.42 (d, J=6.6 Hz, 3H).

Example CY-232: Preparation of (3R)-4-[6-(4,4-difluoropiperidin-1-yl)-2-[1H-pyrrolo[2,3-b]pyridin-4-yl]pyrimidin-4-yl]-3-methylmorpholine Synthesis of methyl (3R)-4-[3-chloro-5-(methylsulfanyl)phenyl]-3-methylmorpholine: Into a 250-mL round-bottom flask, was placed 4,6-dichloro-2-(methylsulfanyl)pyrimidine (10 g, 51.266 mmol, 1 equiv), (3R)-3-methylmorpholine (6.74 g, 66.646 mmol, 1.3 equiv), DIEA (19.88 g, 153.799 mmol, 3.0 equiv), DCM (100 mL). The resulting solution was stirred overnight at 40° C. The resulting mixture was concentrated. The residue was applied onto a silica gel column with ethyl acetate/petroleum ether (1:10). This resulted in 9 g (68.10%) of (3R)-4-[3-chloro-5-(methylsulfanyl)phenyl]-3-methylmorpholine as a white solid. LC-MS-BLV-CY-232-1: (ES, m/z): 260 [M+H]$^+$. H-NMR-BLV-CY-232-1: (300 MHz, CDCl$_3$, ppm): δ 6.15 (s, 1H), 4.26 (brs, 1H), 4.06-3.92 (m, 2H), 3.80 (d, J=11.5 Hz, 1H), 3.70 (dd, J=11.6, 2.9 Hz, 2H), 3.56 (td, J=11.8, 3.1 Hz, 1H), 3.27 (td, J=12.8, 4.0 Hz, 1H), 2.51 (s, 3H), 1.32 (dd, J=6.9, 0.7 Hz, 3H).

Synthesis of methyl (3R)-4-[6-(4,4-difluoropiperidin-1-yl)-2-(methylsulfanyl)pyrimidin-4-yl]-3-methylmorpholine: Into a 40-mL microwave and maintained with an inert atmosphere of nitrogen, was placed (3R)-4-[6-chloro-2-(methylsulfanyl)pyrimidin-4-yl]-3-methylmorpholine (1 g, 3.85 mmol, 1 equiv), 4,4-difluoropiperidine (932.7 mg, 7.70 mmol, 2.0 equiv), Pd$_2$(dba)$_3$ (352.5 mg, 0.38 mmol, 0.10 equiv), XantPhos (445.5 mg, 0.77 mmol, 0.20 equiv), Cs$_2$CO$_3$ (2.5 g, 7.70 mmol, 2.00 equiv), dioxane (10 ml). The resulting solution was stirred for 1 hr at 90° C. The solids were filtered out. The combined organic layer was concentrated. The residue was applied onto a silica gel column with ethyl acetate/petroleum ether (1:3). This resulted in 180 mg (13.57%) of (3R)-4-[6-(4,4-difluoropiperidin-1-yl)-2-(methylsulfanyl)pyrimidin-4-yl]-3-methylmorpholine as a white solid. LC-MS-BLV-CY-232-2: (ES, m/z): 345 [M+H]$^+$. H-NMR-BLV-CY-232-2: (300 MHz, d$_6$-DMSO, ppm): δ 5.73 (s, 1H), 4.42-4.31 (m, 1H), 3.97-3.87 (m, 2H), 3.71-3.68 (m, 5H), 3.56 (dd, J=11.4, 2.9 Hz, 1H), 3.41 (td, J=11.8, 2.8 Hz, 1H), 3.04 (td, J=12.8, 3.6 Hz, 1H), 2.38 (s, 3H), 2.02-1.89 (m, 4H), 1.13 (d, J=6.7 Hz, 3H).

Synthesis of methyl (3R)-4-[6-(4,4-difluoropiperidin-1-yl)-2-[1H-pyrrolo[2,3-b]pyridin-4-yl]pyrimidin-4-yl]-3-methylmorpholine: Into a 40-mL microwave and maintained with an inert atmosphere of nitrogen, was placed (3R)-4-[6-(4,4-difluoropiperidin-1-yl)-2-(methylsulfanyl)pyrimidin-4-yl]-3-methylmorpholine (200 mg, 0.581 mmol, 1 equiv), 4-(4,4,5,5-tetramethyl-1,3,2-dioxaborolan-2-yl)-1H-pyrrolo[2,3-b]pyridine (425.24 mg, 1.742 mmol, 3.0 equiv), Pd(PPh$_3$)$_4$ (335.51 mg, 0.290 mmol, 0.5 equiv), CuMeSal (623.37 mg, 2.903 mmol, 5.0 equiv), dioxane (10 mL). The resulting solution was stirred for 1.5 hr at 110° C. The crude product was purified by Prep-HPLC. This resulted in 12 mg (4.99%) of (3R)-4-[6-(4,4-difluoropiperidin-1-yl)-2-[1H-pyrrolo[2,3-b]pyridin-4-yl]pyrimidin-4-yl]-3-methylmorpholine as a light yellow solid. LC-MS-BLV-CY-232-0: (ES, m/z): 415 [M+H]$^+$. H-NMR-BLV-CY-232-0: (300 MHz, d$_6$-DMSO, ppm): δ 11.72 (s, 1H), 8.30 (d, J=5.0 Hz, 1H), 7.93 (d, J=5.0 Hz, 1H), 7.57-7.53 (m, 1H), 7.15 (dd, J=3.3, 1.9 Hz, 1H), 6.06 (s, 1H), 4.65-4.53 (m, 1H), 4.12 (d, J=12.8 Hz, 1H), 3.98 (dd, J=11.3, 3.3 Hz, 1H), 3.91-3.83 (m, 4H), 3.78 (d, J=11.5 Hz, 1H), 3.66 (dd, J=11.5, 2.7 Hz, 1H), 3.51 (td, J=11.7, 2.7 Hz, 1H), 3.18 (td, J=12.9, 3.7 Hz, 1H), 2.13-1.96 (m, 4H), 1.23 (d, J=6.7 Hz, 3H).

Example CY-233: Preparation of 6-[(3R)-3-methylmorpholin-4-yl]-2-[1H-pyrrolo[2,3-b]pyridin-4-yl]-N-(2,2,2-trifluoroethyl)pyrimidin-4-amine Synthesis of methyl 6-[(3R)-3-methylmorpholin-4-yl]-2-(methylsulfanyl)-N-(2,2,2-trifluoroethyl)pyrimidin-4-amine: Into a 100-mL round-bottom flask purged and maintained with an inert atmosphere of nitrogen, was placed (3R)-4-[6-chloro-2-(methylsulfanyl)pyrimidin-4-yl]-3-methylmorpholine (1 g, 3.850 mmol, 1 equiv), 2,2,2-trifluoroethan-1-amine (1.91 g, 19.249 mmol, 5.0 equiv), Pd$_2$(dba)$_2$ (0.09 g, 0.385 mmol, 0.1 equiv), XantPhos (0.45 g, 0.770 mmol, 0.2 equiv), Cs$_2$CO$_3$ (3.14 g, 9.625 mmol, 2.5 equiv), dioxane (20 mL). The resulting solution was stirred overnight at 85° C. The solids were filtered out. The combined organic layer was concentrated. The residue was applied onto a silica gel column with ethyl acetate/petroleum ether (20:80). This resulted in 300 mg (24.17%) of 6-[(3R)-3-methylmorpholin-4-yl]-2-(methylsulfanyl)-N-(2,2,2-trifluoroethyl)pyrimidin-4-amine as a white solid. LC-MS-BLV-CY-233-1: (ES, m/z): 323 [M+H]$^+$. H-NMR-BLV-CY-233-1: (300 MHz, CDCl$_3$, ppm): δ 5.23 (s, 1H), 4.75 (brs, 1H), 4.27 (brs, 1H), 4.13-3.87 (m, 4H), 3.78 (d, J=11.4 Hz, 1H), 3.71 (dd, J=11.4, 3.0 Hz, 1H), 3.56 (td, J=11.9, 3.1 Hz, 1H), 3.21 (td, J=12.7, 3.9 Hz, 1H), 2.49 (s, 3H), 1.27 (d, J=6.6 Hz, 3H).

Synthesis of methyl 6-[(3R)-3-methylmorpholin-4-yl]-2-[1H-pyrrolo[2,3-b]pyridin-4-yl]-N-(2,2,2-trifluoroethyl)pyrimidin-4-amine: Into a 40-mL microwave and maintained with an inert atmosphere of nitrogen, was placed 6-[(3R)-3-methylmorpholin-4-yl]-2-(methylsulfanyl)-N-(2,2,2-trifluoroethyl)pyrimidin-4-amine (200 mg, 0.620 mmol, 1 equiv), 4-(4,4,5,5-tetramethyl-1,3,2-dioxaborolan-2-yl)-1H-pyrrolo[2,3-b]pyridine (454.35 mg, 1.861 mmol, 3.0 equiv), Pd(PPh$_3$)$_4$ (358.48 mg, 0.310 mmol, 0.5 equiv), CuMeSal (666.05 mg, 3.102 mmol, 5.0 equiv), dioxane (10 ml). The resulting solution was stirred for 1.5 hr at 110° C. The crude product was purified by Prep-HPLC. This resulted in 25 mg (10.2%) of 6-[(3R)-3-methylmorpholin-4-yl]-2-[1H-pyrrolo[2,3-b]pyridin-4-yl]-N-(2,2,2-trifluoroethyl)pyrimidin-4-amine as a light yellow solid. LC-MS-BLV-CY-233-0: (ES, m/z): 393 [M+H]$^+$. H-NMR-BLV-CY-233-0: (300 MHz, CD$_3$OD, ppm): δ 8.27 (d, J=5.1 Hz, 1H), 8.02 (d, J=5.2 Hz, 1H), 7.48 (d, J=3.5 Hz, 1H), 7.31 (d, J=3.5 Hz, 1H), 5.79 (s, 1H), 4.52 (brs, 1H), 4.30 (q, J=9.4 Hz, 2H), 4.09-4.00 (m, 2H), 3.88-3.74 (m, 2H), 3.72-3.57 (m, 1H), 3.31-3.24 (m, 1H), 1.34 (d, J=6.8 Hz, 3H).

Example CY-234: Preparation of (3R)-4-(6-tert-butyl-2-[1H-pyrrolo[2,3-b]pyridin-4-yl]pyrimidin-4-yl)-3-methylmorpholine Synthesis of 4-tert-butyl-2,6-dichloropyrimidine: Into a 250-mL 3-necked round-bottom flask, was placed 2,4,6-trichloropyrimidine (10 g, 54.520 mmol, 1 equiv), CuI (519.16 mg, 2.726 mmol, 0.05 equiv). This was followed by the addition of THF (100 mL) stirred at −10° C. of 5 min. To this was added tert-butyl(chloro)magnesium (27.2 mL) dropwise with stirring at −10° C. The resulting solution was stirred for 1 hr at 0° C. The reaction was then quenched by the addition of 150 mL of NH$_4$Cl. Then water (150 ml) was added and extracted with EtOAc (2×150 ml). The combined organic layer was washed with brine (150 ml), dried (Na$_2$SO$_4$), filtered and concentrated. This resulted in 8 g (71.55%) of 4-tert-butyl-2,6-dichloropyrimidine as a light yellow solid. LC-MS-BLV-CY-234-1: (ES, m/z): 205 [M+H]$^+$.

Synthesis of (3R)-4-(6-tert-butyl-2-chloropyrimidin-4-yl)-3-methylmorpholine: Into a 100-mL round-bottom flask, was placed 4-tert-butyl-2,6-dichloropyrimidine (1 g, 4.876 mmol, 1 equiv), (3R)-3-methylmorpholine (0.49 g, 4.876 mmol, 1.0 equiv), TEA (0.99 g, 9.752 mmol, 2.0 equiv), EtOH (15 mL). The resulting solution was stirred overnight at 50° C. The resulting mixture was concentrated. The residue was applied onto a silica gel column with ethyl acetate/petroleum ether (15:85). This resulted in 600 mg (45.61%) of (3R)-4-(6-tert-butyl-2-chloropyrimidin-4-yl)-3-methylmorpholine as colorless oil. LC-MS-BLV-CY-234-2: (ES, m/z): 270 [M+H]$^+$.

Synthesis of (3R)-4-(6-tert-butyl-2-[1H-pyrrolo[2,3-b]pyridin-4-yl]pyrimidin-4-yl)-3-methylmorpholine: Into a 40-mL microwave and maintained with an inert atmosphere of nitrogen, was placed (3R)-4-(6-tert-butyl-2-chloropyrimidin-4-yl)-3-methylmorpholine (200 mg, 0.741 mmol, 1 equiv), 4-(4,4,5,5-tetramethyl-1,3,2-dioxaborolan-2-yl)-1H-pyrrolo[2,3-b]pyridine (289.55 mg, 1.186 mmol, 1.6 equiv), Pd(dppf)Cl$_2$ (120.70 mg, 0.148 mmol, 0.2 equiv), Na$_2$CO$_3$ (157.15 mg, 1.483 mmol, 2.0 equiv), DME (8 mL), H$_2$O (2 mL). The resulting solution was stirred for 1 hr at 90° C. The crude product was purified by Prep-HPLC. This resulted in 41 mg (15.74%) of (3R)-4-(6-tert-butyl-2-[1H-pyrrolo[2,3-b]pyridin-4-yl]pyrimidin-4-yl)-3-methylmorpholine as a white solid. LC-MS-BLV-CY-234-0: (ES, m/z): 352 [M+H]$^+$. H-NMR-BLV-CY-234-0: (300 MHz, d$_6$-DMSO, ppm): δ 11.73 (s, 1H), 8.32 (d, J=5.0 Hz, 1H), 8.00 (d, J=5.0 Hz, 1H), 7.64-7.53 (m, 1H), 7.30 (dd, J=3.4, 2.0 Hz, 1H), 6.68 (s, 1H), 4.64 (brs, 1H), 4.20 (d, J=11.5 Hz, 1H), 4.00 (dd, J=11.4, 3.6 Hz, 1H), 3.80 (d, J=11.4 Hz, 1H), 3.67 (dd, J=11.5, 3.0 Hz, 1H), 3.52 (td, J=11.9, 2.9 Hz, 1H), 3.24 (td, J=12.9, 3.9 Hz, 1H), 1.38 (s, 9H), 1.26 (d, J=6.7 Hz, 3H).

Example CY-235: Preparation of (3R)-3-methyl-4-(6-phenyl-2-[1H-pyrrolo[2,3-b]pyridin-4-yl]pyrimidin-4-yl)morpholine Synthesis of methyl (3R)-4-(2-chloro-6-phenylpyrimidin-4-yl)-3-methylmorpholine: Into a 250-mL round-bottom flask, was placed 2,4-dichloro-6-phenylpyrimidine (2 g, 8.886 mmol, 1 equiv), (3R)-3-methylmorpholine (1.08 g, 10.663 mmol, 1.2 equiv), TEA (1.80 g, 17.772 mmol, 2.0 equiv), EtOH (20 mL). The resulting solution was stirred for 4 hr at 70° C. The resulting mixture was concentrated. The residue was applied onto a silica gel column with ethyl acetate/petroleum ether (15:85). This resulted in 0.8 g (31.07%) of (3R)-4-(2-chloro-6-phenylpyrimidin-4-yl)-3-methylmorpholine as colorless oil. LC-MS-BLV-CY-235-1: (ES, m/z): 290[M+H]$^+$. H-NMR-BLV-CY-235-1: (300 MHz, d$_6$-DMSO, ppm): δ 8.19-8.04 (m, 2H), 7.61-7.43 (m, 3H), 7.28 (s, 1H), 4.53 (brs, 1H), 4.17 (d, J=13.3 Hz, 1H), 3.95 (dd, J=11.4, 3.7 Hz, 1H), 3.74 (d, J=11.5 Hz, 1H), 3.62 (dd, J=11.6, 3.0 Hz, 1H), 3.47 (td, J=11.9, 2.9 Hz, 1H), 3.25 (td, J=13.1, 3.7 Hz, 1H), 1.24 (d, J=6.7 Hz, 3H).

Synthesis of methyl (3R)-4-(2-chloro-6-phenylpyrimidin-4-yl)-3-methylmorpholine: Into a 40-mL microwave and maintained with an inert atmosphere of nitrogen, was placed (3R)-4-(2-chloro-6-phenylpyrimidin-4-yl)-3-methylmorpholine (200 mg, 0.690 mmol, 1 equiv), 4-(4,4,5,5-tetramethyl-1,3,2-dioxaborolan-2-yl)-1H-pyrrolo[2,3-b]pyridine (269.57 mg, 1.104 mmol, 1.6 equiv), Pd(dppf)Cl$_2$ (112.23 mg, 0.138 mmol, 0.2 equiv), Na$_2$CO$_3$ (146.31 mg, 1.380 mmol, 2.0 equiv), DME (8 mL), H$_2$O (2 mL). The resulting solution was stirred for 1 hr at 90° C. The crude product was purified by Prep-HPLC. This resulted in 45 mg (17.55%) of (3R)-3-methyl-4-(6-phenyl-2-[1H-pyrrolo[2,3-b]pyridin-4-yl]pyrimidin-4-yl)morpholine as a brown solid. LC-MS-BLV-CY-235-0: (ES, m/z): 372 [M+H]$^+$. H-NMR-BLV-CY-235-0: (300 MHz, d$_6$-DMSO, ppm): δ 11.79 (s, 1H), 8.40-8.31 (m, 3H), 8.14-8.11 (m, 1H), 7.63-7.52 (m, 4H), 7.36-7.32 (m, 2H), 4.76 (brs, 1H), 4.36 (d, J=13.3 Hz, 1H), 4.04 (dd, J=11.6, 3.6 Hz, 1H), 3.83 (d, J=11.4 Hz, 1H), 3.72 (dd, J=11.7, 3.1 Hz, 1H), 3.57 (td, J=12.6, 2.9 Hz, 1H), 3.37 (d, J=3.8 Hz, 1H), 1.31 (d, J=6.6 Hz, 3H).

Example CY-236: Preparation of (3R)-4-[6-(2-fluoropropan-2-yl)-2-[1H-pyrrolo[2,3-b]pyridin-4-yl]pyrimidin-4-yl]-3-methylmorpholine Synthesis of methyl 2-chloro-6-[(3R)-3-methylmorpholin-4-yl]pyrimidine-4-carboxylate: Into a 500-mL round-bottom flask, was placed methyl 2,6-dichloropyrimidine-4-carboxylate (5 g, 24.153 mmol, 1 equiv), DCM (100 mL), TEA (2.7 g, 26.682 mmol, 1.10 equiv), (3R)-3-methylmorpholine (2.49 g, 24.617 mmol, 1.02 equiv). The resulting solution was stirred for 2 hr at room temperature. The resulting mixture was concentrated. The residue was applied onto a silica gel column with ethyl acetate/petroleum ether (1/15-1/3). This resulted in 3.8 g (57.90%) of methyl 2-chloro-6-[(3R)-3-methylmorpholin-4-yl]pyrimidine-4-carboxylate as a yellow solid.

Synthesis of 2-[2-chloro-6-[(3R)-3-methylmorpholin-4-yl]pyrimidin-4-yl]propan-2-ol: Into a 50-mL round-bottom flask purged and maintained with an inert atmosphere of nitrogen, was placed methyl 2-chloro-6-[(3R)-3-methylmorpholin-4-yl]pyrimidine-4-carboxylate (700 mg, 2.576 mmol, 1 equiv), THF (15 mL). This was followed by the addition of CH$_3$MgCl (2.15 mL, 6.441 mmol, 2.50 equiv) dropwise with stirring at −60° C. The resulting solution was stirred for 0.5 hr at −60° C. The reaction was then quenched by the addition of 50 mL of saturated aqueous NH$_4$Cl. The resulting solution was extracted with 4×30 mL of ethyl acetate and the organic layers were combined and concentrated. The residue was applied onto a silica gel column with ethyl acetate/petroleum ether (1/4). This resulted in 500 mg (71.42%) of 2-[2-chloro-6-[(3R)-3-methylmorpholin-4-yl]pyrimidin-4-yl]propan-2-ol as yellow oil.

Synthesis of (3R)-4-[2-chloro-6-(2-fluoropropan-2-yl)pyrimidin-4-yl]-3-methylmorpholine: Into a 50-mL 3-necked round-bottom flask purged and maintained with an inert atmosphere of nitrogen, was placed 2-[2-chloro-6-[(3R)-3-methylmorpholin-4-yl]pyrimidin-4-yl]propan-2-ol (200 mg, 0.736 mmol, 1 equiv), DCM (2 mL). This was followed by the addition of a solution of DAST (178 mg, 1.104 mmol, 1.50 equiv) in DCM (0.5 mL) dropwise with stirring at 0° C. The resulting solution was stirred for 1 hr at room temperature. The reaction was then quenched by the addition of 50 mL of saturated aqueous NaHCO$_3$. The resulting solution was extracted with 3×30 mL of dichloromethane and the organic layers were combined and concentrated. The residue was applied onto a silica gel column with ethyl acetate/petroleum ether (1/4). This resulted in 95 mg (47.15%) of (3R)-4-[2-chloro-6-(2-fluoropropan-2-yl)pyrimidin-4-yl]-3-methylmorpholine as yellow oil. LC-MS-BLV-CY-236-1: (ES, m/z): 274 [M+H]$^+$. H-NMR-BLV-CY-236-1: (300 MHz, CDCl$_3$, ppm): δ 6.61 (s, 1H), 4.38 (brs, 1H), 4.11-4.01 (m, 2H), 3.81 (d, J=11.4 Hz, 1H), 3.71 (dd, J=11.4, 2.7 Hz, 1H), 3.57 (td, J=12.0, 3.0 Hz, 1H), 3.32 (td, J=12.9, 3.6 Hz, 1H), 1.71 (s, 3H), 1.67 (s, 3H), 1.36 (d, J=6.6 Hz, 3H).

Synthesis of (3R)-4-[6-(2-fluoropropan-2-yl)-2-[1H-pyrrolo[2,3-b]pyridin-4-yl]pyrimidin-4-yl]-3-methylmorpholine: Into a 20-mL microwave tube purged and maintained with an inert atmosphere of nitrogen, was placed (3R)-4-[2-chloro-6-(2-fluoropropan-2-yl)pyrimidin-4-yl]-3-methylmorpholine (90 mg, 0.329 mmol, 1 equiv), DME (4 mL), 4-(4,4,5,5-tetramethyl-1,3,2-dioxaborolan-2-yl)-1H-pyrrolo[2,3-b]pyridine (161 mg, 0.660 mmol, 2.01 equiv), Pd(dppf)Cl$_2$ (54 mg, 0.074 mmol, 0.22 equiv), Na$_2$CO$_3$ (71 mg, 0.670 mmol, 2.04 equiv), H$_2$O (1 mL). The final reaction mixture was irradiated with microwave radiation for 0.5 hr at 100° C. The crude product was purified by Flash-Prep-HPLC with the following conditions (IntelFlash-1): Column, C18 silica gel; mobile phase, CH$_3$CN/0.05% HCOOH=70% increasing to CH$_3$CN/0.05% HCOOH=80%; Detector, 254 nm & 220 nm. This resulted in 25 mg (21.39%) of (3R)-4-[6-(2-fluoropropan-2-yl)-2-[1H-pyrrolo[2,3-b]pyridin-4-yl]pyrimidin-4-yl]-3-methylmorpholine as a light yellow solid. LC-MS-BLV-CY-236-0: (ES, m/z): 356 [M+H]$^+$. H-NMR-BLV-CY-236-0: (300 MHz, CDCl$_3$, ppm): δ 9.71 (s, 1H), 8.42 (d, J=5.1 Hz, 1H), 8.11 (d, J=5.1 Hz, 1H), 7.45 (d, J=3.6 Hz, 1H), 7.38 (d, J=3.3 Hz, 1H), 6.72 (s, 1H), 4.58 (brs, 1H), 4.23 (d, J=12.6, 1H), 4.09 (dd, J=11.1, 3.3 Hz, 1H), 3.87 (d, J=11.4 Hz, 1H), 3.78 (dd, J=11.4, 2.7 Hz, 1H), 3.64 (td, J=12.3, 3.0, 1H), 3.39 (td, J=12.6, 3.6 Hz, 1H), 1.82 (s, 3H), 1.75 (s, 3H), 1.40 (d, J=6.9 Hz, 3H).

Example CY-237: Preparation of 2-methyl-2-[6-[(3R)-3-methylmorpholin-4-yl]-2-[1H-pyrrolo[2,3-b]pyridin-4-yl]pyrimidin-4-yl]propanenitrile Synthesis of (3R)-4-(2,6-dichloropyrimidin-4-yl)-3-methylmorpholine: Into a 1-L 3-necked round-bottom flask, was placed 2,4,6-trichloropyrimidine (36.5 g, 198.997 mmol, 1 equiv), DCM (550 mL), DIEA (51.34 g, 397.236 mmol, 2.00 equiv). This was followed by the addition of (3R)-3-methylmorpholine (22.11 g, 218.588 mmol, 1.10 equiv) dropwise with stirring at 5° C. The resulting solution was stirred for 2 hr at room temperature. The resulting mixture was concentrated. The residue was applied onto a silica gel column with ethyl acetate/petroleum ether (1/25-1/1). This resulted in 30 g (60.76%) of (3R)-4-(2,6-dichloropyrimidin-4-yl)-3-methylmorpholine as a off-white solid. LC-MS-BLV-CY-233-1: (ES, m/z): 248 [M+H]$^+$. H-NMR-BLV-CY-233-1: (300 MHz, CDCl$_3$, ppm): δ 6.37 (s, 1H), 4.25 (brs, 1H), 4.03-3.98 (m, 2H), 3.79 (d, J=11.7 Hz, 1H), 3.68 (dd, J=11.7, 3.0 Hz, 1H), 3.54 (td, J=12.0, 3.0 Hz, 1H), 3.30 (td, J=13.2, 3.9 Hz, 1H), 1.33 (d, J=6.6 Hz, 3H).

Synthesis of 2-[2-chloro-6-[(3R)-3-methylmorpholin-4-yl]pyrimidin-4-yl]-2-methylpropanenitrile: Into a 500-mL 3-necked round-bottom flask purged and maintained with an inert atmosphere of argon, was placed (3R)-4-(2,6-dichloropyrimidin-4-yl)-3-methylmorpholine (30 g, 120.914 mmol, 1 equiv), toluene (200 mL). This was followed by the addition of NaHMDS (84.6 mL, 2M, 169.280 mmol, 1.4 equiv) dropwise with stirring at 5° C. The resulting solution was stirred for 0.5 hr at 5° C. To this was added a solution of 2-methylpropanenitrile (8.34 g, 120.682 mmol, 1.00 equiv) in tolene (10 mL) dropwise with stirring at 5° C. The resulting solution was stirred for 2 hr at room temperature. The resulting solution was diluted with 650 mL of H$_2$O. The organic phase was separated. The aqueous layer was extracted with 4×500 mL of ethyl acetate. The combined organic layer was concentrated under vacuum. The crude product was purified by Flash-Prep-HPLC with the following conditions (IntelFlash-1): Column, C18 silica gel; mobile phase, CH$_3$CN/0.1% NH$_4$HCO$_3$=48% increasing to CH$_3$CN/0.1% NH$_4$HCO$_3$=48% within 42 min; Detector, 254 nm & 220 nm. This resulted in 16 g (47.13%) of 2-[2-chloro-6-[(3R)-3-methylmorpholin-4-yl]pyrimidin-4-yl]-2-methylpropanenitrile as light yellow oil. LC-MS-BLV-CY-237-1: (ES, m/z): 281 [M+H]$^+$. H-NMR-BLV-CY-237-1: (300 MHz, CDCl$_3$, ppm): δ 6.67 (s, 1H), 4.37 (brs, 1H), 4.04-3.99 (m, 2H), 3.80 (d, J=11.7 Hz, 1H), 3.69 (dd, J=11.4, 3.0 Hz, 1H), 3.54 (td, J=12.0, 3.0 Hz, 1H), 3.31 (td, J=13.2, 3.9 Hz, 1H), 1.70 (s, 6H), 1.34 (d, J=6.9 Hz, 3H).

Synthesis of 2-methyl-2-[6-[(3R)-3-methylmorpholin-4-yl]-2-[1H-pyrrolo[2,3-b]pyridin-4-yl]pyrimidin-4-yl]propanenitrile: Into a 1-L round-bottom flask purged and maintained with an inert atmosphere of nitrogen, was placed 2-[2-chloro-6-[(3R)-3-methylmorpholin-4-yl]pyrimidin-4-yl]-2-methylpropanenitrile (16 g, 56.988 mmol, 1 equiv), DME (320 mL), 4-(4,4,5,5-tetramethyl-1,3,2-dioxaborolan-2-yl)-1H-pyrrolo[2,3-b]pyridine (18.13 g, 74.273 mmol, 1.30 equiv), Pd(dppf)Cl$_2$ (4.65 g, 6.355 mmol, 0.11 equiv), K$_2$CO$_3$ (15.78 g, 114.178 mmol, 2.00 equiv), H$_2$O (32 mL). The resulting solution was stirred for 15 hr at 100° C. in an oil bath. The solids were filtered out. The resulting solution was diluted with 500 mL of H$_2$O. The resulting solution was extracted with 4×700 mL of ethyl acetate and the organic layers combined and concentrated. The residue was applied onto a silica gel column with ethyl acetate/petroleum ether (1/3-1/1). The product was purified by Flash-Prep-HPLC with the following conditions (IntelFlash-1): Column, C18 silica gel; mobile phase, CH$_3$CN/0.1% NH$_3$.H$_2$O=100%; Detector, 254 nm & 220 nm. This resulted in 12 g (58.10%) of 2-methyl-2-[6-[(3R)-3-methylmorpholin-4-yl]-2-[1H-pyrrolo[2,3-b]pyridin-4-yl]pyrimidin-4-yl]propanenitrile as a off-white solid. LC-MS-BLV-CY-237-0: (ES, m/z): 363 [M+H]$^+$. H-NMR-BLV-CY-237-0: (300 MHz, CD$_3$OD, ppm): δ 8.31 (d, J=5.4 Hz, 1H), 8.13 (d, J=5.1 Hz, 1H), 7.51 (d, J=3.3 Hz, 1H), 7.47 (d, J=3.6 Hz, 1H), 6.84 (s, 1H), 4.71 (brs, 1H), 4.26 (d, J=12.6, 1H), 4.09 (dd, J=11.1, 3.9 Hz, 1H), 3.89 (d, J=11.4 Hz, 1H), 3.80 (dd, J=11.4, 3.0 Hz, 1H), 3.66 (td, J=12.3, 3.0, 1H), 3.42 (td, J=12.9, 3.9 Hz, 1H), 1.85 (s, 6H), 1.40 (d, J=6.6 Hz, 3H).

Example CY-238: Preparation of (3R)-4-(6-cyclopropyl-2-[1H-pyrrolo[2,3-b]pyridin-4-yl]pyrimidin-4-yl)-3-methylmorpholine Synthesis of methyl 2,4-dichloro-6-cyclopropylpyrimidine: Into a 25-mL round-bottom flask, was placed 2,4,6-trichloropyrimidine (500 mg, 2.726 mmol, 1 equiv). This was followed by the addition of bromo(cyclopropyl)zinc (5 mL) stirred at 0° C. To this was added Pd(PPh$_3$)$_4$ (78 mg, 0.067 mmol, 0.02 equiv) at 0° C. The resulting solution was stirred for 3 hr at 70° C. The reaction was then quenched by the addition of aq. NH$_4$Cl. The resulting solution was extracted with 2×50 mL of ethyl acetate and the organic layer was combined. The resulting EA mixture was washed with 2×30 mL of brine. The EA mixture was dried over anhydrous sodium sulfate and concentrated. The crude product was purified by Flash-Prep-HPLC 0.1% NH$_3$.H$_2$O: MeCN=40% increasing to 0.1% NH$_3$.H$_2$O:MeCN=70% within 10 min. This resulted in 300 mg (58.22%) of 2,4-dichloro-6-cyclopropylpyrimidine as a colorless solid. LC-MS-BLV-CY-238-1: (ES, m/z): 189 [M+H]$^+$. H-NMR-BLV-CY-238-1: (300 MHz, CDCl$_3$, ppm): δ 7.16 (s, 1H), 2.03-1.94 (m, 1H), 1.29-1.17 (m, 4H).

Synthesis of methyl (3R)-4-(2-chloro-6-cyclopropylpyrimidin-4-yl)-3-methylmorpholine: Into a 50-mL round-bottom flask, was placed 2,4-dichloro-6-cyclopropylpyrimidine (350 mg, 1.851 mmol, 1 equiv), (3R)-3-methylmorpholine (206.00 mg, 2.037 mmol, 1.1 equiv), TEA (374.70 mg, 3.703 mmol, 2.0 equiv), EtOH (5 mL). The resulting solution was stirred overnight at 70° C. The crude product was purified by Flash-Prep-HPLC 0.1% $NH_3.H_2O$:MeCN=50% increasing to 0.1% $NH_3.H_2O$:MeCN=70% within 15 min. This resulted in 230 mg (48.96%) of (3R)-4-(2-chloro-6-cyclopropylpyrimidin-4-yl)-3-methylmorpholine as a colorless oil. LC-MS-BLV-CY-238-2: (ES, m/z): 254 [M+H]$^+$. H-NMR-BLV-CY-238-2: (300 MHz, CDCl$_3$, ppm): 66.22 (s, 1H), 4.30 (brs, 1H), 4.04-3.97 (m, 2H), 3.79 (d, J=11.5 Hz, 1H), 3.70 (dd, J=11.6, 2.9 Hz, 1H), 3.55 (td, J=11.8, 3.1 Hz, 1H), 3.26 (td, J=12.7, 12.2, 3.9 Hz, 1H), 1.88-1.79 (m, 1H), 1.32 (d, J=6.7 Hz, 3H), 1.17-1.08 (m, 2H), 1.02-0.95 (m, 2H).

Synthesis of (3R)-4-(6-cyclopropyl-2-[1H-pyrrolo[2,3-b]pyridin-4-yl]pyrimidin-4-yl)-3-methylmorpholine: Into a 8-mL microwave and maintained with an inert atmosphere of nitrogen, was placed (3R)-4-(2-chloro-6-cyclopropylpyrimidin-4-yl)-3-methylmorpholine (140 mg, 0.552 mmol, 1 equiv), 4-(4,4,5,5-tetramethyl-1,3,2-dioxaborolan-2-yl)-1H-pyrrolo[2,3-b]pyridine (215.50 mg, 0.883 mmol, 1.6 equiv), Pd(dppf)Cl$_2$ (40.37 mg, 0.055 mmol, 0.10 equiv), Na$_2$CO$_3$ (116.96 mg, 1.104 mmol, 2.00 equiv), DME (3 mL), H$_2$O (0.8 mL). The resulting solution was stirred for 40 min at 90° C. The crude product was purified by Prep-HPLC. This resulted in 40 mg (21.6%) of (3R)-4-(6-cyclopropyl-2-[1H-pyrrolo[2,3-b]pyridin-4-yl]pyrimidin-4-yl)-3-methylmorpholine as a white solid. LC-MS-BLV-CY-238-0: (ES, m/z): 336 [M+H]$^+$. H-NMR-BLV-CY-238-0: (300 MHz, d$_6$-DMSO, ppm): 11.75 (s, 1H), 8.32 (d, J=5.0 Hz, 1H), 7.94 (d, J=5.0 Hz, 1H), 7.57 (t, J=2.9 Hz, 1H), 7.17-7.15 (m, 1H), 6.77 (s, 1H), 4.56 (d, J=7.4 Hz, 1H), 4.17 (d, J=12.6 Hz, 1H), 4.00 (dd, J=11.3, 3.6 Hz, 1H), 3.79 (d, J=11.4 Hz, 1H), 3.66 (dd, J=11.5, 3.1 Hz, 1H), 3.51 (td, J=11.8, 2.9 Hz, 1H), 3.24 (td, J=12.7, 3.8 Hz, 1H), 2.11-2.03 (m, 1H), 1.26 (d, J=6.7 Hz, 3H), 1.17-1.13 (m, 2H), 1.05-1.00 (m, 2H).

Example CY-239: Preparation of (3R)-4-(6-cyclobutyl-2-[1H-pyrrolo[2,3-b]pyridin-4-yl]pyrimidin-4-yl)-3-methylmorpholine Synthesis of 2,4-dichloro-6-cyclobutylpyrimidine: Into a 100-mL round-bottom flask, was placed 2,4,6-trichloropyrimidine (2 g, 10.904 mmol, 1 equiv) and THF (30 mL). This was followed by the addition of bromo(cyclobutyl)zinc (20 mL) stirred at 0° C. To this was added Pd(PPh$_3$)$_4$ (315.00 mg, 0.273 mmol, 0.02 equiv) at 0° C. The resulting solution was stirred for 3 hr at 70° C. The reaction mixture was cooled to room temperature. The crude product was purified by Flash-Prep-HPLC 0.1% NH$_3$.H$_2$O:MeCN=45% increasing to 0.1% NH$_3$.H$_2$O:MeCN=75% within 9 min. This resulted in 0.7 g (31.61%) of 2,4-dichloro-6-cyclobutylpyrimidine as a yellow solid. LC-MS-BLV-CY-239-1: (ES, m/z): 203 [M+H]$^+$. H-NMR-BLV-CY-239-1: (300 MHz, CDCl$_3$, ppm): 67.15 (s, 1H), 3.68-3.56 (m, 1H), 2.44-2.29 (m, 4H), 2.19-2.07 (m, 1H), 2.04-1.91 (m, 1H).

Synthesis of (3R)-4-(2-chloro-6-cyclobutylpyrimidin-4-yl)-3-methylmorpholine: Into a 50-mL round-bottom flask, was placed 2,4-dichloro-6-cyclobutylpyrimidine (1.4 g, 6.894 mmol, 1 equiv), (3R)-3-methylmorpholine (0.77 g, 7.584 mmol, 1.1 equiv), TEA (1.40 g, 13.788 mmol, 2.0 equiv), EtOH (14 mL). The resulting solution was stirred for 2 hr at 70° C. The crude product was purified by Flash-Prep-HPLC 0.1% NH$_3$.H$_2$O:MeCN=50% increasing to 0.1% NH$_3$.H$_2$O:MeCN=70% within 9 min. This resulted in 1.1 g (59.59%) of (3R)-4-(2-chloro-6-cyclobutylpyrimidin-4-yl)-3-methylmorpholine as a yellow solid. LC-MS-BLV-CY-239-2: (ES, m/z): 268 [M+H]$^+$. H-NMR-BLV-CY-239-2: (300 MHz, CDCl$_3$, ppm): δ 6.18 (s, 1H), 4.32 (brs, 1H), 4.08-3.94 (m, 2H), 3.78 (d, J=11.5 Hz, 1H), 3.69 (dd, J=11.6, 2.9 Hz, 1H), 3.60-3.38 (m, 2H), 3.27 (td, J=13.4, 4.1 Hz, 1H), 2.36-2.22 (m, 4H), 2.12-1.97 (m, 1H), 1.96-1.82 (m, 1H), 1.31 (dd, J=6.8, 0.7 Hz, 3H).

Synthesis of (3R)-4-(6-cyclobutyl-2-[1H-pyrrolo[2,3-b]pyridin-4-yl]pyrimidin-4-yl)-3-methylmorpholine: Into a 8-mL microwave and maintained with an inert atmosphere of nitrogen, was placed Pd(dppf)Cl$_2$ (32.79 mg, 0.045 mmol, 0.1 equiv), Na$_2$CO$_3$ (95.00 mg, 0.896 mmol, 2.00 equiv), DME (3 mL), H$_2$O (1 mL), (3R)-4-(2-chloro-6-cyclobutylpyrimidin-4-yl)-3-methylmorpholine (120 mg, 0.448 mmol, 1 equiv), 4-(4,4,5,5-tetramethyl-1,3,2-dioxaborolan-2-yl)-1H-pyrrolo[2,3-b]pyridine (175.03 mg, 0.717 mmol, 1.6 equiv). The resulting solution was stirred for 40 min at 90° C. The crude product was purified by Prep-HPLC. This resulted in 40 mg (25.6%) of (3R)-4-(6-cyclobutyl-2-[1H-pyrrolo[2,3-b]pyridin-4-yl]pyrimidin-4-yl)-3-methylmorpholine as a white solid. LC-MS-BLV-CY-239-0: (ES, m/z): 349 [M+H]$^+$. H-NMR-BLV-CY-239-0: (300 MHz, d$_6$-DMSO, ppm): δ 11.74 (s, 1H), 8.33 (d, J=5.0 Hz, 1H), 8.01 (d, J=5.0 Hz, 1H), 7.58 (t, J=2.9 Hz, 1H), 7.31 (dd, J=3.3, 1.9 Hz, 1H), 6.62 (s, 1H), 4.60 (brs, 1H), 4.18 (d, J=13.3 Hz, 1H), 3.99 (dd, J=11.3, 3.6 Hz, 1H), 3.79 (d, J=11.5 Hz, 1H), 3.71-3.44 (m, 3H), 3.24 (td, J=12.7, 3.9 Hz, 1H), 2.46-2.27 (m, 4H), 2.12-1.90 (m, 2H), 1.25 (d, J=6.7 Hz, 3H).

Example CY-240: Preparation of (3R)-4-(6-cyclopentyl-2-[1H-pyrrolo[2,3-b]pyridin-4-yl]pyrimidin-4-yl)-3-methylmorpholine Synthesis of 2,4-dichloro-6-cyclopentylpyrimidine: Into a 100-mL round-bottom flask, was placed 2,4,6-trichloropyrimidine (3 g, 16.356 mmol, 1 equiv), Fe(acac)$_3$ (1.16 g, 3.271 mmol, 0.20 equiv), THF (30 mL). This was followed by the addition of NMP (5 mL) stirred at 0° C. To this solution was added bromo(cyclopentyl)magnesium (1M THF, 16.5 mL, 1 equiv), in portions at 0° C. The resulting solution was stirred for 1 hr at room temperature. The reaction was then quenched by the addition of 50 mL of aq. NH$_4$Cl. The resulting solution was extracted with ethyl acetate (2×100 mL). The combined organic layer was washed with 2×50 mL of brine. The mixture was dried over anhydrous sodium sulfate and concentrated. The residue was applied onto a silica gel column with ethyl acetate/petroleum ether (10:90). This resulted in 500 mg (14.08%) of 2,4-dichloro-6-cyclopentylpyrimidine as colorless oil. LC-MS-BLV-CY-240-1: (ES, m/z): 217 [M+H]$^+$. H-NMR-BLV-CY-240-1: (300 MHz, CDCl$_3$, ppm): δ 7.16 (s, 1H), 3.17-3.06 (m, 1H), 2.10-2.04 (m, 2H), 1.94-1.69 (m, 6H).

Synthesis of (3R)-4-(2-chloro-6-cyclopentylpyrimidin-4-yl)-3-methylmorpholine: Into a 50-mL round-bottom flask, was placed 2,4-dichloro-6-cyclopentylpyrimidine (400 mg, 1.843 mmol, 1 equiv), (3R)-3-methylmorpholine (205.01 mg, 2.027 mmol, 1.1 equiv), TEA (372.90 mg, 3.685 mmol, 2.0 equiv), EtOH (10.00 mL). The resulting solution was stirred overnight at 70° C. The residue was applied onto a silica gel column with ethyl acetate/petroleum ether (1:10). This resulted in 240 mg (46.23%) of (3R)-4-(2-chloro-6-cyclopentylpyrimidin-4-yl)-3-methylmorpholine as colorless oil. LC-MS-BLV-CY-240-1: (ES, m/z): 282 [M+H]$^+$.

Synthesis of (3R)-4-(6-cyclopentyl-2-[1H-pyrrolo[2,3-b]pyridin-4-yl]pyrimidin-4-yl)-3-methylmorpholine: Into a 8-mL microwave and maintained with an inert atmosphere of nitrogen, was placed (3R)-4-(2-chloro-6-cyclopentylpyrimidin-4-yl)-3-methylmorpholine (100 mg, 0.355 mmol, 1 equiv), 4-(4,4,5,5-tetramethyl-1,3,2-dioxaborolan-2-yl)-1H-pyrrolo[2,3-b]pyridine (129.94 mg, 0.532 mmol, 1.5 equiv), Pd(dppf)Cl$_2$ (25.97 mg, 0.035 mmol, 0.1 equiv), Na$_2$CO$_3$ (75.23 mg, 0.710 mmol, 2.0 equiv), DME (3 mL), H$_2$O (1 mL). The resulting solution was stirred for 40 min at 90° C. The crude product was purified by Prep-HPLC. This resulted in 40 mg (31.01%) of (3R)-4-(6-cyclopentyl-2-[1H-pyrrolo[2,3-b]pyridin-4-yl]pyrimidin-4-yl)-3-methylmorpholine as a white solid. LC-MS-BLV-CY-240-0: (ES, m/z): 364 [M+H]$^+$. H-NMR-BLV-CY-240-0: (300 MHz, CD$_3$OD, ppm): δ 8.28 (d, J=5.2 Hz, 1H), 8.03 (d, J=5.2 Hz, 1H), 7.48 (d, J=3.5 Hz, 1H), 7.35 (d, J=3.5 Hz, 1H), 6.58 (s, 1H), 4.64 (brs, 1H), 4.20 (d, J=13.8 Hz, 1H), 4.05 (dd, J=12.2, 3.9 Hz, 1H), 3.86 (d, J=11.5 Hz, 1H), 3.78 (dd, J=11.7, 3.3 Hz, 1H), 3.63 (td, J=12.0, 3.0 Hz, 1H), 3.40-3.35 (m, 1H), 3.22-3.10 (m, 1H), 2.11-1.78 (m, 8H), 1.36 (d, J=6.6 Hz, 3H).

Example CY-241: Preparation of (3R)-4-(6-cyclohexyl-2-[1H-pyrrolo[2,3-b]pyridin-4-yl]pyrimidin-4-yl)-3-methylmorpholine Synthesis of 2,4-dichloro-6-cyclohexylpyrimidine: Into a 25-mL round-bottom flask, was placed 2,4,6-trichloropyrimidine 1 equiv), bromo(cyclohexyl)zinc (1M of THF, 11 mL), Pd(dppf)Cl$_2$ (110.95 mg, 0.136 mmol, 0.03 equiv). The resulting solution was stirred for 1 hr at 70° C. The reaction was then quenched by the addition of 50 mL of aq. NH$_4$Cl. The resulting solution was extracted with 2×100 mL ethyl acetate and the organic layer was combined. The resulting EA mixture was washed with 2×50 mL of brine. The EA mixture was dried over anhydrous sodium sulfate and concentrated. The residue was applied onto a silica gel column with ethyl acetate/petroleum ether (1:10). This resulted in 300 mg of 2,4-dichloro-6-cyclohexylpyrimidine as colorless oil. LC-MS-BLV-CY-241-1: (ES, m/z): 231 [M+H]$^+$. H-NMR-BLV-CY-241-1: (300 MHz, CDCl$_3$, ppm): δ 7.16 (s, 1H), 2.68 (m, 1H), 2.03-1.83 (m, 4H), 1.83-1.73 (m, 1H), 1.58-1.24 (m, 5H).

Synthesis of (3R)-4-(2-chloro-6-cyclohexylpyrimidin-4-yl)-3-methylmorpholine: Into a 50-mL round-bottom flask, was placed 2,4-dichloro-6-cyclohexylpyrimidine (500 mg, 2.163 mmol, 1 equiv), (3R)-3-methylmorpholine (262.59 mg, 2.596 mmol, 1.2 equiv), TEA (437.82 mg, 4.327 mmol, 2.00 equiv), EtOH (10 mL). The resulting solution was stirred for 4 hr at 70° C. The resulting mixture was concentrated. The residue was applied onto a silica gel column with ethyl acetate/petroleum ether (1:8). This resulted in 320 mg (50.00%) of (3R)-4-(2-chloro-6-cyclohexylpyrimidin-4-yl)-3-methylmorpholine as colorless oil. LC-MS-BLV-CY-241-2: (ES, m/z): 296 [M+H]$^+$.

Synthesis of (3R)-4-(6-cyclohexyl-2-[1H-pyrrolo[2,3-b]pyridin-4-yl]pyrimidin-4-yl)-3-methylmorpholine: Into a 8-mL microwave and maintained with an inert atmosphere of nitrogen, was placed (3R)-4-(2-chloro-6-cyclohexylpyrimidin-4-yl)-3-methylmorpholine (100 mg, 0.338 mmol, 1 equiv), 4-(4,4,5,5-tetramethyl-1,3,2-dioxaborolan-2-yl)-1H-pyrrolo[2,3-b]pyridine (123.78 mg, 0.507 mmol, 1.5 equiv), Pd(dppf)Cl$_2$ (27.52 mg, 0.034 mmol, 0.1 equiv), Na$_2$CO$_3$ (71.66 mg, 0.676 mmol, 2.0 equiv), DME (4 mL), H$_2$O (1 mL). The resulting solution was stirred for 30 min at 90° C. The crude product was purified by Prep-HPLC. This resulted in 39 mg (30.7%) of (3R)-4-(6-cyclohexyl-2-[1H-pyrrolo[2,3-b]pyridin-4-yl]pyrimidin-4-yl)-3-methylmorpholine as a white solid. LC-MS-BLV-CY-241-0: (ES, m/z): 378 [M+H]$^+$. H-NMR-BLV-CY-241-0: (300 MHz, d$_6$-DMSO, ppm): δ 11.72 (s, 1H), 8.32 (d, J=5.0 Hz, 1H), 7.98 (d, J=5.0 Hz, 1H), 7.57 (d, J=3.4 Hz, 1H), 7.28 (d, J=3.4 Hz, 1H), 6.64 (s, 1H), 4.57 (brs, 1H), 4.18 (d, J=13.3 Hz, 1H), 3.99 (dd, J=11.8, 3.2 Hz, 1H), 3.79 (d, J=11.3 Hz, 1H), 3.66 (dd, J=11.5, 3.1 Hz, 1H), 3.51 (td, J=11.7, 2.8 Hz, 1H), 3.23 (td, J=12.8, 3.9 Hz, 1H), 2.68-2.59 (m, 1H), 1.98-1.79 (m, 4H), 1.79-1.56 (m, 3H), 1.50-1.31 (m, 3H), 1.25 (d, J=6.6 Hz, 3H).

Example CY-242: Preparation of 2-[6-[(3R)-3-methylmorpholin-4-yl]-2-[1H-pyrrolo[2,3-b]pyridin-4-yl]pyrimidin-4-yl]propan-2-amine Synthesis of 2-[2-chloro-6-[(3R)-3-methylmorpholin-4-yl]pyrimidin-4-yl]-2-methylpropanamide: Into a 50-mL 3-necked round-bottom flask, was placed 2-[2-chloro-6-[(3R)-3-methylmorpholin-4-yl]pyrimidin-4-yl]-2-methylpropanenitrile (1.45 g, 5.165 mmol, 1 equiv), MeOH (10 mL), DCM (10 mL). This was followed by the addition of KOH (87 mg, 1.551 mmol, 0.30 equiv) at 0° C. To this was added H$_2$O$_2$ (30%) (8.78 g, 77.47 mmol, 15.0 equiv) at 0° C. The resulting solution was stirred for 2 hr at room temperature. The resulting mixture was concentrated. The crude product was purified by Flash-Prep-HPLC with the following conditions (IntelFlash-1): Column, C18 silica gel; mobile phase, CH$_3$CN/0.05% NH$_3$.H$_2$O=45% increasing to CH$_3$CN/0.05% NH$_3$.H$_2$O=60%; Detector, 254 nm & 220 nm. This resulted in 600 mg (38.88%) of 2-[2-chloro-6-[(3R)-3-methylmorpholin-4-yl]pyrimidin-4-yl]-2-methylpropanamide as a light yellow solid. LC-MS-BLV-CY-242-2: (ES, m/z): 299 [M+H]$^+$. H-NMR-BLV-CY-242-2: (300 MHz, CDCl$_3$, ppm): δ 6.87 (brs, 1H), 6.42 (s, 1H), 5.37 (brs, 1H), 4.36 (brs, 1H), 4.05 (d, J=3.9 Hz, 1H), 4.01 (d, J=3.6 Hz, 1H), 3.81 (d, J=11.4 Hz, 1H), 3.70 (dd, J=11.7, 3.3 Hz, 1H), 3.56 (td, J=11.7, 3.0 Hz, 1H), 3.31 (td, J=13.2, 3.9 Hz, 1H), 1.60 (s, 6H), 1.34 (d, J=6.9 Hz, 3H).

Synthesis of 2-[2-chloro-6-[(3R)-3-methylmorpholin-4-yl]pyrimidin-4-yl]propan-2-amine: Into a 50-mL 3-necked round-bottom flask, was placed 2-[2-chloro-6-[(3R)-3-methylmorpholin-4-yl]pyrimidin-4-yl]-2-methylpropanamide (800 mg, 2.678 mmol, 1 equiv), H$_2$O (10 mL). This was followed by the addition of NaOH (428 mg, 10.701 mmol, 4.00 equiv) at 0° C. To this was added NaClO (8%) (14.95 g, 16.066 mmol, 6.00 equiv) at 0° C. The resulting solution was stirred for 15 hr at room temperature. The crude product was purified by Flash-Prep-HPLC with the following conditions (IntelFlash-1): Column, C18 silica gel; mobile phase, CH$_3$CN/0.05% NH$_3$.H$_2$O=35% increasing to CH$_3$CN/0.05% NH$_3$.H$_2$O=45%; Detector, 254 nm & 220 nm. This resulted in 85 mg (11.72%) of 2-[2-chloro-6-[(3R)-3-methylmorpholin-4-yl]pyrimidin-4-yl]propan-2-amine as a yellow solid. LC-MS-BLV-CY-242-3: (ES, m/z): 271 [M+H]$^+$. H-NMR-BLV-CY-242-3: (300 MHz, CDCl$_3$, ppm): δ 6.54 (s, 1H), 4.36 (brs, 1H), 4.02 (d, J=3.3 Hz, 1H), 3.98 (d, J=3.9 Hz, 1H), 3.78 (d, J=11.4 Hz, 1H), 3.68 (dd, J=11.4, 3.0 Hz, 1H), 3.54 (td, J=12.3, 3.0 Hz, 1H), 3.28 (td, J=13.2, 3.9 Hz, 1H), 1.46 (s, 6H), 1.31 (d, J=6.9 Hz, 3H).

Synthesis of tert-butyl N-(2-[2-chloro-6-[(3R)-3-methylmorpholin-4-yl]pyrimidin-4-yl]propan-2-yl)carbamate: Into a 50-mL 3-necked round-bottom flask, was placed 2-[2-chloro-6-[(3R)-3-methylmorpholin-4-yl]pyrimidin-4-yl]propan-2-amine (85 mg, 0.314 mmol, 1 equiv), DCM (3 mL), TEA (48 mg, 0.474 mmol, 1.51 equiv). This was followed by the addition of a solution of di-tert-butyl dicarbonate (82 mg, 0.376 mmol, 1.20 equiv) in DCM (0.5 mL) at 0° C. The resulting solution was stirred for 15 hr at room temperature. The reaction was then quenched by the addition of 50 mL of saturated aqueous NaHCO$_3$. The resulting solution was extracted with 2×30 mL of dichloromethane and the organic layers combined and concentrated. The residue was applied onto a silica gel column with ethyl acetate/petroleum ether (1/3). This resulted in 65 mg (55.83%) of tert-butyl N-(2-[2-chloro-6-[(3R)-3-methylmorpholin-4-yl]pyrimidin-4-yl]propan-2-yl)carbamate as a yellow solid. LC-MS-BLV-CY-242-5: (ES, m/z): 371 [M+H]$^+$. H-NMR-BLV-CY-242-5: (300 MHz, CDCl$_3$, ppm): δ 6.40 (s, 1H), 5.31 (brs, 1H), 4.30 (s, 1H), 4.01-3.96 (m, 2H), 3.77 (d, J=11.7 Hz, 1H), 3.68 (dd, J=11.4, 2.7 Hz, 1H), 3.54 (td, J=12.0, 3.0 Hz, 1H), 3.27 (td, J=12.9, 3.9 Hz, 1H), 1.60 (d, J=7.8 Hz, 6H), 1.41 (s, 9H), 1.31 (d, J=6.6 Hz, 3H).

Synthesis of tert-butyl N-(2-[6-[(3R)-3-methylmorpholin-4-yl]-2-[1H-pyrrolo[2,3-b]pyridin-4-yl]pyrimidin-4-yl]propan-2-yl)carbamate: Into a 20-mL microwave tube purged and maintained with an inert atmosphere of nitrogen, was placed tert-butyl N-(2-[2-chloro-6-[(3R)-3-methylmorpholin-4-yl]pyrimidin-4-yl]propan-2-yl)carbamate (65 mg, 0.175 mmol, 1 equiv), dioxane (3 mL), 4-(4,4,5,5-tetramethyl-1,3,2-dioxaborolan-2-yl)-1H-pyrrolo[2,3-b]pyridine (86 mg, 0.352 mmol, 2.01 equiv), Pd(dppf)Cl$_2$ (13 mg, 0.018 mmol, 0.10 equiv), K$_2$CO$_3$ (48 mg, 0.347 mmol, 1.98 equiv), H$_2$O (0.3 mL). The final reaction mixture was irradiated with microwave radiation for 1 hr at 100° C. The crude product was purified by Flash-Prep-HPLC with the following conditions (IntelFlash-1): Column, C18 silica gel; mobile phase, CH$_3$CN/0.05% HCOOH=40% increasing to CH$_3$CN/0.05% HCOOH=50%; Detector, 254 nm & 220 nm. This resulted in 50 mg (63.04%) of tert-butyl N-(2-[6-[(3R)-3-methylmorpholin-4-yl]-2-[1H-pyrrolo[2,3-b]pyridin-4-yl]pyrimidin-4-yl]propan-2-yl)carbamate as a yellow solid. LC-MS-BLV-CY-242-4: (ES, m/z): 371 [M+H]$^+$.

Synthesis of 2-[6-[(3R)-3-methylmorpholin-4-yl]-2-[1H-pyrrolo[2,3-b]pyridin-4-yl]pyrimidin-4-yl]propan-2-amine: Into a 50-mL round-bottom flask, was placed tert-butyl N-(2-[6-[(3R)-3-methylmorpholin-4-yl]-2-[1H-pyrrolo[2,3-b]pyridin-4-yl]pyrimidin-4-yl]propan-2-yl)carbamate (50 mg, 0.110 mmol, 1 equiv), MeOH (1 mL). To the above HCl (g) in MeOH (1 mL) was introduced in at room temperature. The resulting solution was stirred for 15 hr at room temperature. The resulting mixture was concentrated. This resulted in 7.1 mg (18.23%) of 2-[6-[(3R)-3-methylmorpholin-4-yl]-2-[1H-pyrrolo[2,3-b]pyridin-4-yl]pyrimidin-4-yl]propan-2-amine as a yellow solid. LC-MS-BLV-CY-242-0: (ES, m/z): 353 [M+H]$^+$. H-NMR-BLV-CY-242-0: (300 MHz, CD$_3$OD, ppm): δ 8.70 (d, J=5.7 Hz, 1H), 8.58 (d, J=5.7 Hz, 1H), 7.88 (d, J=3.0 Hz, 1H), 7.68 (d, J=3.3 Hz, 1H), 7.02 (s, 1H), 4.74 (brs, 1H), 4.29 (d, J=11.7 Hz, 1H), 4.11 (d, J=9.3 Hz, 1H), 3.91 (d, J=11.4 Hz, 1H), 3.81 (d, J=11.4 Hz, 1H), 3.67 (t, J=10.5 Hz, 1H), 3.48 (t, J=12.3 Hz, 1H), 1.83 (s, 6H), 1.43 (d, J=6.9 Hz, 3H).

Example CY-243: Preparation of 2-methyl-2-[6-[(3R)-3-methylmorpholin-4-yl]-2-[1H-pyrrolo[2,3-b]pyridin-4-yl]pyrimidin-4-yl]propanamide Synthesis of 2-methyl-2-[6-[(3R)-3-methylmorpholin-4-yl]-2-[1H-pyrrolo[2,3-b]pyridin-4-yl]pyrimidin-4-yl]propanamide: Into a 50-mL 3-necked round-bottom flask, was placed 2-methyl-2-[6-[(3R)-3-methylmorpholin-4-yl]-2-[1H-pyrrolo[2,3-b]pyridin-4-yl]pyrimidin-4-yl]propanenitrile (40 mg, 0.110 mmol, 1 equiv), MeOH (1 mL), DCM (1 mL), KOH (25%) (0.15 mL). This was followed by the addition of H$_2$O$_2$ (30%) (50 mg, 0.441 mmol, 4.0 equiv) dropwise with stirring at 0° C. The resulting solution was stirred for 2 hr at 50° C. in an oil bath. The resulting mixture was concentrated. The crude product was purified by Flash-Prep-HPLC with the following conditions (IntelFlash-1): Column, C18 silica gel; mobile phase, CH$_3$CN/0.05% HCOOH=35% increasing to CH$_3$CN/0.05% HCOOH=50%; Detector, 254 nm& 220 nm. This resulted in 20 mg (47.63%) of 2-methyl-2-[6-[(3R)-3-methylmorpholin-4-yl]-2-[1H-pyrrolo[2,3-b]pyridin-4-yl]pyrimidin-4-yl]propanamide as a light yellow solid. LC-MS-BLV-CY-243-0: (ES, m/z): 381 [M+H]$^+$. H-NMR-BLV-CY-243-0: (300 MHz, CD$_3$OD, ppm): δ 8.26 (d, J=5.1 Hz, 1H), 8.09 (d, J=5.1 Hz, 1H), 7.47 (d, J=3.3 Hz, 1H), 7.41 (d, J=3.3 Hz, 1H), 6.68 (s, 1H), 4.66 (brs, 1H), 4.21 (d, J=12.0 Hz, 1H), 4.05 (dd, J=11.4, 3.6 Hz, 1H), 3.86 (d, J=11.4 Hz, 1H), 3.77 (dd, J=11.7, 3.0 Hz, 1H), 3.63 (td, J=12.3, 3.3 Hz, 1H), 3.39 (dd, J=13.2, 4.2 Hz, 1H), 1.66 (s, 6H), 1.39 (d, J=6.9 Hz, 3H).

Example CY-244: Preparation of 2-methyl-2-[6-[(3R)-3-methylmorpholin-4-yl]-2-[1H-pyrrolo[2,3-b]pyridin-4-yl]pyrimidin-4-yl]propanoic Acid Synthesis of 2-methyl-2-[6-[(3R)-3-methylmorpholin-4-yl]-2-[1H-pyrrolo[2,3-b]pyridin-4-yl]pyrimidin-4-yl]propanoic acid: Into a 8-mL flask, was placed 2-methyl-2-[6-[(3R)-3-methylmorpholin-4-yl]-2-[1H-pyrrolo[2,3-b]pyridin-4-yl]pyrimidin-4-yl]propanenitrile (150 mg, 0.414 mmol, 1 equiv), HCl (4 mL), CH$_3$COOH (1 mL). The resulting solution was stirred for 15 hr at 80° C. in an oil bath. The resulting mixture was concentrated. The crude product was purified by Flash-Prep-HPLC with the following conditions (IntelFlash-1): Column, C 18 silica gel; mobile phase, CH$_3$CN/0.05% NH$_4$HCO$_3$=50% increasing to CH$_3$CN/0.05% NH$_4$HCO$_3$=60%; Detector, 254 nm & 220 nm. This resulted in 4.4 mg (2.79%) of 2-methyl-2-[6-[(3R)-3-methylmorpholin-4-yl]-2-[1H-pyrrolo[2,3-b]pyridin-4-yl]pyrimidin-4-yl]propanoic acid as a light yellow solid. LC-MS-BLV-CY-244-0: (ES, m/z): 382 [M+H]$^+$. H-NMR-BLV-CY-244-0: (300 MHz, CD$_3$OD, ppm): δ 8.40-8.15 (m, 2H), 8.08 (d, J=4.8 Hz, 1H), 7.47 (d, J=3.0 Hz, 1H), 7.43 (d, J=2.7 Hz, 1H), 6.69 (s, 1H), 4.67 (brs, 1H), 4.22 (d, J=12.9 Hz, 1H), 4.06 (dd, J=11.1, 3.0 Hz, 1H), 3.87 (d, J=11.7 Hz, 1H), 3.78 (dd, J=14.1, 2.7 Hz, 1H), 3.64 (td, J=12.0, 2.4 Hz, 1H), 3.39 (td, J=12.9, 3.6 Hz, 1H), 1.67 (s, 6H), 1.37 (d, J=6.6 Hz, 3H).

Example CY-245: Preparation of (3R)-4-[6-(1-methoxy-2-methylpropan-2-yl)-2-[1H-pyrrolo[2,3-b]pyridin-4-yl]pyrimidin-4-yl]-3-methylmorpholine Synthesis of methyl 2-methyl-2-[2-methyl-6-[(3R)-3-methylmorpholin-4-yl]pyrimidin-4-yl]propanoate: Into a 50-mL round-bottom flask, was placed (3R)-4-(2,6-dichloropyrimidin-4-yl)-3-methylmorpholine (1 g, 4.030 mmol, 1 equiv), methyl 2-methylpropanoate (0.41 g, 4.030 mmol, 1.00 equiv). This was followed by the addition of Tol (10 mL) stirred at 0° C. To this was added NaHMDS (2.8 mL, 1.4 equiv) dropwise with stirring at 0° C. The resulting solution was stirred for 1 hr at room temperature. The reaction was then quenched by the addition of 50 mL of aq. NH$_4$Cl. The resulting solution was extracted with 2×100 mL of ethyl acetate. The combined organic layer was washed with 2×100 ml of brine. The mixture was dried over anhydrous sodium sulfate and concentrated. The residue was applied onto a silica gel column with ethyl acetate/petroleum ether (1:100). This resulted in 500 mg (42.29%) of methyl 2-methyl-2-[2-methyl-6-[(3R)-3-methylmorpholin-4-yl]pyrimidin-4-yl]propanoate as colorless oil. LC-MS-BLV-CY-245-1: (ES, m/z): 314 [M+H]$^+$. H-NMR-BLV-CY-245-1:

(300 MHz, CD$_3$OD, ppm): δ 6.56 (s, 1H), 4.47 (brs, 1H), 4.11-3.95 (m, 2H), 3.83-3.66 (m, 5H), 3.56 (td, J=11.9, 3.0 Hz, 1H), 3.31-3.23 (m, 1H), 1.53 (s, 6H), 1.34-1.27 (m, 3H).

Synthesis of 2-[2-chloro-6-[(3R)-3-methylmorpholin-4-yl]pyrimidin-4-yl]-2-methylpropan-1-ol: Into a 50-mL 3-necked round-bottom flask, was placed methyl 2-[2-chloro-6-[(3R)-3-methylmorpholin-4-yl]pyrimidin-4-yl]-2-methylpropanoate (400 mg, 1.275 mmol, 1 equiv). This was followed by the addition of THF (10 mL) stirred at −60° C. To this was added lithium aluminum hydride (1.0 M in THF) (10 mL, 0.319 mmol, 5 equiv) dropwise with stirring at −60° C. The resulting solution was stirred for 1 hr at −60° C. The reaction was then quenched by the addition of 60 mL of aq. NH$_4$Cl. The resulting solution was extracted with 2×100 mL of ethyl acetate. The organic layer was washed with 2×150 mL of brine. The EA mixture was dried over anhydrous sodium sulfate and concentrated. This resulted in 270 mg (74.12%) of 2-[2-chloro-6-[(3R)-3-methylmorpholin-4-yl]pyrimidin-4-yl]-2-methylpropan-1-ol as colorless oil. LC-MS-BLV-CY-245-2: (ES, m/z): 286 [M+H]$^+$.

Synthesis of (3R)-4-[2-chloro-6-(1-methoxy-2-methylpropan-2-yl)pyrimidin-4-yl]-3-methylmorpholine: Into a 25-mL round-bottom flask, was placed 2-[2-chloro-6-[(3R)-3-methylmorpholin-4-yl]pyrimidin-4-yl]-2-methylpropan-1-ol (400 mg, 1.400 mmol, 1 equiv). This was followed by the addition of DMF (5 mL) stirred at 0° C. To this was added NaH (100.77 mg, 4.199 mmol, 3.00 equiv) stirred at 0° C. for 10 min. To the mixture was added MeI (298.01 mg, 2.100 mmol, 1.5 equiv) at 0° C. The resulting solution was stirred for 4 hr at room temperature. The reaction was then quenched by the addition of 100 mL of NaHCO$_3$ and extracted with 2×50 mL of ethyl acetate. The organic layer was washed with 2×50 mL of brine. The mixture was dried over anhydrous sodium sulfate and concentrated. This resulted in 270 mg (64.34%) of (3R)-4-[2-chloro-6-(1-methoxy-2-methylpropan-2-yl)pyrimidin-4-yl]-3-methylmorpholine as a light yellow solid. LC-MS-BLV-CY-245-3: (ES, m/z): 300 [M+H]$^+$.

Synthesis of (3R)-4-[6-(1-methoxy-2-methylpropan-2-yl)-2-[1H-pyrrolo[2,3-b]pyridin-4-yl]pyrimidin-4-yl]-3-methylmorpholine: Into a 8-mL microwave and maintained with an inert atmosphere of nitrogen, was placed (3R)-4-[2-chloro-6-(1-methoxy-2-methylpropan-2-yl)pyrimidin-4-yl]-3-methylmorpholine (200 mg, 0.667 mmol, 1 equiv), Pd(dppf)Cl$_2$ (97.63 mg, 0.133 mmol, 0.2 equiv), Na$_2$CO$_3$ (141.41 mg, 1.334 mmol, 2.0 equiv), DME (5 mL), 4-(4,4,5,5-tetramethyl-1,3,2-dioxaborolan-2-yl)-1H-pyrrolo[2,3-b]pyridine (260.55 mg, 1.067 mmol, 1.6 equiv), H$_2$O (0.5 mL). The resulting solution was stirred for 1 hr at 90° C. The crude product was purified by Prep-HPLC. This resulted in 40 mg (15.72%) of (3R)-4-[6-(1-methoxy-2-methylpropan-2-yl)-2-[1H-pyrrolo[2,3-b]pyridin-4-yl]pyrimidin-4-yl]-3-methylmorpholine (FA salt) as a white solid. LC-MS-BLV-CY-245-0: (ES, m/z): 382 [M+H]$^+$. H-NMR-BLV-CY-245-0: (300 MHz, CDCl$_3$, ppm): δ 9.68 (s, 1H), 8.47 (brs, 1H), 8.18 (s, 1H), 7.51-7.45 (m, 2H), 6.50 (s, 1H), 4.59 (brs, 1H), 4.22-4.06 (m, 2H), 3.93-3.77 (m, 2H), 3.75-3.59 (m, 3H), 3.46-3.37 (m, 1H), 3.35 (s, 3H), 1.49-1.35 (m, 9H).

Example CY-246: Preparation of N-[(3,3-difluorocyclobutyl)methyl]-6-[(3R)-3-methylmorpholin-4-yl]-2-[1H-pyrrolo[2,3-b]pyridin-4-yl]pyrimidin-4-amine Synthesis of (R)—N-(2-fluoro-2-methylpropyl)-6-(3-methylmorpholino)-2-(methylthio)pyrimidin-4-amine: Into a 40-mL round-bottom flask, was placed (3R)-4-[3-chloro-5-(methylsulfanyl)phenyl]-3-methylmorpholine (300 mg, 1 equiv), 2-fluoro-2-methylpropan-1-amine hydrochloride (205.94 mg, 1.4 equiv), TEA (350.96 mg, 3.0 equiv), EtOH (4 mL). The resulting solution was stirred overnight at 70° C. The crude product was purified by Flash-Prep-HPLC 0.1% NH$_3$.H$_2$O:MeCN=55% increasing to 0.1% NH$_3$.H$_2$O:MeCN=65% within 9 min. This resulted in 200 mg of (R)—N-(2-fluoro-2-methylpropyl)-6-(3-methylmorpholino)-2-(methylthio)pyrimidin-4-amine as a white solid. LC-MS-BLV-CY-246-1: (ES, m/z): 315 [M+H]$^+$.

Synthesis of N-[(3,3-difluorocyclobutyl)methyl]-6-[(3R)-3-methylmorpholin-4-yl]-2-[1H-pyrrolo[2,3-b]pyridin-4-yl]pyrimidin-4-amine: Into a 40-mL microwave and maintained with an inert atmosphere of nitrogen, was placed (R)—N-(2-fluoro-2-methylpropyl)-6-(3-methylmorpholino)-2-(methylthio)pyrimidin-4-amine (150 mg, 1 equiv), 4-(4,4,5,5-tetramethyl-1,3,2-dioxaborolan-2-yl)-1H-pyrrolo[2,3-b]pyridine (174.84 mg, 1.5 equiv), Pd(PPh$_3$)$_4$ (110.40 mg, 0.2 equiv), CuMeSal (307.69 mg, 3.0 equiv), dioxane (10 mL). The resulting solution was stirred for 1 hr at 110° C. The crude product was purified by Prep-HPLC. This resulted in 41 mg of N-[(3,3-difluorocyclobutyl)methyl]-6-[(3R)-3-methylmorpholin-4-yl]-2-[1H-pyrrolo[2,3-b]pyridin-4-yl]pyrimidin-4-amine as a white solid. LC-MS-BLV-CY-246-0: (ES, m/z): 385 [M+H]$^+$. H-NMR-BLV-CY-246-0: (300 MHz, CD$_3$OD, ppm): δ 8.29 (d, J=5.1 Hz, 1H), 7.51-7.47 (m, 2H), 6.89 (d, J=3.5 Hz, 1H), 6.52 (s, 1H), 4.56-4.45 (m, 1H), 4.12 (d, J=13.4 Hz, 1H), 4.01 (dd, J=11.5, 3.8 Hz, 1H), 3.82 (d, J=11.5 Hz, 1H), 3.78-3.70 (m, 2H), 3.70-3.53 (m, 2H), 3.27 (dd, J=12.8, 3.9 Hz, 1H), 1.45 (s, 3H), 1.38 (s, 3H), 1.34 (d, J=6.8 Hz, 3H).

Example CY-247: Preparation of N-ethyl-6-[(3R)-3-methylmorpholin-4-yl]-2-[1H-pyrrolo[2,3-b]pyridin-4-yl]pyrimidin-4-amine Synthesis of N-ethyl-6-[(3R)-3-methylmorpholin-4-yl]-2-(methylsulfanyl)pyrimidin-4-amine: Into a 40-mL vial, was placed (3R)-4-[6-chloro-2-(methylsulfanyl)pyrimidin-4-yl]-3-methylmorpholine (1 g, 3.850 mmol, 1 equiv), Ethylamine hydrochloride (0.94 g, 3.0 equiv), DIEA (1g, 2.0 equiv), i-PrOH (10 mL). The resulting solution was stirred for 2 days at 110° C. The crude product was purified by Flash-Prep-HPLC 0.1% HCOOH:MeCN=40% increasing to 0.1% HCOOH:MeCN=55% within 10 min. This resulted in 380 mg of N-ethyl-6-[(3R)-3-methylmorpholin-4-yl]-2-(methylsulfanyl)pyrimidin-4-amine as yellow oil. LC-MS-BLV-CY-247-1: (ES, m/z): 269 [M+H]$^+$. H-NMR-BLV-CY-247-1: (300 MHz, CDCl$_3$, ppm): δ 5.07 (s, 1H), 4.61 (brs, 1H), 4.33-4.23 (m, 1H), 4.03-3.88 (m, 2H), 3.80-3.68 (m, 2H), 3.57 (td, J=12.3, 3.0 Hz, 1H), 3.30-3.15 (m, 3H), 2.48 (s, 3H), 1.31-1.20 (m, 6H).

Synthesis of N-ethyl-6-[(3R)-3-methylmorpholin-4-yl]-2-[1H-pyrrolo[2,3-b]pyridin-4-yl]pyrimidin-4-amine: Into a 40-mL microwave and maintained with an inert atmosphere of nitrogen, was placed N-ethyl-6-[(3R)-3-methylmorpholin-4-yl]-2-(methylsulfanyl)pyrimidin-4-amine (200 mg, 0.745 mmol, 1 equiv), 4-(4,4,5,5-tetramethyl-1,3,2-dioxaborolan-2-yl)-1H-pyrrolo[2,3-b]pyridine (272.86 mg, 1.118 mmol, 1.5 equiv), Pd(PPh$_3$)$_4$ (172.23 mg, 0.149 mmol, 0.2 equiv), CuMeSal (479.99 mg, 2.236 mmol, 3.0 equiv), dioxane (10 mL). The resulting solution was stirred for 1 hr at 110° C. The crude product was purified by Prep-HPLC. This resulted in 30 mg (12.0%) of N-ethyl-6-[(3R)-3-methylmorpholin-4-yl]-2-[1H-pyrrolo[2,3-b]pyridin-4-yl]pyrimidin-4-amine as a white solid. LC-MS-BLV-CY-247-0: (ES, m/z): 339 [M+H]$^+$. H-NMR-BLV-CY-247-0: (300

MHz, CD₃OD, ppm): δ 8.25 (d, J=5.2 Hz, 1H), 7.96 (d, J=5.2 Hz, 1H), 7.45 (d, J=3.5 Hz, 1H), 7.32 (d, J=3.5 Hz, 1H), 5.60 (s, 1H), 4.53 (brs, 1H), 4.07-3.98 (m, 2H), 3.87-3.73 (m, 2H), 3.67-3.55 (m, 1H), 3.50-3.42 (m, 2H), 3.29-3.23 (m, 1H), 1.37-1.23 (m, 6H).

Example CY-248: Preparation of N-(cyclopropylmethyl)-6-[(3R)-3-methylmorpholin-4-yl]-2-[1H-pyrrolo[2,3-b]pyridin-4-yl]pyrimidin-4-amine Synthesis of N-(cyclopropylmethyl)-6-[(3R)-3-methylmorpholin-4-yl]-2-(methylsulfanyl) pyrimidin-4-amine: Into a 40-mL vial, was placed (3R)-4-[6-chloro-2-(methylsulfanyl)pyrimidin-4-yl]-3-methylmorpholine (1 g, 3.850 mmol, 1 equiv), Aminomethylcyclopropane (0.82 g, 3.0 equiv), DIEA (1g, 2.0 equiv), i-PrOH (10 mL). The resulting solution was stirred for 2 days at 110° C. The crude product was purified by Flash-Prep-HPLC 0.1% HCOOH:MeCN=40% increasing to 0.1% HCOOH:MeCN=55% within 10 min. This resulted in 240 mg of N-(cyclopropylmethyl)-6-[(3R)-3-methylmorpholin-4-yl]-2-(methylsulfanyl) pyrimidin-4-amine as yellow oil. LC-MS-BLV-CY-248-1: (ES, m/z): 295 [M+H]⁺.

Synthesis of N-(cyclopropylmethyl)-6-[(3R)-3-methylmorpholin-4-yl]-2-[1H-pyrrolo[2,3-b]pyridin-4-yl]pyrimidin-4-amine: Into a 40-mL microwave and maintained with an inert atmosphere of nitrogen, was placed N-(cyclopropylmethyl)-6-[(3R)-3-methylmorpholin-4-yl]-2-(methylsulfanyl)pyrimidin-4-amine (200 mg, 0.679 mmol, 1 equiv), 4-(4,4,5,5-tetramethyl-1,3,2-dioxaborolan-2-yl)-1H-pyrrolo[2,3-b]pyridine (248.73 mg, 1.019 mmol, 1.5 equiv), Pd(PPh₃)₄ (156.99 mg, 0.136 mmol, 0.2 equiv), CuMeSal (437.54 mg, 2.038 mmol, 3.00 equiv), dioxane (10 mL). The resulting solution was stirred for 1 hr at 110° C. The crude product was purified by Prep-HPLC. This resulted in 24 mg (10%) of N-(cyclopropylmethyl)-6-[(3R)-3-methylmorpholin-4-yl]-2-[1H-pyrrolo[2,3-b]pyridin-4-yl]pyrimidin-4-amine as a white solid. LC-MS-BLV-CY-248-0: (ES, m/z): 365 [M+H]⁺. H-NMR-BLV-CY-248-0: (300 MHz, CD₃OD, ppm): δ 8.26 (d, J=4.9 Hz, 1H), 7.96 (d, J=5.2 Hz, 1H), 7.46 (d, J=3.6 Hz, 1H), 7.32 (d, J=3.6 Hz, 1H), 5.63 (s, 1H), 4.95-4.91 (m, 1H), 4.53 (brs, 1H), 4.02 (d, J=12.5 Hz, 2H), 3.89-3.73 (m, 2H), 3.67-3.54 (m, 1H), 3.29-3.22 (m, 2H), 1.32 (d, J=6.9 Hz, 3H), 1.17 (s, 1H), 0.62-0.52 (m, 2H), 0.35-0.29 (m, 2H).

Example CY-249: Preparation of N-[(3,3-difluorocyclobutyl)methyl]-6-[(3R)-3-methylmorpholin-4-yl]-2-[1H-pyrrolo[2,3-b]pyridin-4-yl]pyrimidin-4-amine Synthesis of N-[(3,3-difluorocyclobutyl) methyl]-6-[(3R)-3-methylmorpholin-4-yl]-2-(methylsulfanyl)pyrimidin-4-amine: Into a 40-mL vial, was placed (3R)-4-[6-chloro-2-(methylsulfanyl)pyrimidin-4-yl]-3-methylmorpholine (1 g, 3.850 mmol, 1 equiv), 1-(3,3-difluorocyclobutyl)methanamine (0.51 g, 4.235 mmol, 1.1 equiv), Cs₂CO₃ (2.51 g, 7.700 mmol, 2.0 equiv), i-PrOH (10 mL). The resulting solution was stirred overnight at 110° C. The crude product was purified by Flash-Prep-HPLC 0.1% NH₃.H₂O:MeCN=50% increasing to 0.1% NH₃.H₂O:MeCN=68% within 9 min. This resulted in 180 mg (13.57%) of N-[(3,3-difluorocyclobutyl) methyl]-6-[(3R)-3-methylmorpholin-4-yl]-2-(methylsulfanyl)pyrimidin-4-amine as brown oil. LC-MS-BLV-CY-249-1: (ES, m/z): 345 [M+H]⁺.

Synthesis of N-[(3,3-difluorocyclobutyl)methyl]-6-[(3R)-3-methylmorpholin-4-yl]-2-[1H-pyrrolo[2,3-b]pyridin-4-yl]pyrimidin-4-amine: Into a 40-mL microwave and maintained with an inert atmosphere of nitrogen, was placed N-[(3,3-difluorocyclobutyl)methyl]-6-[(3R)-3-methylmorpholin-4-yl]-2-(methylsulfanyl)pyrimidin-4-amine (150 mg, 0.436 mmol, 1 equiv), 4-(4,4,5,5-tetramethyl-1,3,2-dioxaborolan-2-yl)-1H-pyrrolo[2,3-b]pyridine (159.46 mg, 0.653 mmol, 1.5 equiv), Pd(PPh₃)₄ (100.65 mg, 0.087 mmol, 0.2 equiv), CuMeSal (280.52 mg, 1.307 mmol, 3.0 equiv), dioxane (10 mL). The resulting solution was stirred for 1 hr at 110° C. The crude product was purified by Prep-HPLC. This resulted in 16 mg (8.91%) of N-[(3,3-difluorocyclobutyl)methyl]-6-[(3R)-3-methylmorpholin-4-yl]-2-[1H-pyrrolo[2,3-b]pyridin-4-yl]pyrimidin-4-amine as a white solid. LC-MS-BLV-CY-249-0: (ES, m/z): 415 [M+H]⁺. H-NMR-BLV-CY-249-0: (300 MHz, CD₃OD, ppm): δ 8.26 (d, J=5.2 Hz, 1H), 8.00 (d, J=5.2 Hz, 1H), 7.46 (d, J=3.5 Hz, 1H), 7.33 (d, J=3.5 Hz, 1H), 5.64 (s, 1H), 4.52 (brs, 1H), 4.08-3.97 (m, 2H), 3.89-3.74 (m, 2H), 3.69-3.55 (m, 3H), 3.27 (dd, J=12.5, 3.9 Hz, 1H), 2.78-2.30 (m, 5H), 1.33 (d, J=6.7 Hz, 3H).

Example CY-250: Preparation of N-cyclopropyl-6-[(3R)-3-methylmorpholin-4-yl]-2-[1H-pyrrolo[2,3-b]pyridin-4-yl]pyrimidin-4-amine Synthesis of N-cyclopropyl-6-[(3R)-3-methylmorpholin-4-yl]-2-(methylsulfanyl)pyrimidin-4-amine: Into a 40-mL vial, was placed (3R)-4-[6-chloro-2-(methylsulfanyl)pyrimidin-4-yl]-3-methylmorpholine (1 g, 3.850 mmol, 1 equiv), cyclopropanamine (0.66 g, 11.550 mmol, 3.0 equiv), DIEA (1 g, 2.0 equiv), i-PrOH (10 mL). The resulting solution was stirred for 2 days at 110° C. The crude product was purified by Flash-Prep-HPLC 0.1% HCOOH:MeCN=40% increasing to 0.1% HCOOH:MeCN=55% within 10 min. This resulted in 130 mg of N-cyclopropyl-6-[(3R)-3-methylmorpholin-4-yl]-2-(methylsulfanyl)pyrimidin-4-amine as yellow oil. LC-MS-BLV-CY-250-1: (ES, m/z): 281 [M+H]⁺. H-NMR-BLV-CY-250-1: (300 MHz, CDCl₃, ppm): 65.49 (s, 1H), 5.13 (s, 1H), 4.42-4.28 (m, 1H), 3.98 (td, J=12.9, 3.5 Hz, 2H), 3.84-3.69 (m, 2H), 3.60 (td, J=11.8, 3.2 Hz, 1H), 3.24 (td, J=12.9, 4.0 Hz, 1H), 2.51-2.43 (m, 4H), 1.30 (d, J=6.7 Hz, 3H), 0.84-0.75 (m, 2H), 0.62-0.53 (m, 2H).

Synthesis of N-cyclopropyl-6-[(3R)-3-methylmorpholin-4-yl]-2-[1H-pyrrolo[2,3-b]pyridin-4-yl]pyrimidin-4-amine: Into a 8-mL microwave and maintained with an inert atmosphere of nitrogen, was placed N-cyclopropyl-6-[(3R)-3-methylmorpholin-4-yl]-2-(methylsulfanyl)pyrimidin-4-amine (100 mg, 0.357 mmol, 1 equiv), 4-(4,4,5,5-tetramethyl-1,3,2-dioxaborolan-2-yl)-1H-pyrrolo[2,3-b]pyridine (130.59 mg, 0.535 mmol, 1.5 equiv), Pd(PPh₃)₄ (82.43 mg, 0.071 mmol, 0.2 equiv), CuMeSal (229.72 mg, 1.070 mmol, 3.0 equiv), dioxane (4 mL). The resulting solution was stirred for 1 hr at 110° C. The crude product was purified by Prep-HPLC. This resulted in 6 mg (4.8%) of N-cyclopropyl-6-[(3R)-3-methylmorpholin-4-yl]-2-[1H-pyrrolo[2,3-b]pyridin-4-yl]pyrimidin-4-amine as a white solid. LC-MS-BLV-CY-250-0: (ES, m/z): 351 [M+H]⁺. H-NMR-BLV-CY-250-0: (300 MHz, CD₃OD, ppm): δ 8.25 (d, J=5.1 Hz, 1H), 7.92 (d, J=5.2 Hz, 1H), 7.46 (d, J=3.5 Hz, 1H), 7.33 (d, J=3.5 Hz, 1H), 5.87 (s, 1H), 4.58 (brs, 1H), 4.07 (t, J=12.5 Hz, 2H), 3.88-3.80 (m, 2H), 3.65 (td, J=11.8, 3.2 Hz, 1H), 3.38-3.35 (m, 1H), 2.67-2.60 (m, 1H), 1.36 (d, J=6.7 Hz, 3H), 0.89-0.83 (m, 2H), 0.64-0.59 (m, 2H).

Example CY-251: Preparation of N-(3,3-difluorocyclobutyl)-6-[(3R)-3-methylmorpholin-4-yl]-2-[1H-pyrrolo[2,3-b]pyridin-4-yl]pyrimidin-4-amine Synthesis of N-(3,3-difluorocyclobutyl)-6-[(3R)-3-methylmorpholin-4-yl]-2-(methylsulfanyl)pyrimidin-4-amine: Into a 100-mL round-bottom flask purged and maintained with an inert atmosphere of nitrogen, was placed (3R)-4-[6-chloro-2-(methylsulfanyl)pyrimidin-4-yl]-3-methylmorpholine (1 g, 3.850 mmol, 1 equiv), 3,3-difluorocyclobutan-1-amine (0.62 g, 5.775 mmol, 1.5 equiv), Pd(OAc)$_2$ (86.43 mg, 0.385 mmol, 0.10 equiv), XantPhos (0.45 g, 0.770 mmol, 0.2 equiv), Cs$_2$CO$_3$ (2.51 g, 7.700 mmol, 2.0 equiv), dioxane (20 mL). The resulting solution was stirred for 4 hr at 90° C. The solids were filtered out. The combined organic layer was concentrated. The residue was applied onto a silica gel column with ethyl acetate/petroleum ether (20:80). This resulted in 240 mg (18.87%) of N-(3,3-difluorocyclobutyl)-6-[(3R)-3-methylmorpholin-4-yl]-2-(methylsulfanyl)pyrimidin-4-amine as a brown solid. LC-MS-BLV-CY-251-1: (ES, m/z): 331 [M+H]$^+$.

Synthesis of N-(3,3-difluorocyclobutyl)-6-[(3R)-3-methylmorpholin-4-yl]-2-[1H-pyrrolo[2,3-b]pyridin-4-yl]pyrimidin-4-amine: Into a 40-mL microwave and maintained with an inert atmosphere of nitrogen, was placed N-(3,3-difluorocyclobutyl)-6-[(3R)-3-methylmorpholin-4-yl]-2-(methylsulfanyl)pyrimidin-4-amine (150 mg, 0.454 mmol, 1 equiv), 4-(4,4,5,5-tetramethyl-1,3,2-dioxaborolan-2-yl)-1H-pyrrolo[2,3-b]pyridine (166.23 mg, 0.681 mmol, 1.50 equiv), Pd(PPh$_3$)$_4$ (104.92 mg, 0.091 mmol, 0.2 equiv), CuMeSal (292.42 mg, 1.362 mmol, 3.0 equiv), dioxane (10 mL). The resulting solution was stirred for 1 hr at 110° C. This resulted in 7 mg (3.85%) of N-(3,3-difluorocyclobutyl)-6-[(3R)-3-methylmorpholin-4-yl]-2-[1H-pyrrolo[2,3-b]pyridin-4-yl]pyrimidin-4-amine as a white solid. LC-MS-BLV-CY-251-0: (ES, m/z): 401 [M+H]$^+$. H-NMR-BLV-CY-251-0: (300 MHz, CD$_3$OD, ppm): δ 8.27 (s, 1H), 8.00 (d, J=5.1 Hz, 1H), 7.48 (d, J=3.5 Hz, 1H), 7.33 (d, J=3.4 Hz, 1H), 5.63 (s, 1H), 4.54 (brs, 1H), 4.39 (brs, 1H), 4.04 (dd, J=10.9, 3.4 Hz, 2H), 3.92-3.72 (m, 2H), 3.70-3.57 (m, 1H), 3.27 (dd, J=12.4, 3.7 Hz, 1H), 3.17-3.01 (m, 2H), 2.71-2.50 (m, 2H), 1.33 (d, J=6.8 Hz, 3H).

Example CY-252: Preparation of (3R)-4-[6-(3,3-difluoropyrrolidin-1-yl)-2-[1H-pyrrolo[2,3-b]pyridin-4-yl]pyrimidin-4-yl]-3-methylmorpholine Synthesis of (3R)-4-[6-(3,3-difluoropyrrolidin-1-yl)-2-(methylsulfanyl)pyrimidin-4-yl]-3-methylmorpholine: Into a 50-mL round-bottom flask, was placed (3R)-4-[6-chloro-2-(methylsulfanyl)pyrimidin-4-yl]-3-methylmorpholine (800 mg, 3.080 mmol, 1 equiv), 3,3-difluoropyrrolidine hydrochloride (884.30 mg, 6.160 mmol, 2.0 equiv), DIEA (1194.16 mg, 9.240 mmol, 3.0 equiv), i-PrOH (15 mL). The resulting solution was stirred for 2 days at 100° C. The crude product was purified by Flash-Prep-HPLC 0.1% HCOOH:MeCN=40% increasing to 0.1% HCOOH:MeCN=55% within 8 min. This resulted in 300 mg (29.48%) of (3R)-4-[6-(3,3-difluoropyrrolidin-1-yl)-2-(methylsulfanyl)pyrimidin-4-yl]-3-methylmorpholine as yellow oil. LC-MS-BLV-CY-252-1: (ES, m/z): 331 [M+H]$^+$. H-NMR-BLV-CY-252-1: (300 MHz, CDCl$_3$, ppm): δ 5.00 (s, 1H), 4.35-4.25 (m, 1H), 3.99-3.67 (m, 8H), 3.57 (td, J=11.8, 3.1 Hz, 1H), 3.21 (td, J=12.7, 3.9 Hz, 1H), 2.53-2.39 (m, 5H), 1.27 (d, J=6.6 Hz, 3H).

Synthesis of (3R)-4-[6-(3,3-difluoropyrrolidin-1-yl)-2-[1H-pyrrolo[2,3-b]pyridin-4-yl]pyrimidin-4-yl]-3-methylmorpholine: Into a 40-mL microwave and maintained with an inert atmosphere of nitrogen, was placed (3R)-4-[6-(3,3-difluoropyrrolidin-1-yl)-2-(methylsulfanyl)pyrimidin-4-yl]-3-methylmorpholine (200 mg, 0.605 mmol, 1 equiv), 4-(4,4,5,5-tetramethyl-1,3,2-dioxaborolan-2-yl)-1H-pyrrolo[2,3-b]pyridine (221.64 mg, 0.908 mmol, 1.50 equiv), Pd(PPh$_3$)$_4$ (139.90 mg, 0.121 mmol, 0.2 equiv), CuMeSal (389.89 mg, 1.816 mmol, 3.0 equiv), dioxane (10 mL). The resulting solution was stirred for 1 hr at 110° C. The crude product was purified by Prep-HPLC. This resulted in 38 mg (15.7%) of (3R)-4-[6-(3,3-difluoropyrrolidin-1-yl)-2-[1H-pyrrolo[2,3-b]pyridin-4-yl]pyrimidin-4-yl]-3-methylmorpholine as a white solid. LC-MS-BLV-CY-252-0: (ES, m/z): 401 [M+H]$^+$. H-NMR-BLV-CY-252-0: (300 MHz, d$_6$-DMSO, ppm): δ 11.70 (s, 1H), 8.29 (d, J=5.0 Hz, 1H), 7.97 (d, J=5.0 Hz, 1H), 7.54 (d, J=3.4 Hz, 1H), 7.24 (d, J=3.4 Hz, 1H), 5.68 (s, 1H), 4.55 (brs, 1H), 4.13-3.91 (m, 4H), 3.85-3.73 (m, 3H), 3.65 (dd, J=11.8, 3.0 Hz, 1H), 3.51 (td, J=13.2, 2.4 Hz, 1H), 3.18 (td, J=12.9, 3.9 Hz, 1H), 2.63-2.55 (m, 2H), 1.22 (d, J=6.7 Hz, 3H).

Example CY-253: Preparation of (3R)-3-methyl-4-[6-(morpholin-4-yl)-2-[1H-pyrrolo[2,3-b]pyridin-4-yl]pyrimidin-4-yl]morpholine Synthesis of (3R)-3-methyl-4-[2-(methylsulfanyl)-6-(morpholin-4-yl)pyrimidin-4-yl]morpholine: Into a 40-mL vial, was placed (3R)-4-[6-chloro-2-(methylsulfanyl)pyrimidin-4-yl]-3-methylmorpholine (500 mg, 1.925 mmol, 1 equiv), morpholine (184.47 mg, 2.117 mmol, 1.1 equiv), DIEA (746.35 mg, 5.775 mmol, 3.0 equiv), i-PrOH (10 mL). The resulting solution was stirred for 2 days at 90° C. The crude product was purified by Flash-Prep-HPLC 0.1% HCOOH:MeCN=40% increasing to 0.1% HCOOH:MeCN=55% within 8 min. This resulted in 200 mg (33.4%) of (3R)-3-methyl-4-[2-(methylsulfanyl)-6-(morpholin-4-yl)pyrimidin-4-yl]morpholine as a brown oil. LC-MS-BLV-CY-232-1: (ES, m/z): 311 [M+H]$^+$.

Synthesis of (3R)-3-methyl-4-[6-(morpholin-4-yl)-2-[1H-pyrrolo[2,3-b]pyridin-4-yl]pyrimidin-4-yl]morpholine: Into a 40-mL microwave and maintained with an inert atmosphere of nitrogen, was placed (3R)-3-methyl-4-[2-(methylsulfanyl)-6-(morpholin-4-yl)pyrimidin-4-yl]morpholine (200 mg, 0.644 mmol, 1 equiv), 4-(4,4,5,5-tetramethyl-1,3,2-dioxaborolan-2-yl)-1H-pyrrolo[2,3-b]pyridine (235.91 mg, 0.966 mmol, 1.5 equiv), Pd(PPh$_3$)$_4$ (74.45 mg, 0.064 mmol, 0.1 equiv), CuMeSal (276.66 mg, 1.289 mmol, 2.0 equiv), dioxane (10 mL). The resulting solution was stirred for 1 hr at 100° C. The crude product was purified by Prep-HPLC. This resulted in 20 mg (8.2%) of (3R)-3-methyl-4-[6-(morpholin-4-yl)-2-[1H-pyrrolo[2,3-b]pyridin-4-yl]pyrimidin-4-yl]morpholine as a white solid. LC-MS-BLV-CY-253-0: (ES, m/z): 381 [M+H]$^+$. H-NMR-BLV-CY-253-0: (300 MHz, CD$_3$OD, ppm): δ 8.59 (brs, 1H), 8.27 (s, 1H), 8.02 (d, J=5.1 Hz, 1H), 7.47 (d, J=3.5 Hz, 1H), 7.29 (d, J=3.4 Hz, 1H), 5.85 (s, 1H), 4.69-4.57 (m, 1H), 4.16-4.00 (m, 2H), 3.90-3.75 (m, 6H), 3.75-3.58 (m, 5H), 3.31-3.24 (m, 1H), 1.34 (d, J=6.8 Hz, 3H).

Example CY-254: Preparation of (3R)-3-methyl-4-[6-(4-methylpiperazin-1-yl)-2-[1H-pyrrolo[2,3-b]pyridin-4-yl]pyrimidin-4-yl]morpholine Synthesis of (3R)-3-methyl-4-[6-(4-methylpiperazin-1-yl)-2-(methylsulfanyl)pyrimidin-4-yl]morpholine: Into a 40-mL vial, was placed (3R)-4-[6-chloro-2-(methylsulfanyl) pyrimidin-4-yl]-3-methylmorpholine (500 mg, 1.925 mmol, 1 equiv), 1-methylpiperazine (212.09 mg, 2.117 mmol, 1.1 equiv), DIEA (746.35 mg, 5.775 mmol, 3.0 equiv), i-PrOH (10 mL). The resulting solution was stirred for 2 days at 90° C. The crude product was purified by Flash-Prep-HPLC 0.1% HCOOH:MeCN=40% increasing to 0.1% HCOOH: MeCN=55% within 8 min. This resulted in 370 mg (59.42%) of (3R)-3-methyl-4-[6-(4-methylpiperazin-1-yl)-2-(methylsulfanyl)pyrimidin-4-yl]morpholine as a brown oil. LC-MS-BLV-CY-254-1: (ES, m/z): 324 [M+H]$^+$. H-NMR-BLV-CY-254-1: (300 MHz, CDCl$_3$, ppm): δ 5.25 (s, 1H), 4.38-4.26 (m, 1H), 3.98 (dd, J=11.1, 3.6 Hz, 1H), 3.89 (dd, J=13.2, 3.0 Hz, 1H), 3.79-3.69 (m, 2H), 3.62-3.52 (m, 5H), 3.20 (td, J=12.7, 3.9 Hz, 1H), 2.49-2.46 (m, 7H), 2.35 (s, 3H), 1.26 (d, J=6.7 Hz, 3H).

Synthesis of (3R)-3-methyl-4-[6-(4-methylpiperazin-1-yl)-2-[1H-pyrrolo[2,3-b]pyridin-4-yl]pyrimidin-4-yl]morpholine: Into a 40-mL microwave and maintained with an inert atmosphere of nitrogen, was placed (3R)-3-methyl-4-[6-(4-methylpiperazin-1-yl)-2-(methylsulfanyl)pyrimidin-4-yl]morpholine (200 mg, 0.618 mmol, 1 equiv), 4-(4,4,5,5-tetramethyl-1,3,2-dioxaborolan-2-yl)-1H-pyrrolo[2,3-b]pyridine (226.40 mg, 0.927 mmol, 1.5 equiv), Pd(PPh$_3$)$_4$ (71.45 mg, 0.062 mmol, 0.1 equiv), CuMeSal (265.50 mg, 1.237 mmol, 2.0 equiv), dioxane (10 mL). The resulting solution was stirred for 1 hr at 100° C. The crude product was purified by Prep-HPLC. This resulted in 6 mg (2.48%) of (3R)-3-methyl-4-[6-(4-methylpiperazin-1-yl)-2-[1H-pyrrolo[2,3-b]pyridin-4-yl]pyrimidin-4-yl]morpholine as a white solid. LC-MS-BLV-CY-254-0: (ES, m/z): 394 [M+H]$^+$. H-NMR-BLV-CY-254-0: (300 MHz, d$_6$-DMSO, ppm) δ 11.70 (s, 1H), 8.28 (d, J=5.0 Hz, 1H), 7.92 (d, J=5.0 Hz, 1H), 7.54 (s, 1H), 7.15 (d, J=3.3 Hz, 1H), 5.92 (s, 1H), 4.59 (brs, 1H), 4.07 (d, J=12.9 Hz, 1H), 3.96 (d, J=11.5 Hz, 1H), 3.78-3.75 (m, 1H), 3.69-3.63 (m, 5H), 3.54-3.45 (m, 1H), 3.16 (td, J=12.4, 3.6 Hz, 1H), 2.43-3.40 (m, 4H), 2.23 (s, 3H), 1.21 (d, J=6.6 Hz, 3H).

Example CY-257-0: Preparation of 2-[2-chloro-6-[(3R)-3-methylmorpholin-4-yl]pyrimidin-4-yl]-1,1,1-trifluoropropan-2-ol Synthesis of 1-(2,6-dichloropyrimidin-4-yl)ethan-1-one: Into a 250-mL 3-necked round-bottom flask purged and maintained with an inert atmosphere of nitrogen, was placed methyl 2,6-dichloropyrimidine-4-carboxylate (5 g, 24.153 mmol, 1 equiv), THF (120 mL). This was followed by the addition of CH$_3$MgBr (3M) (13 mL, 39.0 mmol, 1.61 equiv) dropwise with stirring at −78° C. The resulting solution was stirred for 1.5 hr at −78° C. in a liquid nitrogen bath. The reaction was then quenched by the addition of 40 mL of brine below 0° C. The resulting solution was diluted with 140 mL of H$_2$O. The resulting solution was extracted with 2×150 mL of ethyl acetate and the organic layers combined and concentrated. The residue was applied onto a silica gel column with ethyl acetate/petroleum ether (1/30). This resulted in 3.9 g (84.53%) of 1-(2,6-dichloropyrimidin-4-yl)ethan-1-one as yellow oil. H-NMR-BLV-CY-230-4: (300 MHz, CDCl$_3$, ppm): δ 7.85 (s, 1H), 2.70 (s, 3H).

Synthesis of 1-[2-chloro-6-[(3R)-3-methylmorpholin-4-yl]pyrimidin-4-yl]ethan-1-one: Into a 250-mL 3-necked round-bottom flask, was placed 1-(2,6-dichloropyrimidin-4-yl)ethan-1-one (2.9 g, 15.182 mmol, 1 equiv), DCM (60 mL), TEA (2.0 g, 19.765 mmol, 1.30 equiv). This was followed by the addition of (3R)-3-methylmorpholine (1.7 g, 16.807 mmol, 1.11 equiv) dropwise with stirring at 0° C. The resulting solution was stirred for 2 hr at room temperature. The resulting mixture was concentrated. The residue was applied onto a silica gel column with ethyl acetate/ petroleum ether (1/15-1/9). This resulted in 1.58 g (40.70%) of 1-[2-chloro-6-[(3R)-3-methylmorpholin-4-yl]pyrimidin-4-yl]ethan-1-one as a light yellow solid. LC-MS-BLV-CY-230-6: (ES, m/z): 256 [M+H]$^+$. H-NMR-BLV-CY-230-6: (300 MHz, CDCl$_3$, ppm): δ 7.00 (s, 1H), 4.33 (brs, 1H), 4.13-4.09 (m, 1H), 4.05-4.00 (m, 1H), 3.80 (d, J=11.7 Hz, 1H), 3.69 (dd, J=11.4, 3.0 Hz, 1H), 3.54 (td, J=12.3, 3.0 Hz, 1H), 3.32 (td, J=12.9, 3.0 Hz, 1H), 2.63 (s, 3H), 1.35 (d, J=6.9 Hz, 3H).

Synthesis of 2-[2-chloro-6-[(3R)-3-methylmorpholin-4-yl]pyrimidin-4-yl]-1,1,1-trifluoropropan-2-ol: Into a 100-mL 3-necked round-bottom flask, was placed 1-[2-chloro-6-[(3R)-3-methylmorpholin-4-yl]pyrimidin-4-yl]ethan-1-one (1.58 g, 6.179 mmol, 1 equiv), THF (20 mL, 246.860 mmol, 39.95 equiv). This was followed by the addition of TMSCF$_3$ (4.4 g, 30.943 mmol, 5.01 equiv) dropwise with stirring at 0° C. To this was added TBAF (16 mg, 0.061 mmol, 0.01 equiv) and CsF (188 mg, 1.238 mmol, 0.20 equiv) at 0° C. The resulting solution was stirred for 6 hr at room temperature. To this was added TBAF (0.81 g, 3.098 mmol, 0.50 equiv). The resulting solution was stirred for 15 hr at room temperature. The reaction was then quenched by the addition of 100 mL of water/ice. The resulting solution was extracted with 2×100 mL of ethyl acetate and the organic layers combined and concentrated. The crude product was purified by Flash-Prep-HPLC with the following conditions (IntelFlash-1): Column, C18 silica gel; mobile phase, CH$_3$CN/0.05% HCOOH=60% increasing to CH$_3$CN/ 0.05% HCOOH=70%; Detector, 254 nm& 220 nm. This resulted in 1.7 g (84.47%) of 2-[2-chloro-6-[(3R)-3-methylmorpholin-4-yl]pyrimidin-4-yl]-1,1,1-trifluoropropan-2-ol as a yellow solid. LC-MS-BLV-CY-230-7: (ES, m/z): 326 [M+H]$^+$. H-NMR-BLV-CY-230-7: (300 MHz, CDCl$_3$, ppm): δ 6.46 (s, 1H), 5.38 (d, J=4.5 Hz, 1H), 4.36 (brs, 1H), 4.05 (dd, J=11.4, 3.6 Hz, 2H), 3.83 (d, J=12.6 Hz, 1H), 3.73 (dd, J=11.7, 3.3 Hz, 1H), 3.59 (td, J=11.7, 3.0 Hz, 1H), 3.35 (td, J=13.2, 3.9 Hz, 1H), 1.68 (s, 3H), 1.37 (dd, J=6.9, 4.5 Hz, 3H).

Synthesis of 1,1,1-trifluoro-2-[6-[(3R)-3-methylmorpholin-4-yl]-2-[1H-pyrrolo[2,3-b]pyridin-4-yl]pyrimidin-4-yl] propan-2-ol: Into a 20-mL microwave tube, was placed 2-[2-chloro-6-[(3R)-3-methylmorpholin-4-yl]pyrimidin-4-yl]-1,1,1-trifluoropropan-2-ol (100 mg, 0.307 mmol, 1 equiv), DME (4 mL), 4-(4,4,5,5-tetramethyl-1,3,2-dioxaborolan-2-yl)-1H-pyrrolo[2,3-b]pyridine (113 mg, 0.463 mmol, 1.51 equiv), Pd(dppf)Cl$_2$ (23 mg, 0.031 mmol, 0.10 equiv), K$_2$CO$_3$ (85 mg, 0.615 mmol, 2.00 equiv), H$_2$O (0.4 mL). The final reaction mixture was irradiated with microwave radiation for 40 min at 100° C. The crude product was purified by Flash-Prep-HPLC with the following conditions (IntelFlash-1): Column, C18 silica gel; mobile phase, CH$_3$CN/0.05% NH$_3$.H$_2$O=45% increasing to CH$_3$CN/ 0.05% NH$_3$.H$_2$O=55%; Detector, 254 nm & 220 nm. This resulted in 40 mg (31.98%) of 1,1,1-trifluoro-2-[6-[(3R)-3-methylmorpholin-4-yl]-2-[1H-pyrrolo[2,3-b]pyridin-4-yl] pyrimidin-4-yl]propan-2-ol as a light yellow solid. LC-MS-BLV-CY-257-0: (ES, m/z): 408 [M+H]$^+$. H-NMR-BLV-CY-257-0: (300 MHz, CD$_3$OD, ppm): δ 8.31 (d, J=5.1 Hz, 1H), 8.10 (d, J=5.1 Hz, 1H), 7.51 (d, J=3.6 Hz, 1H), 7.36 (d, J=3.6 Hz, 1H), 7.08 (d, J=1.5 Hz, 1H), 4.66 (brs, 1H), 4.26 (d, J=11.4 Hz, 1H), 4.09 (dd, J=11.4, 3.9 Hz, 1H), 3.89 (d, J=11.7 Hz, 1H), 3.80 (dd, J=11.4, 2.7 Hz, 1H), 3.66 (t, J=11.1 Hz, 1H), 3.44 (td, J=12.0, 2.1 Hz, 1H), 1.84 (s, 3H), 1.40 (d, J=6.6 Hz, 3H).

Example A

The compounds below are prepared by methods substantially identical, similar, or analogous to those disclosed in the General Scheme and above Examples.

| Compound | Name | m/z(MH+) |
|---|---|---|
| A-1 | 6-((R)-3-methylmorpholino)-2-(1H-pyrrolo[2,3-b]pyridin-4-yl)-N-(((S)-tetrahydrofuran-3-yl)methyl)pyrimidin-4-amine | 395 |
| A-2 | 6-((R)-3-methylmorpholino)-2-(1H-pyrrolo[2,3-b]pyridin-4-yl)-N-(((R)-tetrahydrofuran-3-yl)methyl)pyrimidin-4-amine | 395 |
| A-3 | (R)-6-(3-methylmorpholino)-N-(oxetan-3-ylmethyl)-2-(1H-pyrrolo[2,3-b]pyridin-4-yl)pyrimidin-4-amine | 381 |
| A-4 | (R)-N-((4,4-difluorocyclohexyl)methyl)-6-(3-methylmorpholino)-2-(1H-pyrrolo[2,3-b]pyridin-4-yl)pyrimidin-4-amine | 443 |
| A-5 | (R)-6-(3-methylmorpholino)-2-(1H-pyrrolo[2,3-b]pyridin-4-yl)-N-((tetrahydro-2H-pyran-4-yl)methyl)pyrimidin-4-amine | 409 |

Biological Example 1: Enzyme ATR

ATR for use in the in vitro enzyme assay was obtained from HeLa nuclear extract (CIL Biotech, Mons, Belgium) by immunoprecipitation with rabbit polyclonal antiserum raised to amino acids 400-480 of ATR (Tibbetts R S et al, 1999, Genes Dev. 13:152-157) contained in the following buffer (25 mM HEPES (pH7.4), 2 mM $MgCl_2$, 250 mM NaCl, 0.5 mM EDTA, 0.1 mM $Na_3VO_4$, 10% v/v glycerol, and 0.01% v/v Tween 20). ATR-antibody complexes were isolated from nuclear extract by incubating with protein A-Sepharose beads (Sigma, #P3476) for 1 hour and then through centrifugation to recover the beads. In the well of a 96-well plate, 10 ATR-containing Sepharose beads were incubated with 1 μg of substrate glutathione S-transferase-p53N66 ($NH_2$-terminal 66 amino acids of p53 fused to glutathione ^-transferase was expressed in E. coli) in ATR assay buffer (50 mM HEPES (pH 7.4), 150 mM NaCl, 6 mM $MgCl_2$, 4 mM $MnCl_2$, 0.1 mM $Na_3VO_4$, 0.1 mM DTT, and 10% (v/v) glycerol) at 37° C. in the presence or absence of inhibitor. After 10 minutes with gentle shaking, ATP was added to a final concentration of 3 μM and the reaction continued at 37° C. for an additional 1 hour. The reaction was stopped by addition of lOOμi PBS and the reaction was transferred to a white opaque glutathione coated 96-well plate (NUNC #436033) and incubated overnight at 4° C. This plate was then washed with PBS/0.05%>(v/v) Tween 20, blotted dry, and analyzed by a standard ELISA (Enzyme-Linked Immunosorbent Assay) technique with a phospho-serine 15 p53 (16G78) antibody (Cell Signaling Technology, #9286). The detection of phosphorylated glutathione S-transferase-pSSNee substrate was performed in combination with a goat anti-mouse horseradish peroxidase-conjugated secondary antibody (Pierce, #31430). Enhanced chemiluminescence solution (NEN, Boston, Mass.) was used to produce a signal and chemiluminescent detection was carried out via a TopCount (Packard, Meriden, Conn.) plate reader. The resulting calculated %>enzyme activity (Activity Base, IDBS) was then used to determine the $IC_{50}$ values for the compounds ($IC_{50}$ taken as the concentration at which 50% of the enzyme activity is inhibited).

The following table lists the $IC_{50}$ values of for certain compounds of the invention.

| Compound | ATR IC50 |
|---|---|
| AZD-6738 | <3 nM |
| CY-200-1 | <3 nM |
| CY-209 | <3 nM |
| CY-212 | <3 nM |
| CY-237 | <3 nM |
| CY-249 | <3 nM |
| CY-257 | <3 nM |

Biological Example 2: Cellular Assays—ATR

ATM and ATR have distinct and overlapping responses to DNA damage. They must participate together and responses must be co-ordinated. Both pathways may be activated by ionising radiation, however only ATR is activated by UV. Since UV treatment is not practical for use in a high throughput cell assay, the UV mimetic 4NQ0 (Sigma) was chosen to activate the ATR DNA damage response pathway. Chk1, a downstream protein kinase of ATR, plays a key role in DNA damage checkpoint control. Activation of Chk1 involves phosphorylation of Ser317 and Ser345 (regarded as the preferential target for phosphorylation/activation by ATR). This assay measures a decrease in phosphorylation of Chk1 (Ser 345) in HT29 colon adenocarcinoma cells following treatment with compound and the UV mimetic 4NQ0. Compounds dose ranges were created by diluting in 100% DMSO and then further into assay media (EMEM, 10% FCS, 1% glutamine) using a Labcyte Echo Acoustic dispensing instrument. Cells were plated in 384 well Costar plates at $9 \times 10^4$ cells per ml in 40 μl^ EMEM, 10% FCS, 1% glutamine and grown for 24 hrs. Following addition of compound the cells were incubated for 60 minutes. A final concentration of 3 μM 4NQ0 (prepared in 100% DMSO) was then added using the Labcyte Echo and the cells incubated for a further 60 mins. The cells are then fixed by adding 40 μl^ 3.7% v/v formaldehyde solution for 20 minutes. After removal of fix, cells were washed with PBS and permeabilised in 40 μE of PBS containing 0.1% Triton™ X-100. Cells are then washed and 15 μl primary antibody solution (pChk1 Ser345) added and the plates incubated at 4° C. overnight. The primary antibody is then washed off, and 20 μl secondary antibody solution (goat anti-rabbit Alexa Fluor 488, Invitrogen) and I μM Hoechst 33258 (Invitrogen) is added for 90 mins at room temperature. The plates are washed and left in 40 μl PBS. Plates were then read on an ArrayScan Vti instrument to determine staining intensities, and dose responses were obtained and used to determine the $IC_{50}$ values for the compounds.

Biological Example 3: In Vitro Anti-Proliferation Assay in ATM-Deficient Colorectal Cancer LoVo Cell Lines Cell antiproliferation was assayed by PerkinElmer ATPlite™ Luminescence Assay System. Briefly, the various test cancer cell lines were plated at a density of about $1 \times 10^4$ cells per well in Costar 96-well plates, and were incubated with different concentrations of compounds for about 72 hours in medium supplemented with 5% FBS. One lyophilized substrate solution vial was then reconstituted by adding 5 mL of substrate buffer solution, and was agitated gently until the solution was homogeneous. About 50 μL of mammalian cell lysis solution was added to 100 μL of cell suspension per well of a microplate, and the plate was shaken for about five minutes in an orbital shaker at ~700 rpm. This procedure was used to lyse the cells and to stabilize the ATP. Next, 50 μL substrate solution was added to the wells and microplate was shaken for five minutes in an orbital shaker at ~700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention. The following table lists the $IC_{50}$ values of several cancer cell lines (5% FBS) for certain compounds of the invention.

| Compound | LoVo IC50 |
|---|---|
| AZD-6738 | 0.80 uM |
| CY-237 | 0.48 uM |
| CY-249 | 0.51 uM |
| CY-257 | 0.83 uM |

Biological Example 4: Mice PK Study

The pharmacokinetics of compounds were evaluated in CD-1 mouse via Intravenous and Oral Administration. The IV dose was administered as a slow bolus in the Jugular vein, and oral doses were administered by gavage. The formulation for IV dosing was 5% DMSO in 20% HPBCD in water, and the PO formulation was 2.5% DMSO, 10% EtOH, 20% Cremphor EL, 67.5% D5W. The PK time point for the IV arm was 5, 15, 30 min, 1, 2, 4, 6, 8, 12, 24 hours post dose, and for PO arm was 15, 30 min, 1, 2, 4, 6, 8, 12, 24 hours post dose. Approximately 0.03 mL blood was collected at each time point. Blood of each sample was transferred into plastic micro centrifuge tubes containing EDTA-K2 and collect plasma within 15 min by centrifugation at 4000 g for 5 minutes in a 4° C. centrifuge. Plasma samples were stored in polypropylene tubes. The samples were stored in a freezer at −75±15° C. prior to analysis. Concentrations of compounds in the plasma samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data was described using descriptive statistics such as mean, standard deviation. Additional pharmacokinetic or statistical analysis was performed at the discretion of the contributing scientist, and was documented in the data summary. The $AUC_{last}$ of oral dosing of po, 10 mg/kg is shown in the Table below.

| Compound | $AUC_{last}$(h*ng/mL) |
|---|---|
| AZD-6738 | 3,100 |
| CY-237 | 4,392 |

What is claimed is:

1. A compound of Formula (I), or an N-oxide thereof, or a pharmaceutically acceptable salt, solvate, polymorph, tautomer, stereoisomer, or an isotopic form of said compound of Formula (I) or N-oxide thereof:

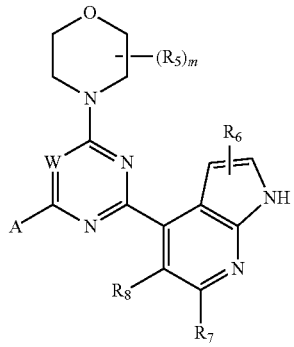

wherein
A is

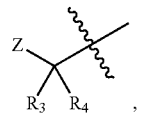

each of $R_3$, and $R_4$, independently, is H, D, halo, alkyl, or halo-alkyl;
Z is H, D, OH, halo, amine, cyano, C(O)OH, $C(O)NH_2$, alkyl, alkenyl, alkynyl, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl of Z is optionally substituted with one or more $R_d$;
W is $C(R_a)$;
each of $R_5$, $R_6$, $R_7$, and $R_8$, independently, is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $P(O)R_bR_c$, alkyl-$P(O)R_bR_c$, $C(O)N(R_b)R_c$, $N(R_b)C(O)R_c$, $S(O)(=N(R_b))R_c$, —N=S(O)$R_bR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;
$R_a$, $R_b$, $R_c$ and $R_d$, independently, is H, D, alkyl, alkenyl, alkynyl, halo, cyano, amine, nitro, hydroxy, =O, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$; and
$R_e$ is H, D, alkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl; and m, and n, independently, is 0, 1, 2, or 3.

2. The compound according to claim 1 or an N-oxide thereof, or a pharmaceutically acceptable salt, solvate, polymorph, tautomer, stereoisomer, or an isotopic form thereof, wherein the compound is represented by Formula (II)

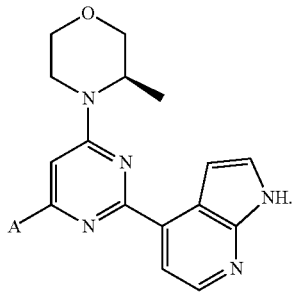

3. The compound according to claim 1 or an N-oxide thereof, or a pharmaceutically acceptable salt, solvate, polymorph, tautomer, stereoisomer, or an isotopic form thereof, wherein the compound is
- (R)-2-methyl-2-(6-(3-methylmorpholino)-2-(1H-pyrrolo [2,3-b]pyridin-4-yl)pyrimidin-4-yl)propanenitrile,
- (R)-4-(2-(1H-pyrrolo[2,3-b]pyridin-4-yl)-6-(1,1,1-trifluoro-2-methylpropan-2-yl)pyrimidin-4-yl)-3-methylmorpholine,
- 1,1,1-trifluoro-2-(6-((R)-3-methylmorpholino)-2-(1H-pyrrolo[2,3-b]pyridin-4-yl)pyrimidin-4-yl)propan-2-ol,
- (R)-2-(6-(3-methylmorpholino)-2-(1H-pyrrolo[2,3-b] pyridin-4-yl)pyrimidin-4-yl)propan-2-ol, or
- (R)-2-(6-(3-methylmorpholino)-2-(1H-pyrrolo[2,3-b] pyridin-4-yl)pyrimidin-4-yl)propan-2-amine.

4. A pharmaceutical composition comprising a compound of Formula (I) or an N-oxide thereof as defined in claim 1, or a pharmaceutically acceptable salt, solvate, polymorph, tautomer, stereoisomer, or an isotopic form of said compound of Formula (I) or an N-oxide thereof, and a pharmaceutically acceptable diluent or carrier.

5. A method of inhibiting ATR (Ataxia telangiectasia and Rad3-related) protein kinase activity in a subject in need thereof, said method comprising administering to the subject in need thereof an effective amount of a compound of Formula (I) or an N-oxide thereof as defined in claim 1, or a pharmaceutically acceptable salt, solvate, polymorph, tautomer, stereoisomer, or an isotopic form of said compound of Formula (I) or an N-oxide thereof.

* * * * *

UNITED STATES PATENT AND TRADEMARK OFFICE
CERTIFICATE OF CORRECTION

PATENT NO. : 11,236,089 B2
APPLICATION NO. : 16/801322
DATED : February 1, 2022
INVENTOR(S) : Xiang Li et al.

It is certified that error appears in the above-identified patent and that said Letters Patent is hereby corrected as shown below:

On the Title Page

Item (12), "Li" should read -- Li et al. --.

Item (72), please add an inventor -- Yi Chen, Pleasanton, CA (US) --.

In the Claims

At Column 77, Claim number 3, Line number 24, please replace "(R)-2-methyl-2-(6-(3-methylmorpholino)-2-(1H-pyrrolo[2,3-b)]pyridin-4-yl)pyrimidin-4-yl)propanenitrile" with -- (R)-2-methyl-2-(6-(3-methylmorpholino)-2-(1H-pyrrolo[2,3-b]pyridin-4-yl)pyrimidin-4-yl)propanenitrile --.

Signed and Sealed this
Thirty-first Day of January, 2023

Katherine Kelly Vidal
*Director of the United States Patent and Trademark Office*